(12) United States Patent
Mather et al.

(10) Patent No.: US 8,187,594 B2
(45) Date of Patent: May 29, 2012

(54) TRANSFERRIN RECEPTOR ANTIBODIES

(75) Inventors: Jennie P. Mather, Millbrae, CA (US); Penelope E. Roberts, Millbrae, CA (US); Ronghao Li, Millbrae, CA (US)

(73) Assignee: MacroGenics, Inc., Rockville, MD (US)

( * ) Notice: Subject to any disclaimer, the term of this patent is extended or adjusted under 35 U.S.C. 154(b) by 280 days.

(21) Appl. No.: 12/483,774

(22) Filed: Jun. 12, 2009

(65) Prior Publication Data
US 2010/0166745 A1    Jul. 1, 2010

Related U.S. Application Data

(62) Division of application No. 11/147,942, filed on Jun. 7, 2005, now Pat. No. 7,572,895.

(60) Provisional application No. 60/578,103, filed on Jun. 7, 2004.

(51) Int. Cl.
*A61K 39/395* (2006.01)
*A61K 39/00* (2006.01)
*C07K 16/00* (2006.01)
*C12P 21/08* (2006.01)

(52) U.S. Cl. ............... 424/130.1; 424/133.1; 424/138.1; 424/141.1; 424/152.1; 424/155.1; 424/156.1; 424/178.1; 424/181.1; 530/387.1; 530/388.1; 530/388.22; 530/388.8; 530/389.1; 530/389.7; 530/391.1; 530/391.7

(58) Field of Classification Search .................. None
See application file for complete search history.

(56) References Cited

U.S. PATENT DOCUMENTS

| | | | |
|---|---|---|---|
| 5,667,781 A * | 9/1997 | Trowbridge et al. | ....... 424/143.1 |
| 5,907,033 A | 5/1999 | Radka et al. | |
| 5,925,740 A | 7/1999 | Mosley et al. | |
| 6,787,153 B1 | 9/2004 | Hosokawa et al. | |

OTHER PUBLICATIONS

Janeway et al. (Immunobiology 5, 2001, p. 100-101).*
Rudikoff et al. (Proc. Natl. Acad. Sci. USA 1982, 79:1979-1983).*
Gussow et al. (1991, Methods in Enzymology 203:99-121).*
MacCallum et al. (J. Mol. Biol. (1996) 262, 732-745).*
Casset et al. (BBRC 2003 307:198-205).*
Brooks et al., "Phase Ia Trial of Murine Immunoglobulin A Antitransferrin Receptor Antibody 42/6," Clinical Cancer Research 1: 1259-1265, Nov. 1995.
Poul et al., "Selection of tumor-specific internalizing human antibodies from phage libraries," Journal of Molecular Biology, 301(5), 1149-1161, Sep. 2000.
Taetle et al., "Mechanisms of Growth Inhibition by Anti-Transferrin Receptor Monoclonal Antibodies," Cancer Research, 46: 1759-1763, Apr. 1986.
Takahashi et al., "An Epitope on the Transferrin Receptor Preferentially Exposed During Tumor Progression in Human Lymphoma Is Close to the Ligand Binding Site," Blood 77(4): 826-832, Feb. 15, 1991.
Trowbridge et al., "Monoclonal antibody to transferrin receptor blocks transferrin binding and inhibits human tumor cell growth in vitro," Proc. Natl. Acad. Sci., 79: 1175-1179, Feb. 1982.
European Communication (Nov. 29, 2010) 05757691.0 (8 pages).
European Search Report EP06734254 (9 pages), Jan. 20, 2010.
Repovic, et al., "Oncostatin-M induction of vascular endothelial growth factor expression in astroglioma cells", Oncogene, Nature Publishing Group, vol. 22, No. 50, Nov. 6, 2003, pp. 8117-8124.
Gomez-Lechon, "Oncostatin M: Signal Transduction and Biological Activity", Life Sciences, vol. 65, No. 20, Oct. 8, 1999, pp. 2019-2030.
Panchal, Rekha "Novel Therapeutic Strategies to Selectively Kill Cancer Cells", Biochemical Pharmacology, vol. 55, No. 3, Feb. 1, 1998, pp. 247-252.

* cited by examiner

*Primary Examiner* — Peter J Reddig
(74) *Attorney, Agent, or Firm* — William C. Schrot; Jeffrey I. Auerbach; The Auerbach Law Firm, LLC

(57) ABSTRACT

The invention provides further characterization of the disease and cancer-associated antigen, transferrin receptor. The invention also provides a novel family of antibodies that bind to the transferrin receptor, methods of diagnosing and treating various human cancers and diseases that express transferrin receptor.

24 Claims, 16 Drawing Sheets

TRANSFERRIN RECEPTOR ANTIBODIES

CROSS-REFERENCE TO RELATED APPLICATIONS

This application is a divisional of U.S. patent application Ser. No. 11/147,942 filed Jun. 7, 2005, issued as U.S. Pat. No. 7,572,895 and claims the benefit of U.S. Provisional Application No. 60/578,103 filed Jun. 7, 2004, the disclosures of which are incorporated herein by reference in their entirety.

TECHNICAL FIELD

This invention is in the fields of biology and immunotherapy. More specifically, it concerns the disease and cancer-associated antigen transferrin receptor, and polyclonal and monoclonal antibodies and other polypeptides that bind to transferrin receptor. The invention further provides the diagnosis and/or treatment of a variety of human diseases and cancers associated with transferrin receptor using antagonists, modulators and peptides that bind to transferrin receptor, including anti-transferrin receptor antibodies.

BACKGROUND OF THE INVENTION

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments. See for example, *Cancer: Principles and Practice of Oncology*, 6$^{th}$ Edition (2001) Chapt. 20 pp. 495-508. These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are two examples of such therapeutics. Alternatively, antibodies can be used to make antibody conjugates where the antibody is linked to a toxic agent and directs that agent to the tumor by specifically binding to the tumor. Gemtuzumab ozogamicin is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD oncofetal protein). Example of antibodies in clinical trials and/or approved for treatment of solid tumors include: Trastuzumab (antigen: 180 kD, HER2/neu), Edrecolomab (antigen: 40-50 kD, Ep-CAM), Anti-human milk fat globules (HMFG1) (antigen >200 kD, HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the level of expression or in access of or activity of the antibody at these sites.

Another type of immunotherapy is active immunotherapy, or vaccination, with an antigen present on a specific cancer(s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or 'cancer-like' tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up regulated and/or over-expressed in tumor tissues. In such situations, some researchers have suggested that the over-expression is linked to the acquisition of malignancy, while others suggest that the over-expression is merely a marker of a trend along a path to an increasing disease state.

An ideal diagnostic and/or therapeutic antibody would be specific for an antigen present on a large number of cancers, but absent or present only at low levels on any normal tissue. The discovery, characterization, and isolation of a novel antigen that is specifically associated with cancer(s) would be useful in many ways. First, the antigen could be used to make monoclonal antibodies against the antigen. An antibody would ideally have biological activity against cancer cells and be able to recruit the immune system's response to foreign antigens. An antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radio-isotope, a toxin, or a chemotherapeutic agent or liposome containing a chemotherapeutic agent, with the conjugated form being biologically active by virtue of the antibody directing the toxin to the antigen-containing cells.

One aspect desirable for an ideal diagnostic and/or therapeutic antibody is the discovery and characterization of an antigen that is associated with a variety of cancers. There are few antigens that are expressed on a number of types of cancer (e.g., "pan-cancer" antigen) that have limited expression on non-cancerous cells. The isolation and purification of such an antigen would be useful for making antibodies (e.g., diagnostic or therapeutic) targeting the antigen. An antibody binding to the "pan-cancer" antigen could be able to target a variety of cancers found in different tissues in contrast to an antibody against an antigen associated with only one specific type of cancer. The antigen would also be useful for drug discovery (e.g., small molecules) and for further characterization of cellular regulation, growth, and differentiation.

Transferrin receptor is broadly expressed in human tumors (Gatter et al., *Transferrin receptors in human tissues: their distribution and possible clinical relevance*, J Clin Pathol 36, 539-545 (1983)) and plays a key role in cell proliferation and survival. Antibodies that bind to the transferrin receptor have previously been shown to be efficacious in animal tumor models. In a leukemia xenograft model using CCRF-CEM cells (White et al., *Combinations of anti-transferrin receptor monoclonal antibodies inhibit human tumor cell growth in vitro and in vivo: evidence for synergistic antiproliferative effects*, Cancer Res 50, 6295-6301 (1990)) and in a M21 human melanoma xenograft (Trowbridge & Domingo, *Anti-transferrin receptor monoclonal antibody and toxin-antibody conjugates affect growth of human tumor cells*, Nature 294, 171-173 (1981)), transferrin receptor antibodies also inhibited tumor progression.

The transferrin receptor has been studied as a cancer target since the 1980s using naked antibodies, toxin conjugated antibodies and transferrin-toxin conjugates (see, e.g., Griffin et al., *Combined antitumor therapy with the chemotherapeutic drug doxorubicin and an anti-transferrin receptor immunotoxin: In vitro and in vivo studies*, J Immunol 11, 12-18 (1992); Qian et al., *Targeted drug delivery via the transferrin receptor-mediated endocytosis pathway*, Pharmacological Reviews 54, 561-587 (2002); Trowbridge & Collin et al., *Structure function analysis of the human transferrin receptor: Effects of anti-receptor monoclonal antibodies on tumor growth*, Curr Stud Hematol Blood Transf 58, 139-147 (1991)), including a phase I clinical trial with the murine IgA antibody 42/6 (Brooks et al., *Phase Ia trial of murine immunoglobulin A antitransferrin receptor antibody 42/6*, Clin Cancer Res 1, 1259-1265 (1995)). Expression of the transferrin receptor is correlated with cell proliferation and it has been suggested that this accounts for the high proportion of tumors that stain positively with transferrin receptor antibodies and limited staining of normal tissues (Gatter, 1983). It is generally accepted that transferrin receptor antibodies inhibit cell proliferation by reducing the uptake of iron into the cell (Kemp, *Iron deprivation and cancer: a view beginning with studies of monoclonal antibodies against the transferrin receptor*, Histol Histopathol 12, 291-296, (1997)). This can be achieved by blocking the interaction of the transferrin receptor with iron-charged transferrin or by altering the dynamics of transferrin receptor cycling and cell surface presentation. The effect of blocking iron uptake in tumor cells manifests initially as a cell cycle arrest, primarily in S-phase followed by an accumulation of G1 phase cells (White, 1990). The ultimate endpoint of iron withdrawal appears to vary from cytostasis to the induction of cell death.

Rat derived antibody that recognizes the murine transferrin receptor was tested in a syngeneic mouse leukemia model (Savage, et al., *Effects of monoclonal antibodies that block transferrin receptor function on the in vivo growth of a syngeneic murine leukemia*, Cancer Res 47, 747-753 (1987)). This molecule significantly improved survival relative to controls and there was no evidence of gross toxicity or evidence of damage to normal tissues recognized by the antibody over a four week treatment period. Additionally, there were no changes in erythrocyte or white blood cell counts. However, an analysis of bone marrow progenitor cells showed a two fold decrease in CFU-e/$10^6$ cells and a less pronounced reduction in CFU-c. Additional insight into the effect(s) of blocking the transferrin receptor can be provided by evaluating the results of a phase I clinical trial that was performed using the mouse antibody 42/6. In this study, there was evidence of mixed tumor responses, despite the short treatment course and poor pharmacokinetics of the mouse antibody (Brooks, 1995). An evaluation of patients treated with 42/6 showed evidence of reduced marrow BFU-e after treatment with the antibody, but the result was not statistically significant. Because transferrin receptor has been shown to be expressed on differentiating bone marrow progenitor cells (Helm et al., *Characterization and phenotypic analysis of differentiating CD34+ human bone marrow cells in liquid culture*, Eur J Haematol 59, 318-326 (1997)) it is desirable that a therapeutic agent incorporating an anti-transferrin receptor antibody have a potential therapeutic effect that outweighs the potential for bone marrow toxicity.

What is needed are novel targets on the surface of diseased and/or cancer cells that may be used to diagnose and treat such diseases and/or cancers with antibodies and other agents which specifically recognize the cell surface targets. There exists a further need, based on the discoveries disclosed herein, for novel antibodies and other agents which specifically recognize targets on the surface of cells that can modulate, either by reducing or enhancing, the disease-promoting activities of transferrin receptor. It is an object of this invention to identify antagonists of human transferrin receptor that are capable of inhibiting its disease-associated activities. It is another object to provide novel compounds for use in the assay of transferrin receptor, and for use as immunogens or for selecting anti-human transferrin receptor antibodies.

As will be described in more detail below, the present inventors have discovered a novel epitope of the human transferrin receptor, identified as the antigen target of the novel antagonists, modulators and antibodies provided herein.

SUMMARY OF THE INVENTION

The invention provides for transferrin receptor antagonists, modulators, and monoclonal antibodies that bind to transferrin receptor, which is expressed on a variety of human cancers. In one aspect, the invention is a family of monoclonal antibodies that bind to transferrin receptor.

In another aspect, the invention is a monoclonal antibody anti-transferrin receptor that is produced by the host cell line CA130.3.13C9.1A7 deposited on 8 Jun. 2004 at the American Type Culture Collection with a Patent Deposit Designation of PTA-6055.

In yet another aspect, the invention is a method of generating monoclonal antibody anti-transferrin receptor reactive with diseased and/or cancerous cells comprising the steps of: (a) immunizing a host mammal with an immunogen; (b) obtaining lymphocytes from the mammal; (c) fusing lymphocytes (b) with a myeloma cell line to produce a hybridoma; (d) culturing the hybridoma of (c) to produce monoclonal antibodies; and (e) screening the antibodies to select only those antibodies which bind to diseased and/or cancerous cells or cell lines but do not bind to non-cancerous or normal cells or cell lines, or bind to normal cells at a lower level or in a different fashion.

In another aspect, the invention is a method of generating an anti-transferrin receptor antibody comprising culturing a host cell encoding such antibody or progeny thereof under conditions that allow production of the antibody, and purifying the anti-transferrin receptor antibody.

In another aspect, the invention provides methods of generating any of the antibodies (or polypeptides) described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is an anti-transferrin receptor antibody or a polypeptide (which may or may not be an antibody) that competitively inhibits preferential binding of an anti-transferrin receptor antibody to transferrin receptor. In some embodiments, the invention is an antibody or a polypeptide (which may or may not be an antibody) that binds preferentially to the same epitope(s) on transferrin receptor as the LUCA31 antibody.

In another aspect, the invention is an transferrin receptor modulator (which may or may not be a polypeptide) that competitively inhibits preferential binding of an anti-transferrin receptor antibody to transferrin receptor. In some embodiments, the invention can be a small molecule or chemical compound that binds preferentially to the same or different epitope(s) on transferrin receptor as other anti-transferrin receptor antibodies.

In yet another aspect, the invention is a composition comprising transferrin receptor bound by an antibody specific for an epitope of transferrin receptor. In one embodiment, the antibody is anti-transferrin receptor. In other embodiments, two or more anti-transferrin receptor antibodies are administered, with such antibodies mapping to two or more different epitopes of transferrin receptor. In some embodiments, the anti-transferrin receptor antibody is linked to a therapeutic agent or a detectable label.

In another aspect, the invention is an antibody comprising a fragment or a region of a LUCA31 antibody. In one embodiment, the fragment is a light chain of the antibody. In another embodiment, the fragment is a heavy chain of the antibody. In yet another embodiment, the fragment contains one or more variable regions from a light chain and/or a heavy chain of the antibody. In yet another embodiment, the fragment contains one or more complementarity determining regions (CDRs) from a light chain and/or a heavy chain of the antibody.

In another aspect, the invention provides polypeptides comprising any of the following: a) one or more CDRs (or fragments thereof) from the light or heavy chain; b) three CDRs from the light chain; c) three CDRs from the heavy chain; d) three CDRs from the light chain and three CDRs from the heavy chain; e) the light chain variable region; f) the heavy chain variable region of the anti-transferrin receptor antibody. In preferred embodiments, these polypeptides are selected from sequences of the LUCA31 antibody.

In another aspect, the invention is a humanized antibody. In some embodiments, the humanized antibody comprises one or more CDRs of a non-human anti-transferrin receptor antibody. In some embodiments, the humanized antibody binds to the same or different epitope(s) as other LUCA31. Generally, a humanized antibody of the invention comprises one or more (one, two, three, four, five, six, or fragments thereof) CDRs which are the same and/or derived from the CDR(s) of the original non-human anti-transferrin receptor antibody. In some embodiments, the human antibody binds to the same or different epitope(s) as other anti-transferrin receptor antibodies. In another aspect, the invention is a chimeric antibody comprising variable regions derived from variable regions of a heavy chain and a light chain of a non-human anti-transferrin receptor antibody and constant regions derived from constant regions of a heavy chain and a light chain of a human antibody.

In another aspect, the invention is an isolated polynucleotide that encodes an antibody LUCA31 that is produced by a host cell with a deposit number of ATCC No. PTA-6055, or progeny thereof. This invention encompasses antibody polypeptides having the inherent binding or biological activities of any of the above-specified antibodies. In another aspect, the invention provides polynucleotides encoding any of the antibodies (including antibody fragments) as well as any other polypeptides described herein.

In another aspect, the invention is a pharmaceutical composition comprising any of the polypeptides (including any of the antibodies described herein) or polynucleotides described herein, such as pharmaceutical compositions comprising an anti-transferrin receptor antibody linked to a chemotherapeutic agent, an antibody comprising a fragment of an anti-transferrin receptor antibody, a humanized antibody of a non-human anti-transferrin receptor antibody, a chimeric antibody comprising variable regions derived from variable regions of a non-human anti-transferrin receptor antibody and constant regions derived from constant regions of a human antibody, or a human antibody with one or more properties of a non-human anti-transferrin receptor antibody, or any of the anti-transferrin receptor antibody described herein linked to a chemotherapeutic agent (such as a radioactive moiety), and a pharmaceutically acceptable excipient.

In one aspect, the invention is a composition comprising an anti-transferrin receptor antibody bound to transferrin receptor present on a diseased or cancerous cell. In preferred embodiments, the cancer cell is selected from the group consisting of ovarian, lung, prostate, pancreatic, colon, and breast cancer cells. In some embodiments, the cancer cell is isolated. In some embodiments, the cancer cell is in a biological sample. Generally, the biological sample is from an individual, such as a human.

In another aspect, the invention is a method of diagnosing disease in an individual by detecting transferrin receptor on cells from the individual, particularly diseases or disorders associated with inflammatory or autoimmune responses in individuals. In other aspects of the invention, methods are provided for modulating inflammatory or autoimmune responses in individuals. Diseases and conditions resulting from inflammation and autoimmune disorders that may be subject to treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury. The antibodies of this invention find applicability in administration to individuals in need of treatment for such conditions.

Still other indications for therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. The antibodies of this invention find applicability in administration to individuals at risk of organ or graft rejection.

In another aspect, the invention is a method for diagnosing whether an individual has cancer, comprising determining whether there is expression of transferrin receptor on selected cells from the individual, wherein the expression of transferrin receptor on said cells is indicative of said cancer. In some embodiments, the expression of transferrin receptor is determined using an anti-transferrin receptor antibody. In some embodiments, the method involves detecting the level of transferrin receptor expression from cells. The term "detection" as used herein includes qualitative and/or quantitative detection (measuring levels) with or without reference to a control.

In yet another aspect, the invention is a method of diagnosing cancer in an individual by detecting transferrin receptor on or released from cells from the individual, wherein the cancer is selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurysmal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, uveal or intraocular melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In another aspect, the invention is a method for aiding diagnosis of cancer (such as but not limited to ovarian, lung, prostate, pancreatic, colon, or breast cancer) in an individual comprising determining the expression of transferrin receptor in a biological sample from the individual. In some embodiments, the expression of transferrin receptor is determined using an anti-transferrin receptor antibody. In some embodiments, the method is detecting the level of transferrin receptor expression from cells. The transferrin receptor released from the cancer may contribute to elevated levels of transferrin receptor or a portion thereof, being detectable in body fluids (e.g., blood, salivary or gut mucinous secretions).

In yet another aspect, the invention is a method of treating cancer by administering an effective amount of an antibody that binds to transferrin receptor sufficient to reduce growth of cancerous cells. In some embodiments, the antibody is an anti-transferrin receptor antibody. In certain embodiments, the cancerous cells are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurysmal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, uveal or intraocular melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, colon cancer, prostate cancer, lung cancer, sarcoma, renal metastatic cancer, thyroid metastatic cancer, and clear cell carcinoma.

In yet another aspect, the invention is a method of delaying development of metastasis in an individual having cancer comprising administering an effective amount of at least one of a family of antibodies that bind specifically to transferrin receptor. In one embodiment, the antibody is an anti-transferrin receptor antibody. In another aspect, the invention is a method of inhibiting growth and/or proliferation of cancer cells in vitro or in an individual comprising administering an effective amount of a composition comprising an anti-transferrin receptor antibody associated with (including linked to) a chemotherapeutic agent to the cell culture or sample, or to the individual.

In yet another aspect, the invention is a method of delivering a therapeutic agent to a cancerous cell in an individual by administering to the individual an effective amount of at least one member of a family of antibodies, which bind specifically to transferrin receptor. In other embodiments, an anti-transferrin receptor antibody is delivered to an individual in combination with (including linked to) another therapeutic agent.

In some embodiments, the anti-transferrin receptor antibody is a humanized antibody derived from a named antibody herein (generally, but not necessarily, comprising one or more partial or intact CDRs of the antibody). In some embodiments, the anti-transferrin receptor antibody is a human antibody with one or more properties of the named antibody. In some embodiments, the chemotherapeutic agent (such as a toxin or a radioactive molecule) is delivered into the cancer cells (is internalized). In some embodiments, the agent is saporin.

In another aspect, the invention is a method of treating cancer in an individual comprising administering an effective amount of a composition comprising an anti-transferrin receptor antibody associated with (including linked to) a chemotherapeutic agent to the individual.

The present invention further provides methods for modulating, either by enhancing or reducing, the association of transferrin receptor with a cytoplasmic signaling partner. The association of transferrin receptor with a cytoplasmic signaling partner can be impacted by contacting a transferrin receptor molecule presenting on a cell surface, with an agent that modulates the binding of the signaling partner to transferrin receptor. Agents which block or reduce transferrin receptor association with its binding and/or signaling partners can be used to modulate biological and pathological processes which are involved in transferrin receptor-mediated inflammation or immune responses. Pathological processes involving this action include tumor-associated cell growth.

Agents can be tested for their ability to block, reduce, enhance or otherwise modulate the association of transferrin receptor with a binding partner, such as an anti-transferrin receptor antibody. Specifically, an agent can be tested for the ability to modulate such an interaction by incubating a peptide comprising the transferrin receptor interaction site (typically in its native conformation as it exists on intact living cells) with a binding partner and a test agent, and determining whether the test agent reduces or enhances the binding of the binding partner to the transferrin receptor peptide.

Agonists, antagonists, and other modulators of transferrin receptor function are expressly included within the scope of this invention. These agonists, antagonists and modulators are polypeptides that comprise one or more of the antigenic determinant sites in transferrin receptor, or comprise one or more fragments of such sites, variants of such sites, or peptidomimetics of such sites. These agonistic, antagonistic, and transferrin receptor modulatory compounds are provided in linear or cyclized form, and optionally comprise at least one amino acid residue that is not commonly found in nature or at least one amide isostere. These compounds may be glycosylated. The agonists, antagonists, and other modulators of transferrin receptor function of this invention are desirably used in all of the embodiments and methods described above with reference to antibodies.

Other aspects of this invention relate to the novel epitope of the transferrin receptor identified and referred to herein as the antigen for the LUCA31 antibody. This antigen is suitable for use as an immunogen and for a variety of research, diagnostic and therapeutic purposes.

In certain aspects, the invention is a method for aiding in the diagnosis of disease in an individual comprising the steps of (i) assaying for the presence of transferrin receptor in a blood or tissue sample obtained from an individual; (ii) detecting whether said sample has an increased amount of a transferrin receptor marker relative to a normal (non-diseased) blood or tissue sample; and (iii) correlating an increased amount of said marker to a positive diagnosis or correlating the absence of an increased amount of said marker to a negative diagnosis for disease. In certain embodiments, the marker is detected using an anti-transferrin receptor antibody. In certain embodiments, the method is effected by a technique selected from the group consisting of radionuclide imaging, flow cytometry, and immunohistochemistry.

BRIEF DESCRIPTION OF THE DRAWINGS

FIG. 10A shows FACS analysis of LUCA31 binding to cell lines derived from breast and prostate cancers. Data is plotted as a function of mean fluorescent intensity and EGFR staining is included as a standard. FIG. 10B shows maximum activity of LUCA31 (measured in 0.5% serum) in breast and prostate cancer cell lines. Data values represent the maximum inhibition of cell proliferation observed using a five-point dose titration of antibody between 10 ug/ml and 0.6 ug/ml.

FIG. 11A shows FACS analysis of LUCA31 binding to cell lines derived from hematological cancer lines. FIG. 11B shows maximum activity of LUCA31 (measured in 0.5% serum) in hematological cancer lines.

FIG. 16A shows median tumor volume measurements. FIG. 16B shows mean tumor volume measurements, with error bars. For each experimental group, data is plotted until the first animal presents with a tumor greater than 1000 mm$^3$.

DETAILED DESCRIPTION OF THE INVENTION

Figure 1:
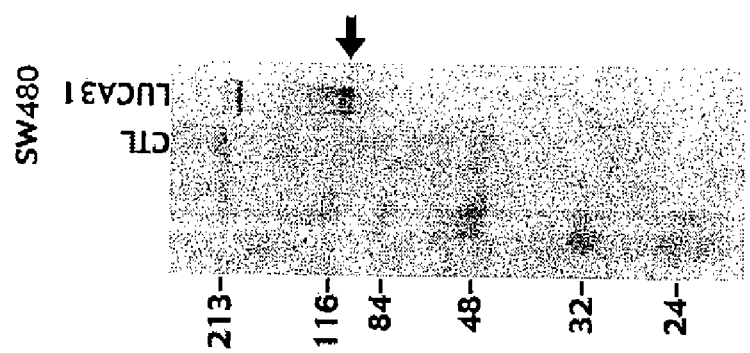
FIG. 1 shows an immunoprecipitation using LUCA31 monoclonal antibody on SW480 cell lysates, followed by a western blot using LUCA31 monoclonal antibody and visualized using ECL+ detection system (Amersham).

The invention provides a novel epitope of the human transferrin receptor (referred to herein as the LUCA31 epitope), which is expressed on cancerous cells of various tissue types, including but not limited to breast, colon, lung, and prostate cancers. Further, the invention provides monoclonal antibodies and polypeptides that bind to this transferring receptor epitope and methods making and using these antibodies and polypeptides to diagnose and treat various diseases human cancers associated with expression and/or over-expression of transferrin receptor.

One issue that has been raised with previous transferrin receptor antibodies arises from the relatively widespread profile of tissue distribution of the epitope to which these antibodies bind. The present invention relates to an antibody, herein sometimes referred to as the LUCA31 antibody, that has robust anti-proliferative activity in many solid tumor cell lines. The LUCA31 antibody has been found to bind to an epitope on the human transferrin receptor that shows a unique and more limited normal tissue distribution than other transferrin receptor antibodies. Staining of brain endothelium, a tissue normally enriched in transferrin receptor (see e.g., Jefferies et al., *Transferrin receptor on endothelium of brain capillaries*, Nature 312, 162-163 (1984); Orte, et al., *A comparison of blood-brain barrier and blood-nerve barrier endothelial cell markers*, Anat Embryol 199, 509-517 (1999); Rothenberger et al., *Coincident expression and distribution of melanotransferrin and transferrin receptor in human brain capillary endothelium*, Brain Res 712, 117-121 (1996)), shows very limited reactivity with LUCA31. The pancreas, including islet cells, has been shown to stain positively with transferrin receptor antibodies (Gatter, 1983), but we have seen limited pancreatic tissue staining with LUCA31. Additionally, published data shows transferrin receptor is present in both Kupfer cells and hepatocytes within the liver (Gatter, 1983), however analyses with LUCA31 did not show liver tissue staining. Taken together, the robust activity and unique tissue distribution profile of the LUCA31 epitope provides rationale that LUCA31 and related antibodies are distinct from other transferrin receptor antibodies and may provide a significant therapeutic and commercial advantage.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty, ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

"Transferrin receptor" refers to that polypeptide antigen with a molecular weight of approximately 90 kD to 100 kD against which the antibodies of the present invention are directed. The transferrin receptor is a cell surface protein bound by anti-transferrin receptor antibodies and present on several normal tissues including colon and duodenum and several types of carcinomas. This antigen may have more than one different epitope. The novel epitope of the human transferrin receptor to which the antibody LUCA31 binds is referred to herein as the LUCA31 epitope, and is of particular interest in this invention. It is currently believed that transferrin receptor, and the LUCA31 epitope, may be over-expressed in certain cancer cells in comparison to their normal tissue counterparts. In certain embodiments, references generally to characteristics of the transferrin receptor are intended to refer specifically Agonists, antagonists, and other modulators of transferrin receptor function are expressly included within the scope of this invention. These agonists, antagonists and modulators are polypeptides that comprise one or more of the antigenic determinant sites in transferrin receptor, or comprise one or more fragments of such sites, variants of such sites, or peptidomimetics of such sites. These agonistic, antagonistic, and transferrin receptor modulatory compounds are provided in linear or cyclized form, and optionally comprise at least one amino acid residue that is not commonly found in nature or at least one amide isostere. These compounds may be glycosylated.

More specifically, the term "transferrin receptor modulator" as used herein is defined as any compound that (1) is capable of disrupting or blocking the interaction between human transferrin receptor and its native ligands or an anti-transferrin receptor antibody; (2) is capable of binding to human transferrin receptor and its native ligands or an anti-transferrin receptor antibody; (3) contains an antigenic site that can be used in the raising of antibodies capable of binding to human transferrin receptor and its native ligands or an anti-transferrin receptor antibody; (4) contains an antigenic site that can be used in the screening of antibodies capable of binding to human transferrin receptor and its native ligands or an anti-transferrin receptor antibody; (5) contains an antigenic site that an be used in the raising of antibodies capable of disrupting or blocking the interaction between human transferrin receptor and its native ligands or an anti-transferrin receptor antibody; (6) contains an antigenic site that can be used in the screening of antibodies capable of disrupting or blocking the interaction between human transferrin receptor and its native ligands or an anti-transferrin receptor antibody. transferrin receptor modulators may be "transferrin receptor agonists" or "transferrin receptor antagonists" depending on whether their activity enhances or inhibits normal transferrin receptor biological activity, respectively.

Transferrin receptor agonists, antagonists and modulators include transferrin receptor variants, transferrin receptor peptide antagonists, peptidomimetics, and small molecules, anti-transferrin receptor antibodies and immunoglobulin variants, amino acid variants of human transferrin receptor including amino acid substitution, deletion, and addition variants, or any combination thereof, and chimeric immunoglobulins. The transferrin receptor agonists, antagonists and modulators of this invention are based on the inventors' identification of the transferrin receptor domains involved in the binding of human transferrin receptor to its native ligands or anti-transferrin receptor antibodies. Thus, the invention provides transferrin receptor agonists, antagonists and modulators with molecular structures that duplicate or mimic one or more of the anti-transferrin receptor binding domains of human transferrin receptor.

As used herein, the term "transferrin receptor variant" denotes any amino acid variant of human transferrin receptor, including amino acid substitution, deletion, and addition variants, or any combination thereof. The definition encompasses chimeric molecules such as human transferrin receptor/non-human chimeras and other hybrid molecules. Also included in the definition is any fragment of a transferrin receptor variant molecule that comprises the variant or hybrid region(s) of the molecule.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody".

"Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al., (1989) Proc Natl Acad Sci USA 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856. Riechmann, L., et al., (1988) Nature 332:323-327; Verhoeyen, M., et al., (1988) Science 239:1534-1536; Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a transferrin receptor epitope is an antibody that binds this transferrin receptor epitope with greater affinity, avidity, more readily, and/or with greater duration than it binds to other transferrin receptor epitopes or non-transferrin receptor epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "immunologically active" in reference to an epitope being or "remaining immunologically active" refers to the ability of an antibody (e.g., anti-transferrin receptor antibody) to bind to the epitope under different conditions, for example, after the epitope has been subjected to reducing and denaturing conditions.

Different biological functions are associated with anti-transferrin receptor antibodies, including, but not limited to, ability to bind to transferrin receptor (including transferrin receptor on cancer cells, including but not limited to ovarian, prostate, pancreatic, lung, colon, or breast cancer cells); ability to bind to a portion of transferrin receptor that is exposed on the surface of a living cell in vitro or in vivo; ability to deliver a chemotherapeutic agent to cancerous cells (such as ovarian, prostate, pancreatic, lung, colon, or breast cancer cells) expressing transferrin receptor; ability to deliver a therapeutic agent or detectable marker into cancer cells expressing transferrin receptor. As discussed herein, polypeptides (including antibodies) of the invention may have any one or more of these characteristics.

An "anti-transferrin receptor equivalent antibody" or "anti-transferrin receptor equivalent polypeptide" refers to an antibody or a polypeptide having one or more biological functions associated with an anti-transferrin receptor antibody, such as, for example binding specificity.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, an agent is said to be randomly selected when the agent is chosen randomly without considering the specific sequences involved in the association of transferrin receptor with its native binding partners or known antibodies. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. With respect to anti-transferrin receptor agents, it is currently believed that there are at least three epitopes on transferrin receptor against which antibodies can be raised and therefore at least three sites of action for agents that block transferrin receptor/anti-transferrin receptor interaction. This invention also encompasses agents that act at the sites of interaction between transferrin receptor and its native binding partner, although other ligands and their active transferrin receptor-interactive sites are also encompassed within the scope of this invention, whether currently known or later identified. Agents can be rationally selected or rationally designed by utilizing the peptide sequences that make up the contact sites of the receptor/ligand and/or transferrin receptor/anti-transferrin receptor antibody complex. For example, a rationally selected peptide agent can be a peptide whose amino acid sequence is identical to an epitope appearing on transferrin receptor as it is exposed on the surface of a living cell in its native environment. Such an agent will reduce or block the association of the anti-transferrin receptor antibody with transferrin receptor, or the association of transferrin receptor with its native ligand, as desired, by binding to the anti-transferrin receptor antibody or to the native ligand.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE)) to the antibody, as well as indirect labeling of the probe or antibody by reactivity with a detectable substance.

As used herein, the term "association", with regard to the antibody, includes covalent and non-covalent attachment or binding to an agent (e.g., chemotherapeutic agent). The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

A "biological sample" encompasses a variety of sample types obtained from an individual and can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

An "effective amount" of a pharmaceutical composition, in one embodiment, is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages comprise 0.1- to 100 mg/kg/body weight. The preferred dosages comprise 1- to 100-mg/kg/body weight. The most preferred dosages comprise 10- to 100-mg/kg/body weight.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. from its original source.

An "individual" is a vertebrate, preferably a mammal, more preferably a human. Mammals include, but are not limited to, farm animals, sport animals, pets, primates, mice and rats.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

Also encompassed within the scope of the invention are peptidomimetics of the transferrin receptor peptide agonists, antagonists and modulators (including anti-transferrin receptor antibodies) described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(.dbd.O)—NH—) in a transferrin receptor peptide agonist, antagonist or modulators with an amide isostere. Suitable amide isosteres include —CH.sub.2-NH—, —CH.sub.2-S—, —CH.sub.2-S(O).sub.n- (where n is 1 or 2), —CH.sub.2-CH.sub.2-, —CH.dbd.CH— (E or Z), —C(.dbd.O)—CH.sub.2-, —CH(CN)—NH—, —C(OH)—CH.sub.2-, and —O—C(.dbd.O)—NH—. The amide bonds in a transferrin receptor peptide agonist, antagonist or modulator that are suitable candidates for replacement with amide isosteres include bonds that are hydrolyzable by the endogenous esterases or proteases of the intended subject of transferrin receptor peptide agonist, antagonist or modulator treatment.

As used herein, "substantially pure" refers to material that is at least 50% pure (i.e., free from contaminants), more preferably at least 90% pure, more preferably at least 95% pure, more preferably at least 98% pure, more preferably at least 99% pure, or greater, pure.

"Toxin" refers to any substance, which effects an adverse response within a cell. For example, a toxin directed to a cancerous cell would have an adverse, sometimes deleterious effect, on the cancerous cell. Examples of toxins include, but are not limited to, radioisotopes, calicheamicin, and maytansinoids.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

III. Methods of Making Antibodies and Polypeptides

Methods of making monoclonal antibodies are known in the art. One method which may be employed is the method of Kohler and Milstein, Nature 256:495-497 (1975) or a modification thereof. Typically, monoclonal antibodies are developed in non-human species, such as mice. In general, a mouse or rat is used for immunization but other animals may also be used. The antibodies are produced by immunizing mice with an immunogenic amount of cells, cell extracts, or protein preparations that contain human transferrin receptor. The immunogen can be, but is not limited to, primary cells, cultured cell lines, cancerous cells, nucleic acids, or tissue. In one embodiment, cultured human tumor cell lines are used. In another embodiment, human bladder or pancreatic progenitor cells are used. Cells used for immunization, for example, human fetal kidney, bladder cells or human pancreatic progenitor cells, may be cultured for a period of time (at least 24 hours) prior to their use as an immunogen. Cells (e.g., human fetal kidney, bladder cells or human pancreatic progenitor cells) may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture the human fetal kidney or other cells and therefore is discouraged. The immunogen may be administered multiple times at periodic intervals such as, bi-weekly, or weekly, or may be administered in such a way as to maintain viability in the animal (e.g., in a tissue recombinant). Example 2 describes methods used to generate anti-transferrin receptor antibodies and may be used to generate other monoclonal antibodies, which bind to transferrin receptor.

In one embodiment, monoclonal antibodies, which bind to transferrin receptor are obtained by using host cells that overexpress transferrin receptor as an immunogen. Such cells include, by way of example and not by limitation, human fetal kidney cells and human colon cancer cells.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen (e.g., surface of the human fetal kidney cells, surface of cancer cell lines, Ag-transferrin receptor, fetal bladder sections, etc.) using FACS or immunohistochemistry (IHC screening). The selected monoclonal antibody-secreting hybridomas are then cultured either in vitro (e.g., in tissue culture bottles or hollow fiber reactors), or in vivo (e.g., as ascites in mice). Example 3 provides further details about the methods utilized to obtain and screen an anti-transferrin receptor antibody.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, monoclonal antibody anti-LUCA31 and any other equivalent antibodies can be sequenced and produced recombinantly by any means known in the art (e.g., humanization, use of transgenic mice to produce fully human antibodies, phage display technology, etc.). In one embodiment, anti-transferrin receptor monoclonal antibody is sequenced and the polynucleotide sequence is then cloned into a vector for expression or propagation. The sequence encoding the antibody of interest may be maintained in a vector in a host cell and the host cell can then be expanded and frozen for future use.

Example 4 shows the nucleic acid and corresponding translated protein sequence of the kappa light chain of the anti-transferrin receptor monoclonal antibody LUCA31 including the native signal sequence.

Example 4 also shows the nucleic acid and corresponding translated protein sequence of the G1 heavy chain of the anti-transferrin receptor monoclonal antibody LUCA31.

The polynucleotide sequence of monoclonal antibody LUCA31 and any other equivalent antibodies may be used for genetic manipulation to generate a "humanized" antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J. Immunol.* 138: 4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al., *Nucl. Acids Res.*, 19:2471-2476 (1991) and in U.S. Pat. Nos. 6,180,377; 6,054,297; 5,997,867; and 5,866, 692.

The invention also encompasses single chain variable region fragments ("scFv") of antibodies of this invention, such as LUCA31. Single chain variable region fragments are made by linking light and/or heavy chain variable regions by using a short linking peptide. Bird et al. (1988) Science 242: 423-426 describes example of linking peptides which bridge approximately 3.5 nm between the carboxy terminus of one variable region and the amino terminus of the other variable region. Linkers of other sequences have been designed and used, Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to transferrin receptor agonists, antagonists, modulators and antibodies, including functionally equivalent antibodies and polypeptides that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/ isoleucine/leucine; asparagine/glutamine; aspartic acid/ glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a hybridoma deposited with the ATCC as described herein. For purposes of this invention, an antibody fusion protein contains one or more anti-transferrin receptor polypeptides and another amino acid sequence to which it is not attached in the native molecule, for example, a heterologous sequence or a homologous sequence from another region.

An anti-transferrin receptor polypeptide, and other transferrin receptor agonists, antagonists and modulators can be created by methods known in the art, for example, synthetically or recombinantly. One method of producing transferrin receptor peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see Kelley, R. F. & Winkler, M. E. in Genetic Engineering Principles and Methods, Setlow, J. K., ed., Plenum Press, N.Y., vol. 12, pp 1-19 (1990); Stewart, J. M. & Young, J. D. Solid Phase Peptide Synthesis Pierce Chemical Co. Rockford, Ill. (1984); see also U.S. Pat. Nos. 4,105,603; 3,972,859; 3,842,067; and 3,862,925).

Polypeptides of the invention may be conveniently prepared using solid phase peptide synthesis (Merrifield, J. Am. Chem. Soc., 85:2149 (1964); Houghten, Proc. Natl. Acad. Sci. USA 82:5132 (1985)).

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Methods for expressing antibodies recombinantly in plants or milk have been disclosed. See, for example, Peeters, et al. (2001) *Vaccine* 19:2756; Lonberg, N. and D. Huszar (1995) *Int. Rev. Immunol* 13:65; and Pollock, et al. (1999) *J Immunol Methods* 231:147. Methods for making derivatives of antibodies, e.g., humanized, single chain, etc. are known in the art. In another alternative, antibodies may be made recombinantly by phage display technology. See, for example, U.S. Pat. Nos. 5,565,332; 5,580,717; 5,733,743; 6,265,150; and Winter et al., *Annu. Rev. Immunol.* 12:433-455 (1994).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified transferrin receptor or portions thereof for cells expressing the antibody or protein of interest. The "panning" procedure is conducted by obtaining a cDNA library from tissues or cells that express the antibody or protein of interest, over-expressing the cDNAs in a second cell type, and screening the transfected cells of the second cell type for a specific binding to transferrin receptor. Detailed descriptions of the methods used in cloning mammalian genes coding for cell surface proteins by "panning" can be found in the art. See, for example, Aruffo, A. and Seed, B. *Proc. Natl. Acad. Sci. USA,* 84, 8573-8577 (1987) and Stephan, J. et al., *Endocrinology* 140: 5841-5854 (1999).

cDNAs encoding anti-transferrin receptor antibodies, and other transferrin receptor peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to transferrin receptor is effected by an immunoassay or FACS. A cell over-expressing the antibody or protein of interest can be identified.

Various techniques are also available which may now be employed to produce mutant transferrin receptor peptide agonists, antagonists, and modulators which encodes for additions, deletions, or changes in amino acid sequence of the resultant protein relative to the parent transferrin receptor peptide agonist, antagonist or modulator molecule.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-transferrin receptor polypeptide could be produced by an automated polypeptide synthesizer employing the solid phase method.

IV. Methods for Screening Polypeptides and Monoclonal Antibodies

Several methods may be used to screen polypeptides and monoclonal antibodies that bind to transferrin receptor. It is understood that "binding" refers to biologically or immunologically relevant binding, i.e., binding which is specific for the unique antigen for which the immunoglobulin molecule is encoded, or to which the polypeptide is directed. It does not refer to non-specific binding that may occur when an immunoglobulin is used at a very high concentration against a non-specific target. In one embodiment, monoclonal antibodies are screened for binding to transferrin receptor using standard screening techniques. In this manner, anti-transferrin receptor monoclonal antibody was obtained. In accordance with the Budapest Treaty, a hybridoma which produces anti-transferrin receptor monoclonal antibodies has been deposited in the American Type Culture Collection (ATCC) 10801 University Blvd., Manassas Va. 20110-2209 on 8 Jul. 2004 with a Patent Deposit Designation of PTA-6055.

Monoclonal antibodies that bind to transferrin receptor are screened for binding to cancerous tissues and non-cancerous cells. In one embodiment, monoclonal antibodies which bind to transferrin receptor and that are also cross reactive to human cancerous cells or tissues, but not to normal cells or tissues to the same degree, are selected. One method that may be employed for screening is immunohistochemistry (IHC). Standard immunohistochemical techniques are known to those of average skill in the art. See, for example, *Animal Cell Culture Methods* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if transferrin receptor is present only on cancerous cells, anti-transferrin receptor antibodies may be used to detect the presence of transferrin receptor on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining. Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include but are not limited to carcinomas, adenocarcinomas, sarcomas, adenosarcomas, lymphomas, and leukemias.

In yet another alternative, cancerous cells lines such as BT474 (ATCC# HTB-20), MCF7 (ATCC# HTB-22), MDA-175 (ATCC# HB-25), MDA-361 (ATCC# HB-27), SK-BR-3 (ATCC# HTB-30), A549 (ATCC# CCL-185), CaLu3 (ATCC# HTB-55) SKMES1 (ATCC# HTB-58), ES-2 (ATCC# CRL-1978), SKOV3 (ATCC# HTB-77), AsPC-1 (ATCC# CRL-1682), HPAFII (ATCC# CRL-1997), Hs700T (ATCC# HTB-147), Colo205 (ATCC# CCL-222), HT29 (ATCC# HTB-38), SW480 (ATCC# CCL-228), SW948 (ATCC# CCL-237), 293 (ATCC# CRL-1573), 786-O (ATCC# CRL-1932), A498 (ATCC# HTB-44), Caki2 (ATCC# HTB-47), Cos7 (ATCC# CRL-1651), RL65 (ATCC# CRL-10345), SVT2 (ATCC# CCL-163.1), 22Rv1 (ATCC# CRL 2505), DU145 (ATCC# HTB-81), LNCaP (ATCC# CRL-1740), PC3 (ATCC# CRL-1435), Hs746T (ATCC# HTB 135), TDH-1 (proprietary prostate cancer cell line developed at Raven biotechnologies, inc.) Rav CA130 (proprietary lung cancer line developed at Raven biotechnologies, inc.), Rav9979 (proprietary lung cancer cell line developed at Raven biotechnologies, inc.), Rav9926 (proprietary pancreatic cancer cell line developed at Raven biotechnologies, inc.), and NCI-N87 (ATCC# CRL-5822) and normal cells from their respective tissues may be used to screen for monoclonal antibodies that are specific for cancerous tissue. Primary, or low passage, cell cultures derived from normal tissues from different organs, including but not limited to, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in WO 01/43869, and screened for the binding of antibody using IHC as described above for tissues. Alternatively, cells may be removed from the growth surface using non-proteolytic means and spun into a pellet, which is then embedded and treated as tissues for IHC analysis as described above. Cells may be inoculated into immunodeficient animals, a tumor allowed to grow, and then this tumor may be harvested, embedded, and used as a tissue source for IHC analysis. In another alternative, single cells may be screened by incubating with the primary antibody, a secondary "reporter" antibody linked to a fluorescent molecule and then analyzed using a fluorescent activated cell-sorting (FACS) machine.

Several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA. PolyMICA (polyclonal Mirror Image Complementary Antibodies) technique, described by D. C. Mangham and P. G. Isaacson (*Histopathology* (1999) 35 (2):129-33), can be used to test binding of primary antibodies (e.g., anti-transferrin receptor antibodies) to normal and cancerous tissue. Several kinds of PolyMICA™ Detection kits are commercially available from The Binding Site Limited (P.O. Box 4073 Birmingham B29 6AT England). Product No. HK004.D is a PolyMICA™ Detection kit which uses DAB chromagen. Product No. HK004.A is a PolyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., anti-transferrin receptor antibodies) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

V. Methods of Characterizing Anti-Transferrin Receptor Antibodies

Several methods can be used to characterize anti-transferrin receptor antibodies. One method is to identify the epitope to which it binds. Epitope mapping is commercially available from various sources, for example, Pepscan Systems (Edelhertweg 15, 8219 PH Lelystad, The Netherlands). Epitope mapping can be used to determine the sequence to which an anti-transferrin receptor antibody binds. The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with anti-transferrin receptor antibody. The epitope to which anti-transferrin receptor antibody binds can be determined in a systematic screening by using overlapping peptides derived from the extracellular sequence and determining binding by anti-transferrin receptor antibody.

Yet another method that can be used to characterize an anti-transferrin receptor antibody is to use competition assays with other antibodies known to bind to the same antigen, i.e., transferrin receptor to determine if anti-transferrin receptor antibodies binds to the same epitope as other antibodies. Examples of commercially available antibodies to transferrin receptor may be available and may be identified using the binding assays taught herein. Competition assays are well known to those of skill in the art, and such procedures and illustrative data are detailed further in the Examples. Anti-transferrin receptor antibodies can be further characterized by the tissues, type of cancer or type of tumor to which they bind.

Another method of characterizing anti-transferrin receptor antibodies is by the antigen to which it binds. Anti-transferrin receptor antibodies were used in Western blots with cell lysates from various human cancers. As is known to one of skill in the art, Western blotting can involve running cell lysates and/or cell fractions on a denaturing or non-denaturing gel, transferring the proteins to nitrocellulose paper, and then probing the blot with an antibody (e.g., anti-transferrin receptor antibody) to see which proteins are bound by the antibody. This procedure is detailed further in the Examples. The band to which anti-transferrin receptor antibody bound was isolated and further analyzed using mass spectroscopy. The antigen to which anti-transferrin receptor antibody binds was found to be transferrin receptor. Transferrin receptor is associated with various human cancers of different tissues including but not limited to colon, lung, breast, prostate, ovary, pancreas, kidney as well as other types of cancer such as sarcoma. Further description of transferrin receptor is given in the Examples below.

VI. Methods of Diagnosing Cancer Using Anti-Transferrin Receptor Antibodies and Transferrin Receptor Modulators Monoclonal antibodies to transferrin receptor made by the methods disclosed herein maybe used to identify the presence or absence of cancerous cells in a variety of tissues, including but not limited to, ovary, breast, lung, prostate, colon, kidney, pancreas, skin, thyroid, brain, heart, liver, stomach, nerve, blood vessels, bone, and upper digestive tract, for purposes of diagnosis. Monoclonal antibodies to transferrin receptor made by the methods disclosed herein may also be used to identify the presence or absence of cancerous cells, or the level thereof, which are circulating in blood after their release from a solid tumor. Such circulating antigen may be an intact transferrin receptor antigen, or a fragment thereof that retains the ability to be detected according to the methods taught herein. Such detection may be effected by FACS analysis using standard methods commonly used in the art.

These uses can involve the formation of a complex between transferrin receptor and an antibody that binds specifically to transferrin receptor. Examples of such antibodies include but are not limited to those anti-transferrin receptor monoclonal antibodies produced by the hybridoma deposited in the ATCC with the designation PTA-6055. The formation of such a complex can be in vitro or in vivo. Without being bound by theory, monoclonal antibody anti-transferrin receptor can bind to transferrin receptor through the extracellular domain of transferrin receptor and may then be internalized.

In a preferred embodiment of the diagnostic methods of this invention, the antibody bears a detectable label. Examples of labels that may be used include a radioactive agent or a fluorophore, such as fluoroisothiocyanate or phycoerythrin.

As with other known antibodies used commercially for diagnostic and therapeutic purposes, the target antigen of this invention is broadly expressed in normal tissue. It is also up regulated in some tumors. Therefore, the particular dosages and routes of delivery of the antibodies of this invention as used for diagnostic or therapeutic agents will be tailored to the particular tumor or disease state at hand, as well as to the particular individual being treated.

One method of using the antibodies for diagnosis is in vivo tumor imaging by linking the antibody to a radioactive or radioopaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of transferrin receptor are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumors or neoplasms, or of measuring the effectiveness of a method of treatment with a radiolabelled antibody, comprising the step of administering a radiolabelled, tumor-specific antibody to an individual following the practice of this invention. The radiolabelled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labelled with therapeutic radionuclides such as Iodine-131, Rhenium-188, Holmium-166, Samarium-153 and Scandium-47, which do not compromise the immunoreactivity of antibodies and are not broken down in vivo, are especially preferred. The person skilled in the art will appreciate that other radioactive isotopes are known, and may be suitable for specific applications. The radioimaging may be conducted using Single Photon Emission Computer Tomography (SPECT), Position Emission Tomography (PET), Computer Tomography (CT) or Magnetic Resonance Imaging (MRI). Correlative imaging, which permits greater anatomical definition of location of metastases located by radioimmunoimaging, is also contemplated.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify cancerous cells at different stages of development. The antibodies may also be used to determine which individuals' tumors express the antigen on their surface at a pre-determined level and are thus candidates for immunotherapy using antibodies directed against said antigen. The antibodies may recognize both primary and metastasizing cancers of the ovary, prostate and pancreas and primary cancers of the lung that express transferrin receptor. As used herein, detection may include qualitative and/or quantitative detection and may include comparing the level measured to a normal cell for an increased level of expression of transferrin receptor in cancerous cells.

The invention also provides methods of aiding diagnosis of cancer (such as ovarian, lung, pancreatic, prostate, colon, or breast cancer) in an individual using any antibody that binds to transferrin receptor and any other methods that can be used determine the level of transferrin receptor expression. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of cancer can comprise the step of detecting the level of transferrin receptor in a biological sample from the individual and/or determining the level of transferrin receptor expression in the sample. Antibodies recognizing the antigen or a portion thereof may also be used to create diagnostic immunoassays for detecting antigen released or secreted from living or dying cancer cells in bodily fluids, including but not limited to, blood, saliva, urine, pulmonary fluid, or ascites fluid.

Not all cells in a particular tumor of interest will express transferrin receptor, and cancerous cells in other tissues may express transferrin receptor, thus an individual should be screened for the presence or absence of transferrin receptor on cancerous cells to determine the usefulness of immunotherapy in the individual. The anti-transferrin receptor antibodies made by the methods disclosed herein may be used to determine whether an individual diagnosed with cancer may be deemed a candidate for immunotherapy using antibodies directed against transferrin receptor. In one embodiment, a cancerous tumor or a biopsy sample may be tested for expression of transferrin receptor, using antibodies directed against transferrin receptor. Individuals with cancer cells that express transferrin receptor are suitable candidates for immunotherapy using antibodies directed against transferrin receptor. Staining with anti-transferrin receptor antibody may also be used to distinguish cancerous tissues from normal tissues.

Methods of using anti-transferrin receptor antibodies for diagnostic purposes are useful both before and after any form of anti-cancer treatment, e.g., chemotherapy or radiation therapy, to determine which tumors are most likely to respond to a given treatment, prognosis for individual with cancer, tumor subtype or origin of metastatic disease, and progression of the disease or response to treatment.

The compositions of this invention are also suitable for diagnosis of disease states other than cancer, using the methods generally described above in application with other diseased (non-cancerous) cells. Disease states suitable for use in the methods of this invention include, but are not limited to, diseases or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Uses described anywhere in this application that recite their use for anti-transferrin receptor antibodies also encompass the use of other transferrin receptor agonists, antagonists and modulators as described herein. In such embodiments, the transferrin receptor agonists, antagonist or other non-antibody modulator is substituted for the transferrin receptor antibody in the steps described, and alterations within the scope of the ordinarily skilled practitioner are made to tailor the method to the substituted transferrin receptor modulatory composition.

VII. Compositions of this Invention

This invention also encompasses compositions, including pharmaceutical compositions, comprising anti-transferrin receptor antibodies, polypeptides derived from anti-transferrin receptor antibodies, polynucleotides comprising sequence encoding anti-transferrin receptor antibodies, and other agents as described herein. As used herein, compositions further comprises one or more antibodies, polypeptides and/or proteins that bind to transferrin receptor, transferrin receptor agonists, antagonists, modulators, and/or one or more polynucleotides comprising sequences encoding one or more antibodies, polypeptides and proteins that bind to transferrin receptor.

The invention further provides for conjugates of any transferrin receptor peptide agonist, antagonist or modulator, and additional chemical structures that support the intended function or functions of the particular transferrin receptor peptide agonist, antagonist or modulator. These conjugates include transferrin receptor peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (eds) Affinity Chromatography: A Practical Approach, IRL Press (1985); Lowe, "An Introduction to Affinity Chromatography", in Work et al. (eds) Laboratory Techniques in Biochemistry and Molecular Biology, Vol. 7, Part II, North-Holland (1979); Porath et al., "Biospecific Affinity Chromatography", in Neurath et al. (eds), The Proteins, 3rd ed., Vol. 1, pp. 95-178 (1975); and Schott, Affinity Chromatography, Dekker (1984).

Also provided herein are conjugates of transferrin receptor peptide agonist, antagonist or modulator and any reporter moiety used in the diagnostic procedures discussed herein.

The transferrin receptor peptide agonist, antagonist or modulator agents, polypeptides and proteins of this invention, including anti-transferrin receptor antibodies, are further identified and characterized by any (one or more) of the following criteria: (a) ability to bind to transferrin receptor (including transferrin receptor on cancer cells, including but not limited to ovarian, prostate, pancreatic, lung, colon, or breast cancer cells); (b) ability to competitively inhibits preferential binding of a known anti-transferrin receptor antibody to transferrin receptor, including the ability to preferentially bind to the same transferrin receptor epitope to which the original antibody preferentially binds; (c) ability to bind to a portion of transferrin receptor that is exposed on the surface of a living cell in vitro or in vivo; (d) ability to bind to a portion of transferrin receptor that is exposed on the surface of living cancer cells, such as but not limited to ovarian, prostate, pancreatic, lung, colon, or breast cancer cells; (e) ability to deliver a chemotherapeutic agent or detectable marker to cancerous cells (such as but not limited to ovarian, prostate, pancreatic, lung, colon, or breast cancer cells) expressing transferrin receptor; (f) ability to deliver a therapeutic agent into cancerous cells (such as but not limited to ovarian cancer cells) expressing transferrin receptor.

In some embodiments, the antibody of the invention is an antibody that is produced by a host cell with a deposit number of ATCC No. PTA-6055, or progeny thereof. The present invention also encompasses various formulations of antibodies produced by these deposited hybridomas and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of any of these or equivalent antibodies that comprises an antigen (transferrin receptor), recognition site of the required specificity. The invention also provides human antibodies displaying one or more of the biological characteristics of an anti-transferrin receptor family member. The equivalent antibodies of the anti-transferrin receptor family (including humanized antibodies and human antibodies), polypeptide fragments, and polypeptides comprising any of these fragments are identified and characterized by any (one or more) of the five criteria described above.

In some embodiments, the antibodies, polypeptides and proteins of the invention that bind to transferrin receptor are antibodies, polypeptides and proteins that competitively inhibit preferential binding of a herein-specified anti-transferrin receptor antibody to transferrin receptor. In some embodiments, the antibodies, the polypeptides and the proteins preferentially bind to the same epitope on transferrin receptor as the antibody LUCA31 preferentially binds.

Accordingly, the invention provides any of the following (or compositions, including pharmaceutical compositions, comprising any of the following): (a) an antibody produced by the host cell with a deposit number identified above or its progeny; (b) a humanized form of such an antibody; (c) an antibody comprising one or more of the light chain and/or heavy chain variable regions of such an antibody; (d) a chimeric antibody comprising variable regions homologous or derived from variable regions of a heavy chain and a light chain of such an antibody, and constant regions homologous or derived from constant regions of a heavy chain and a light chain of a human antibody; (e) an antibody comprising one or more of the light chain and/or heavy chain CDRs (at least one, two, three, four, five, or six) of such an antibody; (f) an antibody comprising a heavy and/or a light chain of such an antibody; (g) a human antibody that is equivalent to such an antibody. A humanized form of the antibody may or may not have CDRs identical to that original antibody, or antibody produced by a host cell with a deposit number identified above. Determination of CDR regions is well within the skill of the art. In some embodiments, the invention provides an antibody which comprises at least one CDR that is substantially homologous to at least one CDR, at least two, at least three, at least four, at least 5 CDRs of an antibody produced by one of the above-identified deposited hybridomas (or, in some embodiments substantially homologous to all 6 CDRs of one of these antibodies, or derived from one of these antibodies), or antibody produced by the host cell with a deposit number identified above. Other embodiments include antibodies that have at least two, three, four, five, or six CDR(s) that are substantially homologous to at least two, three, four, five or six CDRs of an antibody produced from a hybridoma deposited as identified herein, or derived from such an antibody. It is understood that, for purposes of this invention, binding specificity and/or overall activity (which may be in terms of delivering a chemotherapeutic agent to or into cancerous cells to reduce the growth and/or proliferation of cancer cells, to induce apoptotic cell death in the cancer cell, to delay the development of metastasis, and/or treating palliatively) is generally retained, although the extent of activity may vary compared to an antibody produced by a deposited hybridoma (may be greater or lesser). The invention also provides methods of making any of these antibodies. Methods of making antibodies are known in the art and are described herein.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

In some embodiments of this invention, cells of this invention that express transferrin receptor, a portion of transferrin receptor, anti-transferrin receptor antibodies or other transferrin receptor-binding polypeptides of this invention are administered directly to an individual to modulate their in vivo transferrin receptor biological activity.

VIII. Methods of Using Transferrin Receptor Modulators and Anti-Transferrin Receptor Antibodies for Therapeutic Purposes Monoclonal antibodies to transferrin receptor may be used for therapeutic purposes in individuals with cancer or other diseases. Therapy with anti-transferrin receptor antibodies can involve formation of complexes both in vitro and in vivo as described above. In one embodiment, monoclonal antibody anti-transferrin receptor can bind to and reduce the proliferation of cancerous cells. It is understood that the antibody is administered at a concentration that promotes binding at physiological (e.g., in vivo) conditions. In another embodiment, monoclonal antibodies to transferrin receptor can be used for immunotherapy directed at cancerous cells of different tissues such as colon, lung, breast, prostate, ovary, pancreas, kidney and other types of cancer such as sarcoma. In another embodiment, monoclonal antibody anti-transferrin receptor alone can bind to and reduce cell division in the cancer cell. In another embodiment, monoclonal antibody anti-transferrin receptor can bind to cancerous cells and delay the development of metastasis. In yet another embodiment, an individual with cancer is given palliative treatment with anti-transferrin receptor antibody. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

In such situations, the anti-transferrin receptor antibody may be administered with agents that can enhance or direct an individual's own immune response, such as an agent that strengthens ADCC.

In yet another embodiment, anti-transferrin receptor antibody be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, the anti-transferrin receptor antibody is internalized by the cell bearing transferrin receptor at its surface, thus delivering the conjugated moiety to the cell to induce the therapeutic effect. In yet another embodiment, the antibody can be employed as adjuvant therapy at the time of the surgical removal of a cancer expressing the antigen in order to delay the development of metastasis. The antibody can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

Cell cycle dosing is contemplated in the practice of this invention. In such embodiments, a chemotherapeutic agent is used to synchronize the cell cycle of the tumor or other target diseased cells at a pre-determined stage. Subsequently, administration of the anti-transferrin receptor antibody of this invention (alone or with an additional therapeutic moiety) is made. In alternative embodiments, an anti-transferrin receptor antibody is used to synchronize the cell cycle and reduce cell division prior to administration of a second round of treatment; the second round may be administration of an anti-transferrin receptor antibody and/or an additional therapeutic moiety.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Dacarbazine, dactinomycin (formerly actinomycin), daunirubicin HCl, daunorucbicin citrate, denileukin diftitox, Dexrazoxane, Dibromomannitol, dihydroxy anthracin dione, Docetaxel, dolasetron mesylate, doxorubicin HCl, dronabinol, *E. coli* L-asparaginase, emetine, epoetin alfa, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon alfa-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptipurine, mesna, methotrexate, methyltestosterone, mithramycin, mitomycin C, mitotane, mitoxantrone, nilutamide, octreotide acetate, ondansetron HCl, paclitaxel, pamidronate disodium, pentostatin, pilocarpine HCl, plimycin, polifeprosan 20 with carmustine implant, porfimer sodium, procaine, procarbazine HCl, propranolol, rituximab, sargramostim, streptozotocin, tamoxifen, taxol, teniposide, tenoposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

In a preferred embodiment, the cytotoxin is especially effective in dividing or rapidly dividing cells, such that non-dividing cells are relatively spared from the toxic effects.

The antibodies of the invention can be internalized within the diseased or carcinoma cells to which they bind and are therefore particularly useful for therapeutic applications, for example, delivering into the cells toxins that need to be internalized for their adverse activity. Examples of such toxins include, but not limited to, saporin, calicheamicin, auristatin, and maytansinoid.

The antibodies or polypeptides of the invention can be associated (including conjugated or linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the chemotherapeutic molecule at any location along the antibody so long as the antibody is able to bind its target transferrin receptor.

A toxin or a chemotherapeutic agent may be coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552, 391). The toxin and chemotherapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a chemotherapeutic agent via a microcarrier. Microcarrier refers to a biodegradable or a non-biodegradable particle which is insoluble in water and which has a size of less than about 150, 120 or 100 mm in size, more commonly less than about 50-60 μm, preferably less than about 10, 5, 2.5, 2 or 1.5 μm. Microcarriers include "nanocarriers", which are microcarriers have a size of less than about 1 μm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5] undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or chemotherapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al., *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal AntibodiesT", D. M. Goldenberg ed. (CRC Press, Boca Raton, 1995).

Alternatively, an antibody can be conjugated to a second antibody to form an antibody heteroconjugate as described by Segal in U.S. Pat. No. 4,676,980. The formation of cross-linked antibodies can target the immune system to specific types of cells, for example, cancer or diseased cells expressing transferrin receptor.

This invention also provides methods of delaying development of metastasis in an individual with cancer (including, but not limited to, prostate, lung, breast, ovarian, pancreatic, or colon cancer) using an anti-transferrin receptor antibody or other embodiments that bind to transferrin receptor linked to a chemotherapeutic agent. In some embodiments, the antibody is a humanized or chimeric form of a non-human anti-transferrin receptor antibody.

In yet another embodiment, the antibody can be employed as adjuvant therapy at the time of the surgical removal of a cancer expressing the antigen in order to delay the development of metastasis. The antibody or antibody associated with a chemotherapeutic agent can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

In yet another embodiment, any of the transferrin receptor binding embodiments described herein can bind to transferrin receptor-expressing cancerous cells and induces an active immune response against the cancerous cells expressing transferrin receptor. In some cases, the active immune response can cause the death of the cancerous cells (e.g., antibody binding to cancer cells inducing apoptotic cell death), or inhibit the growth (e.g., block cells cycle progression) of the cancerous cells. In other cases, any of the novel antibodies described herein can bind to cancerous cells and antibody dependent cellular cytotoxicity (ADCC) can eliminate cancerous cells to which anti-transferrin receptor binds. Accordingly, the invention provides methods of stimulating an immune response comprising administering any of the compositions described herein.

In some cases, antibody binding can also activate both cellular and humoral immune responses and recruit more natural killer cells or increased production of cytokines (e.g., IL-2, IFN-g, IL-12, TNF-a, TNF-b, etc.) that further activate an individual's immune system to destroy cancerous cells. In yet another embodiment, anti-transferrin receptor antibodies can bind to cancerous cells, and macrophages or other phagocytic cell can opsonize the cancerous cells.

Various formulations of anti-transferrin receptor antibodies or fragments thereof may be used for administration. In some embodiments, anti-transferrin receptor antibodies or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington, The Science and Practice of Pharmacy* 20th Ed. Mack Publishing (2000).

Suitable formulations for oral administration include hard or soft gelatin capsules, pills, tablets, including coated tablets, elixirs, suspensions, syrups or inhalations and controlled release forms thereof.

Generally, these agents are formulated for administration by injection (e.g., intraperitoneally, intravenously, subcutaneously, intramuscularly, etc.), although other forms of administration (e.g., oral, mucosal, etc) can be also used. Accordingly, anti-transferrin receptor antibodies are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally, a dose of at least about 100 ug/kg body weight, more preferably at least about 250 ug/kg body weight, even more preferably at least about 750 ug/kg body weight, even more preferably at least about 3 mg/kg body weight, even more preferably at least about 5 mg/kg body weight, even more preferably at least about 10 mg/kg body weight is administered.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of anti-transferrin receptor antibodies may be appropriate. Various formulations and devices for achieving sustained release are known in the art.

In one embodiment, dosages for anti-transferrin receptor antibodies may be determined empirically in individuals who have been given one or more administration(s). Individuals are given incremental dosages of an anti-transferrin receptor antibody. To assess efficacy of anti-transferrin receptor antibodies, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. Anti-transferrin receptor antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. In one embodiment, a mixture of different anti-transferrin receptor antibodies is used. A mixture of antibodies, as they are often denoted in the art, may be particularly useful in treating a broader range of population of individuals.

The following examples are provided to illustrate, but not to limit, the invention.

EXAMPLES

Certain Materials and Methods referred to in the following Examples are presented at the end of this section.

Example 1

Preparation of Cancer Cell Lines as an Immunogen

Whole cells isolated from tissue or from cell culture were used as an immunogen for producing monoclonal antibodies that are specific for surface antigens representative of a particular cell type. Such methods, suitable for the practice of this invention, are described in U.S. Pat. No. 6,541,225. Generally, to produce monoclonal antibodies directed to cell-surface antigens of a specific cell type, it is desirable to immunize non-transformed B-cells with viable and intact cells of that type, preferably with those cells whose surfaces that are free of serum. Cell lines that are suitable for the generation of monoclonal antibodies against the antigen transferrin receptor, such as but not limited to LUCA31, include: BT-474 (ATCC# HTB-20), MDA-MB-175VII (ATCC# HB-25), MDA-MB-361 (ATCC # HB-27), SKBR3 (ATCC# HTB-30), SKMES-1 (ATCC# HTB-58), ES-2 (ATCC# CRL-1978), SKOV3 (ATCC# HTB-77), HPAFII (ATCC# CRL-1997), Hs700T (ATCC# HTB-147), Colo205 (ATCC# CCL-222), HT-29 (ATCC# HTB-38), SW480 (ATCC# CCL-228), SW948 (ATCC# CCL-237), A498 (ATCC# HTB-44) and Caki-2 (ATCC# HTB-47).

The cells were grown in the appropriate nutrient media supplemented with growth factors, but free of serum. Immunization with cells that have been propagated in a serum-supplemented medium can have extreme disadvantages. Serum contains a complex mixture of small and large biomolecules with undefined activities. These biomolecules can adhere to the surfaces of cells and thereby leading to the generation of antibodies cross-reacting with molecules not representative of the specific cell type. Additionally, binding of serum biomolecules to the cell surface may lead to the masking of desired cell surface antigen targets. A number of serum-free media preparations are commercially known and publicly available, such as for example, F12/DME (1:1) nutrient media with the following supplements: insulin (10 μg/ml final concentration), epidermal growth factor (EGF) (5 ng/ml final concentration), selenious acid ($2.5 \times 10^{-8}$ M final concentration), and porcine pituitary extract (PPE) (5 μl/ml final concentration).

To harvest the cells, the cell monolayers were rinsed once with calcium- and magnesium-free Hanks saline solution, incubated in 10 mM EDTA in Hanks saline solution at 37 C for 15 minutes. The cells were detached from the culture surface by gentle pipetting. The cell suspension was pelleted by centrifugation at 1000×g for 5 minutes. The supernatant was removed and cells were resuspended in serum-free medium with non-denaturing adjuvant as appropriate.

Example 2

Generation of Monoclonal Antibodies

A non-denaturing adjuvant (Ribi, R730, Corixa, Hamilton Mont.) was rehydrated to 2 ml in phosphate buffered saline. 100 μl of this rehydrated adjuvant was then gently mixed with some of the cell pellet from Example 1 to be used for immunization. Approximately $10^6$ human fetal kidney cells per mouse were injected into Balb/c mice via footpad, approximately once or twice a week. The precise immunization schedule is as follows: Day zero, immunization plus Ribi. Day 3, immunization plus Ribi. Day 7, immunization plus Ribi. Day 24, immunization minus Ribi. Day 29, immunization minus Ribi. Day 32, immunization minus Ribi. Day 36, immunization minus Ribi. Day 44, immunization minus Ribi. Day 51, immunization minus Ribi. Day 69, bleed for titer test. Day 71. immunization plus Ribi. Day 74, immunization plus Ribi. Day 81, immunization plus Ribi. Day 91, prefusion boost (no Ribi). Day 104, harvest nodes for fusion.

At Day 69, a drop of blood was drawn from the tail of each immunized animal to test the titer of antibodies against the cell line used to immunize using FACS analysis. When the titer reached at least 1:2000, the mice were sacrificed using $CO_2$ followed by cervical dislocation. Lymph nodes were harvested for hybridoma preparation.

Lymphocytes from mice were fused with the mouse myeloma line X63-Ag8.653 using 35% polyethylene glycol 4000. On day 10 following the fusion, the hybridoma supernatants were screened for the presence of the immunizing cells—specific monoclonal antibodies by fluorescence activated cell sorting (FACS). Conditioned medium from each hybridoma was incubated for 30 minutes with an aliquot of human fetal kidney cells. After incubation, the cell samples were washed, resuspended in 0.1 ml diluent and incubated with 1 μg/ml of FITC conjugated F(ab')2 fragment of goat anti-mouse IgG for 30 min at 4 C. The cells were washed, resuspended in 0.2 ml FACS diluent and analyzed using a FACScan (tm) cell analyzer (Becton Dickinson; San Jose, Calif.). Hybridoma clones were selected for further expansion, cloning, and characterization based on their binding to the surface of the human fetal kidney cells by FACS. A hybridoma making a monoclonal antibody designated LUCA31 that binds an antigen designated Ag-transferrin receptor and an epitope on that antigen designated Ag-transferrin receptor.1 was selected.

Example 3

Purification of Anti-Transferrin Receptor Antibodies, Including LUCA31

Human cancer cells such as but not limited to SKMES-1, 786-O, and Colo205 cell lines were detached from tissue culture flasks in the presence of 10.0 mM EDTA, centrifuged at 1400 rpm for 5 minutes and resuspended in PBS containing 1% BSA and 2 mM EDTA (FACS diluent). The cells were counted and adjusted to $10^7$ cells/ml. About 0.1 ml of cells were incubated with 100 μl FACS diluent for 30 minutes at 37 C. Monoclonal antibodies that bind to the human cancer cell lines were purified from tissue culture supernatant using protein-G affinity chromatography. The following materials were used for the antibody purification process: hybridoma tissue culture supernatant, Immunopure (G) IgG binding buffer (Pierce #21011 Rockford, Ill.), Immunopure IgG Elution Buffer (Pierce #21009), concentrated HCl (for adjusting pH), Corning 1 liter PES (polyether sulfone), 0.22 μm filter (Corning #431098, Corning, N.Y.), Amersham Pharmacia AKTA Explorer System (Amersham Biosciences, Piscataway, N.J.), Protein-G Sepharose 4 Fast Flow (Amersham Biosciences #17-0618-03), Stripping buffer consisting of 3M Potassium thiocyanate/50 mM Tris pH 7.8, and PBS (phosphate buffered saline), 3M Tris pH 9.0.

To purify the mouse anti-hutransferrin receptor antibody referred to herein as LUCA31, the volume of the supernatant was measured and an equal volume of binding buffer was added to the supernatant. The mixture was allowed to equilibrate to room temperature. The supernatant was clarified by passage through a 0.22 μm filter. The supernatant was loaded onto a protein-G Sepharose column using the AKTA Explorer system (Amersham Biosciences) and then washed with 5-10 column volumes of binding buffer. The monoclonal antibody was eluted with the elution buffer, and fractions were collected. The fractions were neutralized upon elution with the addition of 3M Tris, pH 9.0 to empty tubes (1/60 volume of the fractions). The peak fractions containing the monoclonal antibody were pooled. The pooled samples was injected into a pre-wetted slidealyzer cassette (10,000 MW cutoff; Pierce #66810) and dialyzed in 1×PBS at 4 C (with 3 buffer changes of at least 4 hours of dialysis per change). The purified monoclonal antibody was sterile filtered (0.2 μm Acrodisc) and stored at 2-8 C.

A sample of purified antibody is taken for determination of concentration by UV absorbance ($A_{280}$) and SDS-polyacrylimide gel electrophoresis (SDS-PAGE). SDS-PAGE is run under both non-reducing and reducing conditions for analysis of molecular weight, identification of the typical banding pattern of monoclonal antibodies and assessment of purity.

After purification of the LUCA31 monoclonal antibody from the hybridoma supernatant, it was re-tested for binding to human fetal kidney cells. The cell samples were prepared as described above and incubated with the purified antibody at various concentrations. After incubation the cells were washed, resuspended in 0.1 ml diluent and incubated with 1 μg of FITC conjugated F(ab)'2 fragment of goat anti-mouse IgG for 30 minutes at 4 C. The cells were washed, resuspended in 0.5 ml FACS diluent and analyzed using a FACScan cell sorter (Becton Dickinson, San Jose, Calif.). A shift to the right on the FACScan histogram indicated that the purified antibody still bound to human fetal kidney cells.

In other experiments, the binding of the LUCA31 antibody to transferrin receptor was tested using live cell ELISA. The following method was used, although other methods commonly known in the field are applicable. Cells (HT-29, SKOV3, SKMES-1, SW480, SKBR-3, and HPAFII) were grown in 10% fetal bovine serum (FBS) containing media to confluency on tissue culture treated 96-well plates (Falcon). Cells were washed with PBS and then incubated with 50 μl of desired antibodies at a desired concentration in Hank's Balanced Salt Solution (HBSS) containing 1% BSA and 0.1% sodium azide for 1 hour at room temperature. The cells were then washed three times with 100 μl per well of HBSS before incubation with horseradish peroxidase (HRP) secondary antibody (50 μl per well diluted in HBSS) for 30 minutes at room temperature. The cells were finally washed three times with HBSS and the color change substrate (TMB substrate, KPL) was added to each well at 100 μl per well. The color change reaction was stopped with the addition of 100 μl per well of 1M phosphoric acid. The plates were then read at O.D. 450 nm.

Example 4

Sequencing of LUCA31

RT-PCR with the degenerate oligos listed in the Materials and Methods section yielded distinct bands using MVHrev1 and rev2 with MVHfwd9 for the heavy chain. For the light chain, the combination of MVLrev with both MVLfwd2 and fwd5 yielded product. The PCR program used includes a 10-minute incubation at 72° C. for use in Topo cloning. PCR products were ligated to the pCR2.1 Topo TA cloning vector following the manufacturer's protocol. Twenty colonies of each ligation were picked for mini preps and those with the correct sized inserts were submitted to microchemistry for sequencing with M13 and M13rev.

Consensus sequence was derived for each PCR product, used in a BLAST search, and representative mini preps were chosen to proceed with cloning.

Luca31 Light Chain:

The Luca31 LC generated with MVLrev and MVLfwd2 had an incomplete Vregion. The LC generated with MVLfwd5 was complete. Clone 5.19 was chosen for use as the template in the next step of cloning. PCR primers were designed to incorporate a HindIII site and optimal Kozak at the 5' end, and a BbsI site at the 3' end of the VL region. Luca31 VL fwd (SEQ ID NO:1) and Luca31 VL rev (SEQ ID NO:2) are shown below.

| Primer Name | Sequence |
|---|---|
| Luca31 VL fwd | GAAAACCAAGCTTACCGCCACCATGGATTTTCAGGTGCAG |
| Luca31 VL rev | CGGGAAGATGAAGACAGATGGTGCAGCATCAGCCCG |

PCR was carried out on LC clone 5.19 and the resultant band was gel extracted, digested with HindIII and BbsI, then ligated to the 8.5 kb pDEF2B/Kappa vector fragment, digested with the same enzymes, to yield pDEF2B/Luca31.LC. Mini-preps were sequenced with primers 96-91 and CM-KR and a correct clone was chosen to seed a maxi prep culture.

Light chain expression vectors were created by ligating the 1776 by NotI-XbaI LC fragment from pDEF2B/Luca31.LC to the 11.7 kb pNEF32 or 19.4 kb pNEF5 NotI-XbaI vector fragments, to create pNEF32/Luca31.LC and pNEF5/Luca31.LC.

Luca31 Heavy Chain:

The Luca31 HC PCR products differed only in their 3' ends, as MVHrev1 and Rev2 are slightly offset from each other. A consensus sequence was genererated, and contains two rare codons, but the DNA sequence is clear at those sites. Clone 9R1.1 was chosen for use as the template in the next step of cloning. PCR primers were designed to incorporate a HindIII site and optimal Kozak sequence at the 5' end and an NheI site at the 3' end of the VH region. Luca31 VH fwd (SEQ ID NO:3) and Luca31 VH rev (SEQ ID NO:4) are shown below.

| Primer Name | Sequence |
|---|---|
| Luca3 1 VH fwd | GAAAACCAAGCTTGCCGCCACCATGGATTGGGTGTGGAAC |
| Luca3 1 VH rev | GCCCTTGGTGCTAGCTGCAGAGACAGTGACCAGAGT |

PCR was carried out on HC clone 9R1.1 and the resultant band was gel extracted, digested with HindIII and NheI, then ligated to the 9.3 kb pICFSP.IgG1.NH or pICFSP.IgG4.NH HindIII-NheI vector fragments to create pICFSP.Luca31.G1 or G4.HC, respectively.

Heavy chain expression vectors were created by ligating the 3.2 NotI-XbaI HC fragments from pICFSP.Luca31.G1 or G4.HC to the 12 kb pDEF32 or 19.7 kb pDEF14 NotI-XbaI vector fragments to create pDEF32/Luca31.G1.HC, pDEF14/Luca31.G1.HC, pDEF32/Luca31.G4.HC and pDEF14/Luca31.G4.HC.

All-in-One Expression Vectors:

pDEF 14 all in one expression vectors were created by ligating the 19.7 kb pDEF 14 Nod XbaI vector fragment to a 3.4 kb BglII-XbaI pDEF 2B/Luca 31.LC light chain fragment and a 6.5 kb NotI-BamHI pICFSP/Luca 31.G 1 to create pDEF 14/Luca 31.1.

The following sequences were determined:

LC Lig5.2 (SEQ ID NO:5); L5.11 (SEQ ID NO:6); L5.19 (SEQ ID NO:6); HC Topo consensus (SEQ ID NO:7); Ligated 9R2 (SEQ ID NO:8); Ligated 9R1 (SEQ ID NO:9), shown below:

```
Summary View of Contig "Consensus Alignment Topo LC5"
>LC Lig5.2              #1    GGGACGTCGA CATGGATTTT CAGGTGCAGA TTTTCAGCTT
<L5.11 @10/12/2004.>    #1>              ATGGATTTT CAGGTGCAGA TTTTCAGCTT
<L5.19 @10/12/2004.>    #1>              ATGGATTTT CAGGTGCAGA TTTTCAGCTT
                              ........................................
                        #1    GGGACGTCGA CATGGATTTT CACCTGCAGA TTTTCACCTT >LC Lig5.2              #41   CCTGCTAATC AGTATCTCAG TTGTAATGTC CAGAGGAGAA
<L5.11 @10/12/2004.     #30   CCTGCTAATC AGTATCTCAG TTGTAATGTC CAGAGGAGAA
<L5.19 @10/12/2004.     #30   CCTGCTAATC AGTATCTCAG TTGTAATGTC CAGAGGAGAA
                              ........................................
                        #41   CCTGCTAATC AGTATCTCAG TTGTAATGTC CAGAGGAGAA >LC Lig5.2              #81   AATGTGCTCA CCCAGTCTCC AGCAATCATG TCTGCATCTC
<L5.11 @10/12/2004.     #70   AATGTGCTCA CCCAGTCTCC AGCAATCATG TCTGCATCTC
<L5.19 @10/12/2004.     #70   AATGTGCTCA CCCAGTCTCC AGCAATCATG TCTGCATCTC
                              ........................................
                        #81   AATGTGCTCA CCCAGTCTCC AGCAATCATG TCTGCATCTC >LC Lig5.2              #121  TAGGGGAGAA GGTCACCATG AGCTGCAGGG CCAGCTCAAG
<L5.11 @10/12/2004.     #110  TAGGGGAGAA GGTCACCATG AGCTGCAGGG CCAGCTCAAG
<L5.19 @10/12/2004.     #110  TAGGGGAGAA GGTCACCATG AGCTGCAGGG CCAGCTCAAG
                              ........................................
                        #121  TAGGGGAGAA GGTCACCATG AGCTGCAGGG CCAGCTCAAG >LC Lig5.2              #161  TGTAAATTAC ATATACTGGT ACCAGCAGAA GTCAGATGCC
<L5.11 @10/12/2004.     #150  TGTAAATTAC ATATACTGGT ACCAGCAGAA GTCAGATGCC
<L5.19 @10/12/2004.     #150  TGTAAATTAC ATATACTGGT ACCAGCAGAA GTCAGATGCC
                              ........................................
                        #161  TGTAAATTAC ATATACTGGT ACCAGCAGAA GTCAGATGCC >LC Lig5.2              #201  TCCCCCAAAC TGTGGATTTA TCACACATCC AACCTGGCTC
<L5.11 @10/12/2004.     #190  TCCCCCAAAC TGTGGATTTA TCACACATCC AACCTGGCTC
<L5.19 @10/12/2004.     #190  TCCCCCAAAC TGTGGATTTA TCACACATCC AACCTGGCTC
                              ........................................
                        #201  TCCCCCAAAC TGTGGATTTA TCACACATCC AACCTGGCTC >LC Lig5.2              #241  CTGGAGTCCC AGCTCGCTTC AGTGGCAGTG GGTCTGGGAA
<L5.11 @10/12/2004.     #230  CTGGAGTCCC AGCTCGCTTC AGTGGCAGTG GGTCTGGGAA
<L5.19 @10/12/2004.     #230  CTGGAGTCCC AGCTCGCTTC ACTGGCAGTG GGTCTGGGAA
                              ........................................
                        #241  CTGGAGTCCC AGCTCGCTTC AGTGGCAGTG GGTCTGGGAA >LC Lig5.2              #281  CTCTTATTCT CTCACAATCA GCAGCATGGA GGGTGAAGAT
<L5.11 @10/12/2004.     #270  CTCTTATTCT CTCACAATCA GCAGCATGGA GGGTGAAGAT
<L5.19 @10/12/2004.     #270  CTCTTATTCT CTCACAATCA GCAGCATGGA GGGTCAAGAT
                              ........................................
                        #281  CTCTTATTCT CTCACAATCA GCAGCATGGA GGGTGAAGAT >LC Lig5.2              #321  GCTGCCACTT ATTACTGCCA GCAGTTTACT AGTTCCCCGT
<L5.11 @10/12/2004.     #310  GCTGCCACTT ATTACTGCCA GCAGTTTACT AGTTCCCCGT
<L5.19 @10/12/2004.     #310  GCTGCCACTT ATTACTGCCA GCAGTTTACT AGTTCCCCGT
                              ........................................
                        #321  GCTGCCACTT ATTACTGCCA GCAGTTTACT AGTTCCCCGT >LC Lig5.2              #361  GGACGTTCGG TGGAGGCACC AAGCTGGAAA TCAAACGGGC
<L5.11 @10/12/2004.     #350  GGACGTTCGG TGGAGGCACC AAGCTGGAAA TCAAACGGGC
<L5.19 @10/12/2004.     #350  GGACGTTCGG TGGAGGCACC AAGCTGGAAA TCAAACGGGC
                              ........................................
                        #361  GGACGTTCGG TGGAGGCACC AAGCTGGAAA TCAAACGGGC >LC Lig5.2              #401  TGATGCTGCA CCAACTGTAT CCATCTTCCC ACCATCCAGT
<L5.11 @10/12/2004.     #390  TGATGCTGCA CCAACTGTAT CCATCTTCCC ACCATCCAGT
<L5.19 @10/12/2004.     #390  TGATGCTGCA CCAACTGTAT CCATCTTCCC ACCATCCAGT
                              ........................................
                        #401  TGATGCTGCA CCAACTGTAT CCATCTTCCC ACCATCCAGT >LC Lig5.2              #441  CCCGGG
<L5.11 @10/12/2004.     #430  CCCGGG
<L5.19 @10/12/2004.     #430  CCCGGG
                              ........................................
                        #441  CCCGGG
```

```
Summary View of Contig "Luca31 VH consensus"
<HC Topo consensus        #1      GAATTCGCCC TTACTAGTCG ACATGGATTG
>Ligated 9R2 @10/13/2004.> #1>                    GTCG ACATGGATTG
>Ligated 9R1 @10/13/2004.> #1>              TGGGACGTCG ACATGGATTG
                                  ...............................
                          #1      GAATTCGCCC TKRSWMGTCG ACATGGATTG
                                             *****

<Heavy chain Topo consens. #31     GGTGTGGAAC TTGCTATTCC TGATGGCAGC
>Ligated 9R2 @10/13/2004,. #15     GGTGTGGAAC TTGCTATTCC TGATGGCAGC
>Ligated 9R1 @10/13/2004,. #21     GGTGTGGAAC TTGCTATTCC TGATGGCACC
                                   ...............................
                           #31     GGTGTGGAAC TTGCTATTCC TGATGGCAGC <Heavy chain Topo consens. #61     TGCCCAAAGT GCCCAAGCAC AGATCCAGTT
>Ligated 9R2 @10/13/2004,. #45     TGCCCAAAGT GCCCAAGCAC AGATCCAGTT
>Ligated 9R1 @10/13/2004,. #51     TGCCCAAAGT GCCCAAGCAC AGATCCAGTT
                                   ...............................
                           #61     TGCCCAAAGT GCCCAAGCAC AGATCCAGTT <Heavy chain Topo consens. #91     GGTGCAGTCT GGACCTGAGC TGAAGAAGCC
>Ligated 9R2 @10/13/2004,. #75     GGTGCAGTCT GGACCTGAGC TGAAGAAGCC
>Ligated 9R1 @10/13/2004,. #81     GGTGCAGTCT GGACCTGAGC TGAACAAGCC
                                   ...............................
                           #91     GGTGCAGTCT GGACCTGAGC TGAAGAAGCC <Heavy chain Topo consens. #121    TGGAGAGACA GTCAAGATCT CCTGCAAGGC
>Ligated 9R2 @10/13/2004,. #105    TGGAGAGACA GTCAAGATCT CCTGCAAGGC
>Ligated 9R1 @10/13/2004,. #111    TGGAGAGACA GTCAAGATCT CCTGCAAGGC
                                   ...............................
                           #121    TGGAGAGACA GTCAAGATCT CCTGCAAGGC <Heavy chain Topo consens. #151    TTCTGGGTAT ACCTTCACAA ACTATGGAAT
>Ligated 9R2 @10/13/2004,. #135    TTCTGGGTAT ACCTTCACAA ACTATGGAAT
>Ligated 9R1 @10/13/2004,. #141    TTCTGGGTAT ACCTTCACAA ACTATGGAAT
                                   ...............................
                           #151    TTCTGGGTAT ACCTTCACAA ACTATGGAAT <Heavy chain Topo consens. #181    GAACTGGGTG AAGCAGGCTC CAGGAAAGGG
>Ligated 9R2 @10/13/2004,. #165    GAACTGGGTG AAGCAGGCTC CAGGAAAGGG
>Ligated 9R1 @10/13/2004,. #171    GAACTGGGTG AAGCAGGCTC CAGGAAAGGG
                                   ...............................
                           #181    GAACTGGGTG AAGCAGGCTC CAGGAAAGGG <Heavy chain Topo consens. #211    TTTACAGTGG ATGGGCTGGA TAAACACCTA
>Ligated 9R2 @10/13/2004,. #195    TTTACAGTGG ATGGGCTGGA TAAACACCTA
>Ligated 9R1 @10/13/2004,. #201    TTTACAGTGG ATGGGCTGGA TAAACACCTA
                                   ...............................
                           #211    TTTACAGTGG ATGGGCTGGA TAAACACCTA <Heavy chain Topo consens. #241    CACTGGAGAA CCAACATATG CTGGTGACTT
>Ligated 9R2 @10/13/2004,. #225    CACTGGAGAA CCAACATATG CTGGTGACTT
>Ligated 9R1 @10/13/2004;. #231    CACTGGAGAA CCAACATATG CTGGTGACTT
                                   ...............................
                           #241    CACTGGAGAA CCAACATATG CTGGTGACTT <Heavy chain Topo consens. #271    CAAGGGACGG TTTGCCTTCT CTTTGGAAAC
>Ligated 9R2 @10/13/2004,. #255    CAAGGGACGG TTTGCCTTCT CTTTGGAAAC
>Ligated 9R1 @10/13/2004,. #261    CAAGGGACGG TTTGCCTTCT CTTTGGAAAC
                                   ...............................
                           #271    CAAGGGACGG TTTGCCTTCT CTTTGGAAAC
                                   .

<Heavy chain Topo consens. #301    CTCTGCCAGC ACTGCCTATT TGCAGATCAA
>Ligated 9R2 @10/13/2004,. #285    CTCTGCCAGC ACTGCCTATT TGCAGATCAA
>Ligated 9R1 @10/13/2004,. #291    CTCTGCCAGC ACTGCCTATT TGCAGATCAA
                                   ...............................
                           #301    CTCTGCCAGC ACTGCCTATT TGCAGATCAA <Heavy chain Topo consens. #331    CATCCTCAAA AATGAGGACA CGGCTACATA
>Ligated 9R2 @10/13/2004,. #315    CATCCTCAAA AATGAGGACA CGGCTACATA
>Ligated 9R1 @10/13/2004,. #321    CATCCTCAAA AATGAGGACA CGGCTACATA
                                   ...............................
                           #331    CATCCTCAAA AATGAGGACA CGGCTACATA <Heavy chain Topo consens. #361    TTTCTGTTCA AGAGACGGGG GTAACTACCC
>Ligated 9R2 @10/13/2004,. #345    TTTCTGTTCA AGAGACGGGG GTAACTACCC
>Ligated 9R1 @10/13/2004,. #351    TTTCTGTTCA AGAGACGGGG GTAACTACCC
                                   ...............................
                           #361    TTTCTGTTCA AGAGACGGGG GTAACTACCC
```

```
<Heavy chain Topo consens.   #391  TTTTGCTTAC TGGGGCCAGG GGACTCTGGT
>Ligated 9R2 @10/13/2004,.   #375  TTTTGCTTAC TGGGGCCAGG GGACTCTGGT
>Ligated 9R1 @10/13/2004,.   #381  TTTTGCTTAC TGGGGCCAGG GGACTCTGGT
                                   ................................
                             #391  TTTTGCTTAC TGGGGCCAGG GGACTCTGGT <Heavy chain Topo consens.   #421  CACTGTCTCT GCA
>Ligated 9R2 @10/13/2004,.   #405  CACTGTCTCT GCA
>Ligated 9R1 @10/13/2004,.   #411  CACTGTCTCT GCA
                                   ................................
                             #421  CACTGTCTCT GCA
```

Example 5

Western Blot Analysis of Transferrin Receptor Expression in Cancer Cell Line SW480

Renal cell carcinoma cells SW480 (ATCC# CCL-228) were grown to confluency on 175 $cm^2$ culture dishes. The confluent monolayer was washed three times with Hank's Balanced Salt Solution (HBSS+ containing no sodium bicarbonate or phenol red; buffered with 10 mM HEPES, pH 7.4; Sigma Chemicals) and biotinylated with 200 μg of sulfo-NHS-LC-biotin (Pierce Endogen) for 30 minutes at room temperature. The cells were then washed with HBSS+ containing 0.1M Tris, pH 7.4 (Sigma Chemicals) and incubated in HBSS+ containing 0.1M Tris, pH 7.4 for 15 minutes at room temperature. The cells were finally washed three times with HBSS+ and lysed by incubation for 5 minutes, on ice, in lysis buffer (HBSS+ with 2% Triton X-100, 2 mM PMSF, 0.1% sodium azide, and 1 tablet per 5 ml lysis buffer of EDTA free complete mini-protease cocktail (Roche Molecular Biochemicals)).

Cells were scraped in lysis buffer and lysates collected. Lysates were centrifuged at 14,000×g for one hour at 4 C. The clarified lysate was then pre-cleared for 2 hours at 4 C with 5 μl of human IgG conjugated (1 mg/ml) CNBr 4 MB sepharose beads (Amersham Pharmacia). Human IgG beads were centrifuged and removed, and then the pre-cleared lysate was then incubated with monoclonal antibody LUCA31 conjugated to CNBr 4MB Sepharose beads (conjugated at 1 mg/ml) for 2 hours at 4 C. The LUCA31 beads were centrifuged and removed after the 2-hour incubation. Both the human IgG and the LUCA31 beads were individually washed three times with 1 ml of lysis buffer and then washed three times with 1 ml HBSS+. The washed beads were eluted by the addition of 30 μl of SDS-PAGE sample buffer and boiling at 99 C for 5 minutes.

The samples were then resolved on a 4-20% Novex gradient gel (Invitrogen), and transferred onto 0.2 μm nitrocellulose membrane (Invitrogen) and visualized by horse radish peroxidase (HRP) conjugated streptavidin (Pierce Endogen) or western blotted with 5 μg/blot of LUCA31.

For detection with HRP conjugated streptavidin, the nitrocellulose was first blocked for 1 hour with blocking buffer (5% non-fat dry milk in Tris-buffered saline with 0.05% Tween-20 (TBST)). HRP conjugated streptavidin was diluted into TBST at 1 μg/ml and exposed to the nitrocellulose for 30 minutes at room temperature. The nitrocellulose was washed three times in TBST before visualization with ECL+ (Amersham).

For western blotting with LUCA31, the nitrocellulose was similarly blocked for 1 hour in blocking buffer. The nitrocellulose was then incubated in a heat sealed plastic pouch containing 1 ml of 5 μg/ml LUCA31 diluted in blocking buffer. The nitrocellulose was washed 3 times with TBST before incubation with 10 ml of 1 μg/ml HRP conjugated donkey anti-mouse IgG (heavy and light chain specific, cross adsorbed against bovine, chicken, goat, guinea pig, Syrian hamsters, horse, human, rabbit, sheep serum proteins; Jackson Immunoresearch Cat. #709-035-149) for 1 hour at room temperature. The nitrocellulose was finally washed three times with TBST and visualized by ECL+ (Amersham).

FIG. 1 shows the immunoprecipitation of SW480 cell lysate with LUCA31 and then a western blot using LUCA31 antibody. The arrow points to the unique band with the approximate molecular weight of 90-100 kDa.

Example 6

Immunohistochemistry Methods

Frozen tissue samples from cancer patients were embedded in OCT compound and quick-frozen in isopentane with dry ice. Cryosections were cut with a Leica 3050 CM microtome at thickness of 8-10 μm and thaw-mounted on SuperFrost Plus slides (VWR #48311-703). The sections were fixed with 75% acetone/25% ethanol at 10 C and allowed to air-dry 2-4 hours at room temperature. The fixed sections were stored at −80 C until use.

For immunohistochemistry, the tissue sections were retrieved washed in Tris buffered 0.05% Tween (TB-T) and blocked in blocking buffer (TB-T, 5% normal goat serum and 100 μg/ml avidin) for 30 minutes at room temperature. The slides were then incubated with the anti-transferrin receptor and control monoclonal antibodies diluted in blocking buffer (1 μg/ml) for 60-90 minutes at room temperature. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counter-stained with hematoxylin and examined under Nikon microscope.

In some cases, paraffin embedded formaldehyde-fixed tissues were used for immunohistochemistry after appropriate antigen retrieval methods were employed. One such antigen retrieval method is described in Mangham and Isaacson, *Histopathology* 35:129-33 (1999). Other methods of antigen retrieval and/or detection may be used by one skilled in the art. Results from similar experiments performed using frozen tissues or, where appropriate, fixed tissue with antigen retrieval and polyMICA detection were performed. The binding of anti-transferrin receptor antibody to a variety of normal and cancer tissues was assessed. In all cases, antibody binding in control fixed tissues was correlated with that of frozen tissues. The results from frozen tissues were only used if the two did not match in the controls.

For convenience, a summary of the combined results of several experiments using frozen surgical tissue from different sources is shown below in Table 1 and Table 2.

TABLE 2

Distribution of LUCA31 epitope in human tumor tissues

| Tissue Type | Results |
|---|---|
| Prostate | +/− focal staining on 1 out of 4 tumors screened. 3/4 tumors negative |
| Colon | 3+ staining (5/5 tumors screened) |
| Kidney | 1-2+ focal staining on 4/5 tumors screened; Negative on 1/5 tumors screened |
| Lung | 2-3+ staining on 6/7 tumors screened; Negative on 1/7 tumors screened |
| Ovary | Variable; 1-3+ focal staining on 4/4 tumors screened |
| Pancreas | Variable; 1-3+ staining on 5/5 tumors screened |
| Breast | 1+ on 2/2 tumors screened |

TABLE 1

Distribution of LUCA31 epitope in normal human tissues

| Tissue Type | Results |
|---|---|
| Skin | 1+ on sebaceous gland and subset of sweat glands |
| Lung | Negative except for 3+ on macrophages |
| Kidney | Negative except for 1-2+ on few tubules |
| Pancreas | Negative except for 1+ staining on a few scattered cells |
| Liver | focal 2+ staining on hepatocytes (~10%) |
| Colon | 3+ on upper half or third of the mucosa; 1+ on middle one third of the mucosa |
| Duodenum | 3+ on mucosa (mostly basolateral) |

Example 7

Immunocytochemistry Results

Monoclonal antibody LUCA31 was used to test reactivity with various cell lines from different types of tissues. The results were scored as '+' for weak positive staining, '++' for moderate positive staining, '+++' for strong positive staining and '−' for negative staining.

Immunohistochemistry results were obtained using CellArray™ technology, as described in WO 01/43869. Cells from different established cell lines were removed from the growth surface without using proteases, packed and embedded in OCT compound. The cells were frozen and sectioned, then stained using a standard IHC protocol.

Results of the binding of the LUCA31 antibody to various established human normal and tumor cell lines are compiled for convenience in Table 3. The experiments represented in Table 3 include Live-cell ELISA and CellArray™ binding experiments using the methods described herein.

TABLE 3

| Cell line | ATCC# | Organ | Cell Type | Reactivity Cell Array | Reactivity Live Cell ELISA |
|---|---|---|---|---|---|
| HMEC | CC-2251* | Breast | Normal mammary epithelial | − | |
| HuVEC | Primary | Endothelial cells | Normal human adult | − | |
| BT474 | HTB-20 | Breast | Ductal carcinoma | + | |
| MCF7 | HTB-22 | Breast | Adenocarcinoma | − | |
| MDA175 | HB-25 | Breast | Ductal carcinoma | + | |
| MDA361 | HB-27 | Breast | Adenocarcinoma | ++ | |
| SK-BR-3 | HTB-30 | Breast | Adenocarcinoma | + | + |
| 9979 | RAVEN | Lung | Lung cancer line | + | |
| A549 | CCL-185 | Lung | Carcinoma | − | |
| CA130 | RAVEN | Lung | Small cell carcinoma | +++ | |
| CaLu3 | HTB-55 | Lung | Adenocarcinoma | − | |
| SKMES1 | HTB-58 | Lung | Squamous carcinoma | + | + |
| ES-2 | CRL-1978 | Ovary | Carcinoma | + | |
| SKOV3 | HTB-77 | Ovary | Adenocarcinoma | + | + |
| 9926 | RAVEN | Pancreas | Adenocarcinoma | ++ | |
| AsPC-1 | CRL-1682 | Pancreas | Adenocarcinoma | − | |
| HPAFII | CRL-1997 | Pancreas | Adenocarcinoma | + | − |
| Hs700T | HTB-147 | Pancreas | Adenocarcinoma | + | |
| Colo205 | CCL-222 | Colon | Ascites colorectal adenocarcinoma | ++ | |
| HT-29 | HTB-38 | Colon | Colorectal adenocarcinoma | + | + |
| SW480 | CCL-228 | Colon | Colorectal adenocarcinoma | ++ | + |
| SW948 | CCL-237 | Colon | Colorectal adenocarcinoma | ++ | |
| 293 | CRL-1573 | Kidney | Transformed with adenovirus5 DNA | − | |
| 786-O | CRL-1932 | Kidney | Renal Cell Carcinoma | − | |
| A498 | HTB-44 | Kidney | Carcinoma | + | |
| Caki2 | HTB-47 | Kidney | Clear cell carcinoma | ++ | |
| Cos 7 | CRL-1651 | Kidney (African Green Monkey) | SV40 transformed | − | |
| RL65 | CRL-10345 | Lung (Rat) | | − | |
| SVT2 | CCL-163.1 | Embryo (Mouse) | Fibroblast; SV40 transformed | − | |
| 22RV1 | CRL-2505 | Prostate | Carcinoma | − | |
| DU145 | HTB-81 | Prostate | Adenocarcinoma | − | |
| LNCaP | CRL-1740 | Prostate | Carcinoma | + | |
| PC3 | CRL-1435 | Prostate | Adenocarcinoma | − | |
| TDH-1 | RAVEN | Prostate | Prostate cancer line | + | |
| Hs746T | HTB-135 | Stomach | Carcinoma | − | |
| NCI-N87 | CRL-5822 | Stomach | Carcinoma | − | |

*CC-2251 BioWhittaker

Monoclonal antibody LUCA31 was used to test reactivity with glioma-derived cell lines. Immunocytochemistry results were obtained using similar protocols as described above for the CellArray™ technology. The glioma-derived cell lines were removed from the growth surface without using proteases, packed and embedded in OCT compound. The cells were frozen and sectioned, then stained using a standard IHC protocol. LUCA31 was positive on 21 out of 25 glioma-derived cell lines screened. Staining intensity ranged from +/− to 2+ staining.

Example 8

Additional LUCA Cell Line Screening

Figure 2:
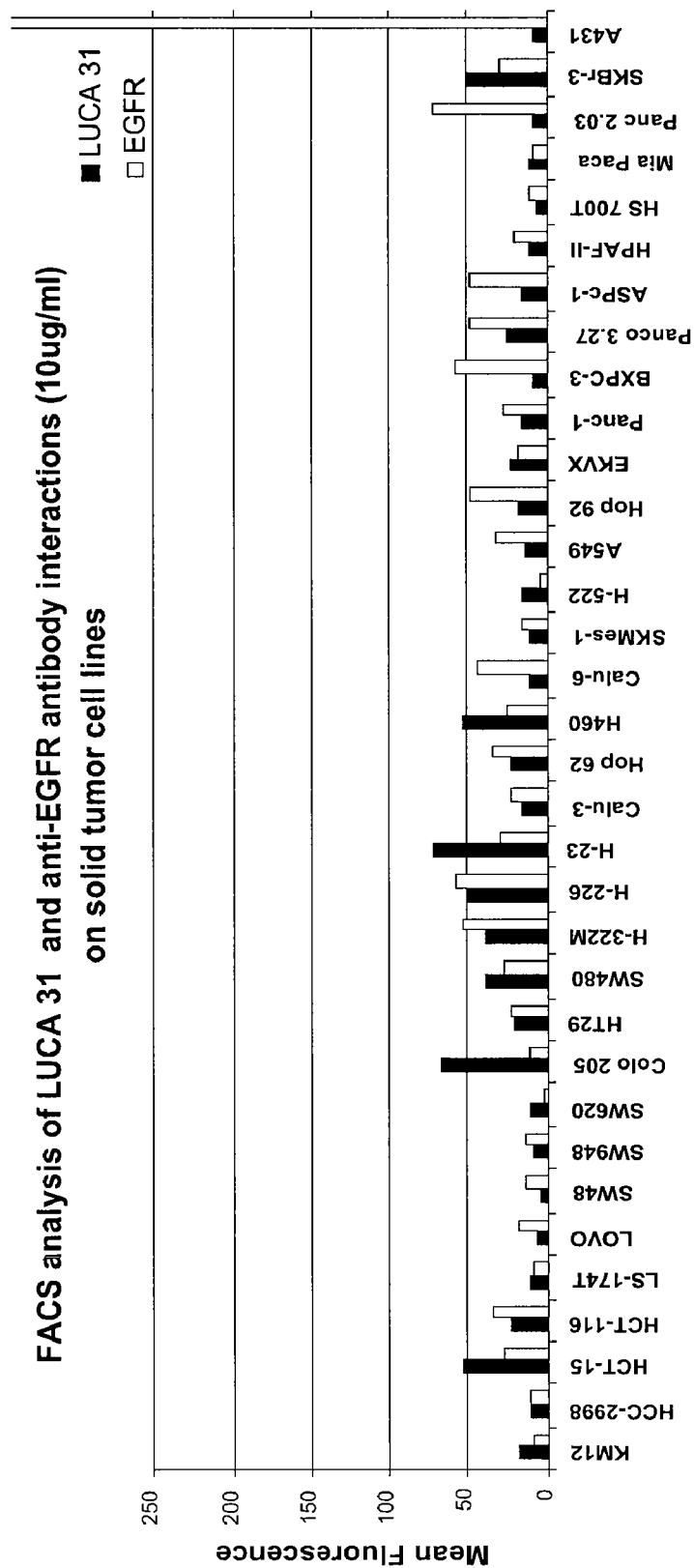
FIG. 2 shows LUCA31 (shaded) and EGF (white) receptor antibody staining of 32 cell line FACS array.

Analysis of tumor cell line distribution. LUCA31 epitope expression was evaluated using a panel of 32 human tumor cell lines representing colorectal, non-small cell lung and pancreatic cancers. The binding of LUCA31 to the target cells was determined relative to an internal antibody standard (anti-EGF receptor) and the data plotted as a function of mean fluorescent intensity. The distribution of LUCA31 staining is shown in FIG. 2. The results of the epitope expression experiments indicated LUCA31 has a broad range of staining intensities across the cell panel.

Example 9

Cell Proliferation Assays

To determine the biological activity of the LUCA31 antibody we tested it in cell proliferation assays, as described elsewhere herein, that measure tritiated thymidine incorporation. Assays were performed for the same 32 cell lines represented in the FACS array and an additional five cell lines that we had shown previously were recognized by this antibody. We tested the antibody for activity using both standard (10%) and low (0.5%) serum conditions. The decision to test for activity using both serum conditions was based on experience with the mouse EGF receptor antibody 225 (murine precursor of cetuximab) which is only active using reduced serum conditions.

Each antibody was tested using five concentrations (10, 5, 2.5, 1.25 and 0.6 ug/ml) of antibody and the results compared to a no-antibody control. Each assay was performed in triplicate. The result of the primary screen of cells is summarized in Table 4 and indicates LUCA31 is broadly active in this panel of cell lines. Shaded cells represent positive scores with the numbers representing maximum inhibition of cell proliferation (i.e. 90=90% growth inhibition).

Inhibition of cell proliferation equal to or greater than 40% was scored as positive. This threshold indicates that the antibody exhibits intrinsic biological activity, consistent with experience with trastuzumab and the EGF receptor antibody 225, both of which induce a 40-50% reduction in cell proliferation in this assay. The LUCA31 antibody was particularly active in this assay, often substantially reducing cell proliferation under low serum conditions. The influence of serum concentration on the activity of this antibody is similar to what is observed for the EGFR antibody 225 using either ASPC-1 or A431 cells.

TABLE 4

| Cell Type | Cell Line | LUCA 31 |
| --- | --- | --- |
| Lung | A549 | 40 |
| Lung | Calu-3 | 40 |
| Lung | SK-MES-1 | 90 |
| Lung | EKVX | 20 |
| Lung | HOP-62 | 50 |
| Lung | HOP-92 | – |
| Lung | NCI-H226 | 50 |
| Lung | NCI-H23 | 30 |
| Lung | NCI-H322M | 50 |
| Lung | NCI-H460 | 40 |
| Lung | NCI-H522 | 30 |
| Lung | Calu-6 | 45 |
| Colon | Colo 205 | 70 |
| Colon | HT-29 | 60 |
| Colon | SW480 | 60 |
| Colon | SW948 | 60 |
| Colon | HCC-2998 | 30 |
| Colon | HCT-15 | 80 |
| Colon | KM12 | 80 |
| Colon | SW-620 | 80 |
| Colon | HCT116 | 80 |
| Colon | SW48 | 60 |
| Colon | LoVo | 60 |
| Colon | Ls174T | 40 |
| Pancreas | AsPC-1 | 40 |
| Pancreas | HPAF-II | 30 |
| Pancreas | Hs 700T | 20 |
| Pancreas | Panc-1 | 60 |
| Pancreas | BX-PC3 | 20 |
| Pancreas | panc 03.27 | 40 |
| Pancreas | MiaPaca | 20 |
| Pancreas | Panc 2.03 | 40 |
| Breast | SKBR-3 | 60 |
| Breast | MDA-MB-175-VII | 90 |
| Kidney | A-498 | 50 |
| Kidney | 786-O | 80 |
| Ovarian | SK-OV-3 | 50 |

Example 10

Additional IHC Analysis

LUCA31 was evaluated using a panel of normal (brain, colon, heart, liver, kidney, lung, pancreas, small intestine, spleen) and tumor (breast, colon, lung, pancreatic) tissues as described in Materials and Methods. Staining was first optimized using tissues identified by Raven as staining positive. Subsequent to optimization, tissues were evaluated for immunoreactivity using peroxidase conjugated secondary antibodies and scored for intensity. A summary of the IHC data produced using LUCA31 at 0.1 ug/ml is presented in Table 5. For LUCA31 the strongest staining in normal tissues is seen in colon and small intestine with limited staining observed in other tissues

TABLE 5

| Tissue | Luca31 |
| --- | --- |
| Brain | – |
| Sm. Intestine | +++ Epithelium |
| Colon | +++ Epithelium |
| Liver | – |
| Kidney | + Prox. Conv. tubules |

TABLE 5-continued

| Tissue | Luca31 |
|---|---|
| Heart | − |
| Spleen | + random cells |
| Pancreas | − |
| Lung | +++ macrophages |

Example 11

Isolation and Characterization of Transferrin Receptor Antigen

To identify the antigen to which LUCA31 was reactive, an immunoprecipitation (Ippt) experiment was performed. For Ippt, 30 175 cm² flasks of SW480 cells were lysed with 30 ml of lysis buffer. The lysis buffer consisted of Hanks balanced salt solution (HBSS+) fortified with 2% Triton X-100, protease inhibitor cocktail (1 tablet per 5 ml lysis buffer of complete mini EDTA free protease cocktail from Roche Molecular Biochemicals), 0.1% sodium azide, and 2 mM PMSF. The cell lysate was clarified at 24,000×g for 30 minutes at 4° C. before being passed over a column consisting of 1 ml Protein G (Amersham Pharmacia). The pre-cleared SW480 lysate was then incubated with Protein G absorbed transferrin receptor (10 μg transferrin receptor was pre-incubated for 30 minutes at room temp with 5 μl Protein G) for 2 hours at 4° C. The beads (both the pre-clear Protein G beads and the Protein G absorbed transferrin receptor beads) were then washed three times with lysis buffer before elution with 30 μl SDS sample buffer (3% SDS, 20% glycerol, 10 mM DTT, 2% Bromophenol blue, 0.1M Tris, pH8.0). Twenty-five microliters of the eluate was then resolved by SDS-PAGE and visualized through Coomassie staining. Five microliters of the eluate was resolved by SDS-PAGE and further transferred to nitrocellulose for western blotting.

The blot was then probed with LUCA31 and developed using a Western Blotting Kit (Invitrogen Cat. No. WB7103) to confirm antigen recognition. By western blotting the transferrin receptor and mouse IgG eluate against transferrin receptor, a protein unique to the transferrin receptor eluate (90-100 kDa) was observed. By Coomassie staining, there was observed to be a transferrin receptor unique protein at ~100 kD. Stained protein bands from the NuPAGE gel are excised using clean scalpel blades and are placed in clean Eppendorf tubes. Excised bands are stored at −20° C. until used for protein identification by mass spectrometry.

Example 12

Characterization of the Antigen to which LUCA31 Binds Using Mass Spectrometry (MS/MS)

The antigen to which LUCA31 binds was isolated as described in Example 11 and subjected to Tandem mass spectroscopy according to the method of Kane et al. J Bio Chem. 2002 Jun. 21; 277(25):22115-8, Epub May 6. Proteins were separated by SDS-PAGE, and the gel stained with colloidal Coomassie Blue reagent (Invitrogen). Proteins of interest were digested in gel with trypsin. The tryptic peptides were sequenced by microcapillary liquid chromatography MS/MS on an ion trap mass spectrometer (Thermo-Finnigan LCDQ DECA XP), as described in Wu et al., Nature 405:477-482 (2000). The results of this yielded one polypeptide with a mass consistent with a fragment of the transferrin receptor.

Figure 3:
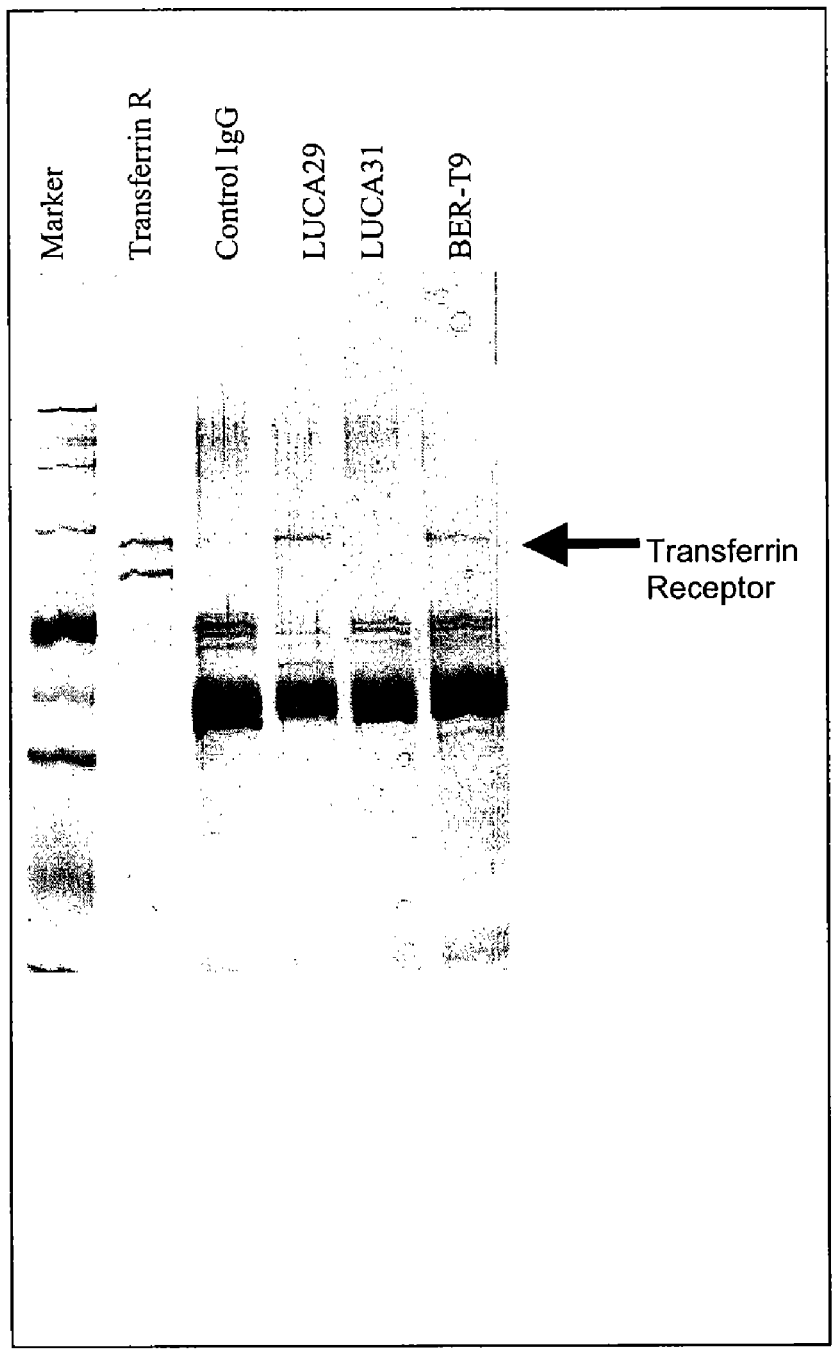
FIG. 3 shows that LUCA31 does not bind to a sample of purified transferrin receptor. Arrow indicates the position of transferrin receptor in the gel.

To confirm whether LUCA31 binds to the transferrin receptor we performed experiments using a preparation of purified transferrin receptor derived from human placenta. As shown in FIG. 3, another anti-transferrin receptor antibody, LUCA29 and the commercially available transferrin receptor antibody BER-T9 both bind to purified transferrin receptor, but LUCA31 does not. Similar results were achieved when this experiment was repeated with a different preparation of transferrin receptor (data not shown).

Figure 4:
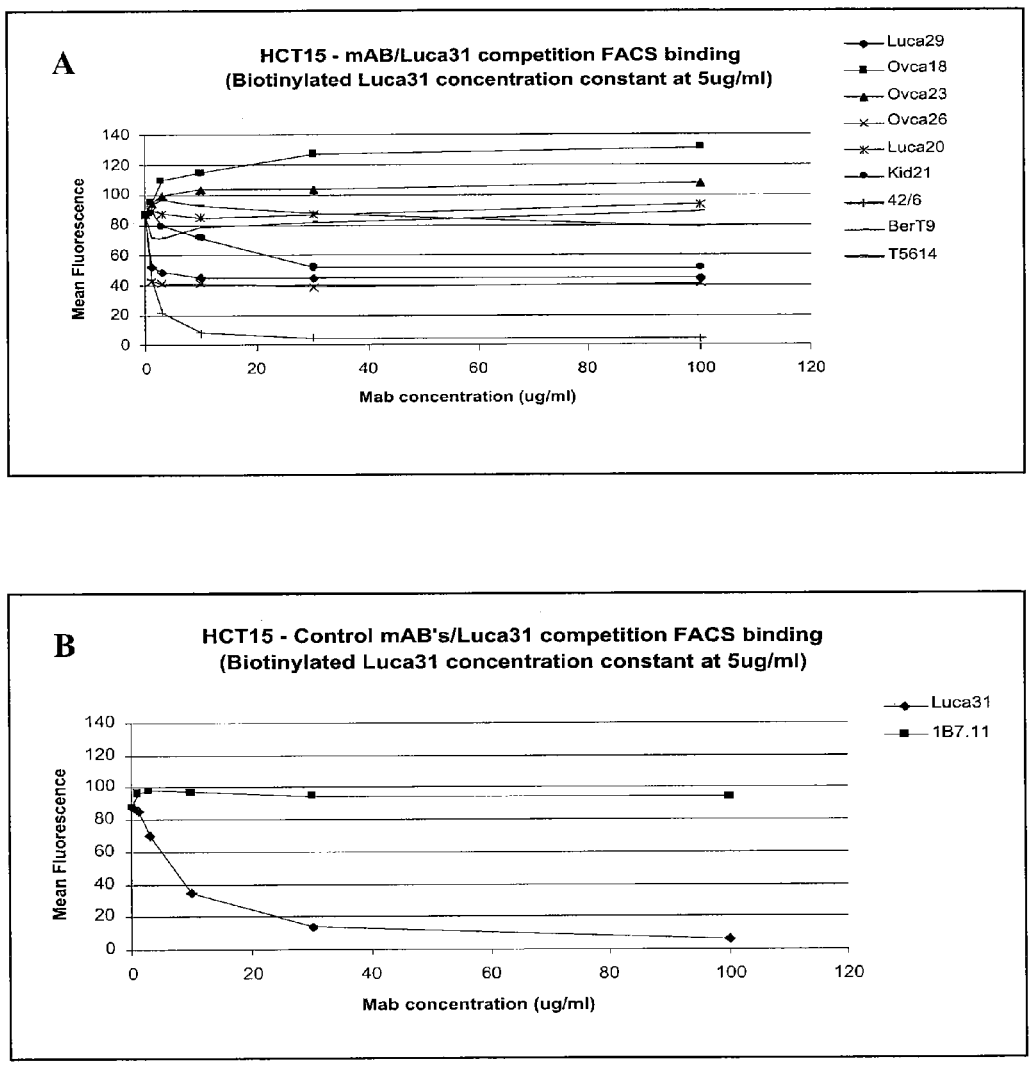
FIGS. 4A and 4B are graphs showing analysis of LUCA31 binding to HCT15 cells in the presence of known transferrin receptor antibodies.
Figure 5:
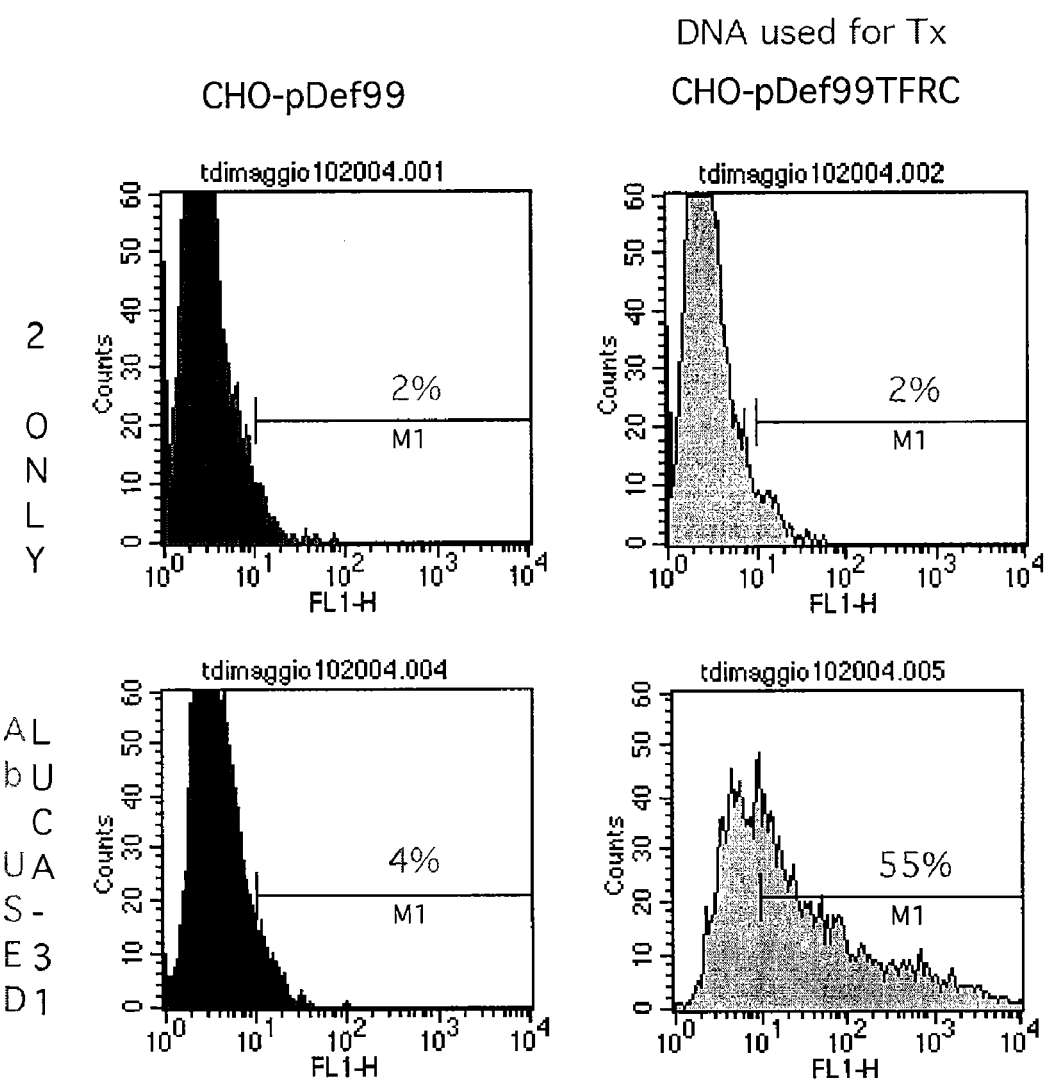
FIG. 5 shows FACS analysis of CHO cells using LUCA31. Cells were transfected with pDEF vector alone (left panel) or pDEF vector containing the human transferrin receptor (right panel).
Figure 6:
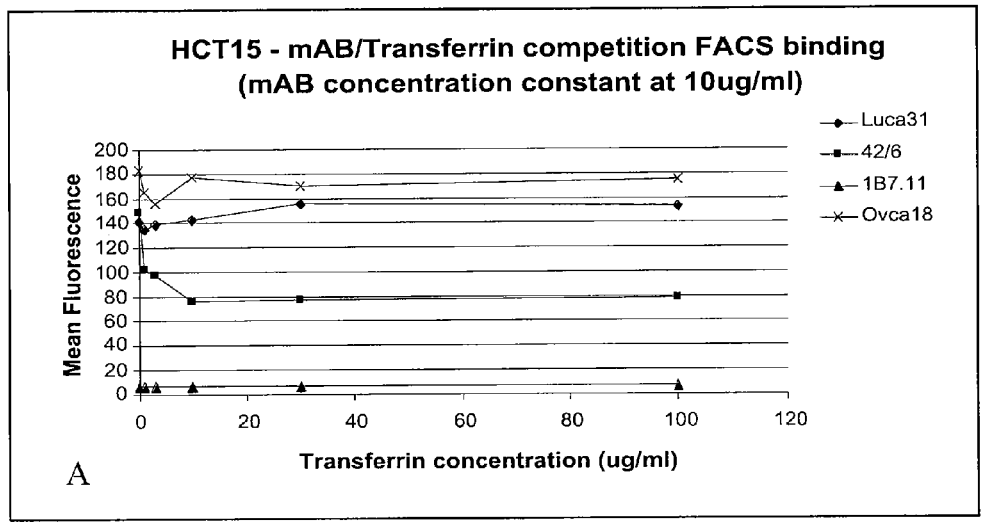
FIG. 6A shows the effect of transferrin on LUCA31 binding to HCT15 cells.
FIG. 6B shows the effect of LUCA31 on transferrin binding to HCT15 cells.
Figure 6:
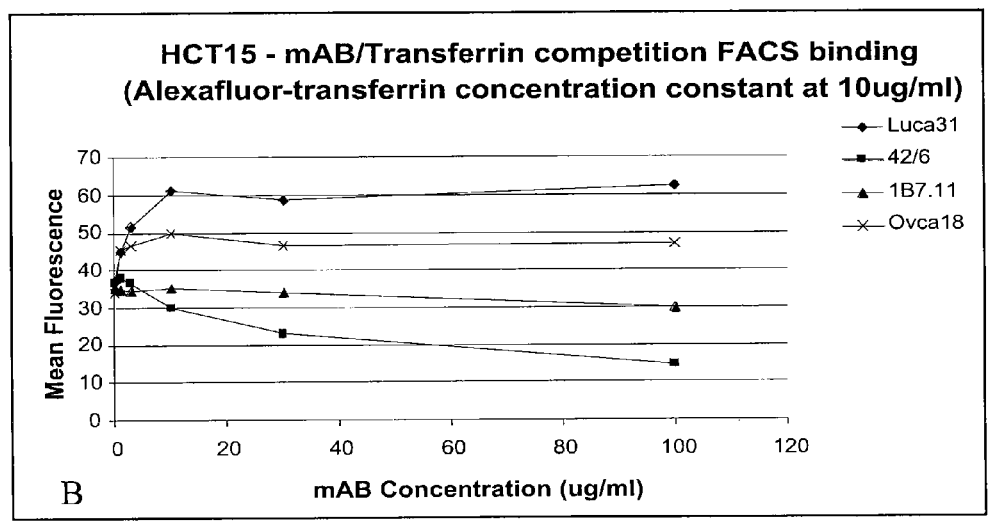

We interpreted these data to indicate that LUCA31 either binds to a protein that interacts with the transferrin receptor or binds to an epitope that is not well represented in the sample of purified material. To refine our understanding of the LUCA31 target we performed the following experiments.

a. Antibody competition analysis. We evaluated the capacity of known transferrin receptor antibodies to compete with LUCA31 for binding to HCT15 cells. The results of this experiment are shown in FIG. 4, A and B. We found the capacity of biotinylated LUCA31 to bind to HCT15 cells was fully inhibited by antibody 42/6 and partially inhibited by OVCA26, LUCA29 and KID21. The OVCA18 antibody increased binding of LUCA31 to cells and the other transferrin receptor antibodies did not appear to affect LUCA31 binding. FIG. 4B demonstrates the negative control antibody 1B7.11 has no effect on LUCA31 binding and that non-biotinylated LUCA31 fully blocks the binding of the biotinylated antibody. Based on these observations, we propose that LUCA31 may recognize an epitope that is stabilized or induced by the OVCA18 antibody and that this epitope may be linked, functionally, to the transferrin binding site. What makes this observation particularly interesting is that OVCA18 also stimulates cell proliferation (data not shown) and stimulates binding of transferrin to cells (see FIG. 6 below). Taken together, these data are consistent with the idea that LUCA31 is binding to the transferrin receptor, but do not rule out the possibility that the antibody might have bound to an associated factor that shares a binding site with a subset of the transferrin receptor antibodies.

b. Expression of transferrin receptor in CHO cells. To further clarify the LUCA31 epitope we cloned and expressed the full-length human transferrin receptor in CHO cells, as described in Materials and Methods. As shown in FIG. 5, FACS analysis of LUCA31 staining of CHO cells was comparable to the level of staining observed with secondary antibody alone. In contrast, CHO cells transfected with the transferrin receptor construct showed substantial staining with LUCA31 relative to the secondary antibody reagent. These data, along with the antibody competition study results, indicate that LUCA31 binds directly to the transferrin receptor.

c. Putative Mechanism of Action. Our current data is consistent with the idea that the LUCA31 antibody binds directly to the transferrin receptor, but that it may interact with an epitope that is not commonly recognized by monoclonal antibodies (mAbs) that specifically bind transferrin receptor. Transferrin receptor antibodies have been shown previously to block cell proliferation by restricting iron transport via perturbation of transferrin receptor endocytosis or by blocking the binding of transferrin to the receptor. To determine whether LUCA31 and transferrin compete for binding to the receptor, we examined the interaction of LUCA31 and transferrin in cell binding assays. Increasing concentrations of transferrin did not appreciably affect the binding of LUCA31 to cells, but did reduce the binding of the benchmark transferrin receptor antibody 42/6 (FIG. 6A). Interestingly, the addition of LUCA31 increased the binding of transferrin to cells whereas the benchmark antibody 42/6 inhibited transferrin binding (FIG. 6B). These results indicate that, unlike 42/6, LUCA31 binds to a site that does not overlap with transferrin binding. This is interesting, considering the observation that 42/6 does inhibit LUCA31 binding to cells. We also examined the effect of the OVCA18 antibody in these studies because of its effect on LUCA31 binding to cells. Like LUCA31, the OVCA18 antibody also increased transferrin binding to cells, but to a lesser degree.

Example 13

Additional Tissue Binding Studies

Target Expression and distribution. Because our data is consistent with the idea that LUCA31 binds to an epitope present on the transferrin receptor, we felt that it was important to evaluate the tissue distribution and expression of the LUCA31 epitope in comparison with the transferrin receptor. Previous studies had indicated LUCA31 did not stain liver, pancreas or brain sections and that these tissues are normally recognized by transferrin receptor mAbs. To extend on this, we analyzed the staining pattern of three known transferrin receptor antibodies (H68.4, BERT9 and DF1513) and LUCA31 using three samples of each of these tissues, and including colon as a reference tissue. The summary of this experiment is shown in Table 6.

ug/ml suggests that the LUCA31 epitope is present in these tissues, but may be less abundant than colon and some tumor samples.

We also examined the staining of additional tumor tissues with LUCA31 to better establish the incidence of epitope expression in cancers. Previously, this antibody was demonstrated to be positive on human colon carcinoma, human pancreatic carcinoma and human lung carcinoma. In this study we evaluated additional lung, pancreatic, and colon carcinoma samples to better establish the incidence of positive reactivity of this antibody. LUCA31 was positive on 4 of 4 colon carcinoma patients; 2 of 2 pancreatic carcinoma patients; and 2 of 2 lung carcinoma patients (Table 7). All tumors were positive at both 1 ug/ml and 10 ug/ml. Colon and lung carcinomas had strong intensity staining at 1 ug/ml whereas pancreatic carcinomas had weak intensity staining at 1 ug/ml and moderate intensity staining at 10 ug/ml of antibody. These results are consistent with other data showing that the LUCA31 epitope is expressed in tumor tissues.

TABLE 7

LUCA31 staining of colon,
non-small cell lung and pancreatic

| Tumor Tissue | Luca31 |
|---|---|
| Colon CA H3210 | +++ Epithelial |
| Colon CA H3174 | +++ Epithelial |
| Colon CA H3170 | +++ Epithelial |

TABLE 6

Comparison of LUCA31 and transferrin receptor antibody staining of brain, pancreas, colon and liver tissue samples.

| Tissue | H68.4 | BERT9 | DF1513 | Luca 31 (0.1 ug/ml) | Luca 31 (10 ug/ml) |
|---|---|---|---|---|---|
| Liver #1 1696-02-02 | + hepatocytes + Kupffer | + Kupffer | + Kupffer | Negative | Not done |
| Liver #2 1696-02-01 | +++ hepatocytes + bile ducts | +++ hepatocytes + bile ducts | ++ hepatocytes + bile ducts | Very faint hepatocytes | Very faint hepatocytes |
| Liver #3 1689-01-01 | +++ hepatocytes + bile ducts | +++ hepatocytes + bile ducts | +++ hepatocytes + bile ducts | Very faint hepatocytes | Very faint hepatocytes ++ macs |
| Pancreas #1 1194-04-01 | +++ acini ++ ducts islets not seen | ++ acini + ducts islets not seen | ++ acini ++ ducts islets not seen | Negative | Not done |
| Pancreas #2 1138-10-03 | ++ acini Ducts not seen | ++ acini Ducts not seen | ++ acini Ducts not seen | Very faint acini Ducts not seen | + acini Ducts not seen |
| Pancreas - CA #3 1194-04-01 | +++ acini +++ islets ++ ducts | +++ acini +++ islets ++ ducts | +++ acini +++ islets ++ ducts | Negative None specific Staining in areas of necrosis | +++ acini − islets ++ ducts |
| Colon #1 3112-01-02 | +++ epithelium | +++ epithelium | +++ epithelium | +++ epithelium | +++ epithelium |
| Brain #1 1138-04-05 | +++ endothelium ++ grey matter − white matter | +++ endothelium + grey matter − white matter | +++ endothelium + grey matter − white matter | Very faint endothelial marking | Not done |
| Brain #2 1289-03-03 | +++ endothelium +++ grey matter − white matter | +++ endothelium ++ grey matter − white matter | +++ endothelium ++ grey matter − white matter | Very faint endothelial marking | +++ endothelial marking |

The results of this experiment are consistent with previous studies and show LUCA31 does not produce the same tissue staining pattern of prototypical transferrin receptor antibodies. These results support the concept that the LUCA31 antibody recognizes an epitope that is distributed in a pattern that is distinct from epitopes recognized by other transferrin receptor antibodies and may provide for a more favorable therapeutic index than other transferrin receptor antibodies. However, the pancreas and brain endothelium staining at 10

TABLE 7-continued

LUCA31 staining of colon,
non-small cell lung and pancreatic

| Tumor Tissue | Luca31 |
|---|---|
| Colon CA H3114 | +++ Epithelial |
| Panc CA H2100 | ++ Epithelial |
| Panc CA H3185 | ++ Epithelial |

TABLE 7-continued

LUCA31 staining of colon,
non-small cell lung and pancreatic

| Tumor Tissue | Luca31 |
|---|---|
| Lung CA H3181 | +++ Epithelial |
| Lung CA H3145 | +++ Epithelial |

Example 14

FACS Analysis of RBCs, Platelets and Leukocytes

An analysis of LUCA31 staining of red blood cells, platelets and leukocytes was performed to evaluate antigen expression in the blood compartment. No staining was observed in any of these cell populations. This is also contradictory to published reports on transferrin receptor expression in monocyte and lymphocyte populations. However, because transferrin receptor expression is induced in stimulated lymphocytes relative to non-proliferating lymphocytes (Neckers & Cossman, *Transferrin receptor induction in mitogen-stimulated human T lymphocytes is required for DNA synthesis and cell division and is regulated by interleukin 2*, Proc Natl Acad Sci USA 80, 3494-3498 (1983)), we extended our analysis by examining the staining of T-lymphocytes stimulated with PHA using LUCA31 (Table 8). As references, we used the transferrin receptor antibodies LUCA29 and BERT9, as well as alpha2 and beta 1 integrin antibodies as standards for lymphocyte staining. Unlike the results of our analysis of the tissue samples, we did not observe a difference between LUCA31 and the other transferrin mAbs in this assay.

TABLE 8

| | Unstimulated | | | | | 3 hr PHA/3 day IL-2 | |
|---|---|---|---|---|---|---|---|
| | Neuts | Monos | Lymphs | Red blood cells | Platelets | Monos | Lymphs |
| LUCA31 | − | +/− | − | − | − | ++ | ++ on T |
| LUCA29 | − | +/− | − | − | −−/+ | ++ | ++ on T |
| BERT9 | − | +/− | − | − | −−/+ | ++ | ++ on T |
| alpha2 | + sub | −/+ | − | − | ++ | − | −/+ on T |
| beta1 | ++ | +++ | +++ | − | not done | +++ | +++ on B and T |
| IgG1 isot. | − | − | − | − | − | − | − |
| | | | PMA stimulation had no effect | | | | |

Notes:
Unless noted the entire population had the indicted staining level.
The abbreviation "sub" indicates that a distinct subpopulation showed activity and the remainder was negative.
"B" cells in this table represent CD3 negative lymphocytes.
"T" cells in this table represent CD3 positive lymphocytes.

Because transferrin receptor has been shown to be expressed on differentiating bone marrow progenitor cells (Helm et al., *Characterization and phenotypic analysis of differentiating CD34+ human bone marrow cells in liquid culture*, Eur J Haematol 59, 318-326 (1997)), we also performed experiments to examine whether the LUCA31 epitope is also expressed in bone marrow derived cells. To do this, we obtained CD34 enriched bone marrow cells and evaluated them by FACS using LUCA31 and another antibody having different specificity, KID20.

The data from this experiment is shown in Table 9, which shows human bone marrow progenitor staining by other antibodies. Antibody staining of both unstimulated and growth factor stimulated cells was determined by FACS and the results presented as the percentage of antibody stained cells. In untreated cells LUCA31 staining was very similar to results obtained with the transferrin receptor antibody BERT9. When cells were cultured for 72 hrs in the presence of growth factors, including GM-CSF, SCF, IL3 and EPO, the proportion of LUCA31 and BERT9 staining cells increased. These results are similar to what we observed with proliferating lymphocytes and indicate the LUCA31 epitope is also expressed in growth factor stimulated bone marrow progenitor cell populations.

TABLE 9

| | Human CD34 selected bone marrow cells | |
|---|---|---|
| | Unstimulated | 72 hrs post stimulation |
| LUCA31 | 8 | 36 |
| KID20 | 0.5 | 0.7 |
| BERT9 | 7 | 30 |
| IgG1 isot. | 0.4 | 2.4 |
| unstained | 0.08 | 2 |

Progenitor cell stimulation conditions 5 ng/ml rGM-CSF 50 ng/ml rSCF 5 ng/ml rIL-3

5 units/ml EPO

Example 15

Activity Assays

To more fully characterize the activity of this molecule, we studied a panel of cells that have been validated in xenograft tumor models (human xenograft cell panel) and demonstrated the antibody is highly active alone, and in combination with chemotherapeutics. Because we have shown LUCA31 interacts with the transferrin receptor, we have benchmarked its activity relative to the well studied IgA transferrin receptor antibody 42/6 (Trowbridge & Lopez, 1982). As shown in Table 10, LUCA31 is active in all of the cell lines in our prioritized xenograft panel and compares favorably with the anti-transferrin receptor antibody 42/6.

TABLE 10

| Tumor Cell Line | Maximum inhibition (% inhibition) | |
| --- | --- | --- |
| | LUCA31 | 42/6 |
| Calu6 | 25 | 0 |
| Colo205 | 25 | 25 |
| H460 | 30 | 20 |
| HCT15 | 70 | 50 |
| HCT116 | 50 | 10 |
| HT29 | 30 | 20 |
| LOVO | 50 | 50 |
| LS174T | 35 | 10 |
| SW48 | 35 | 0 |

Figure 7:
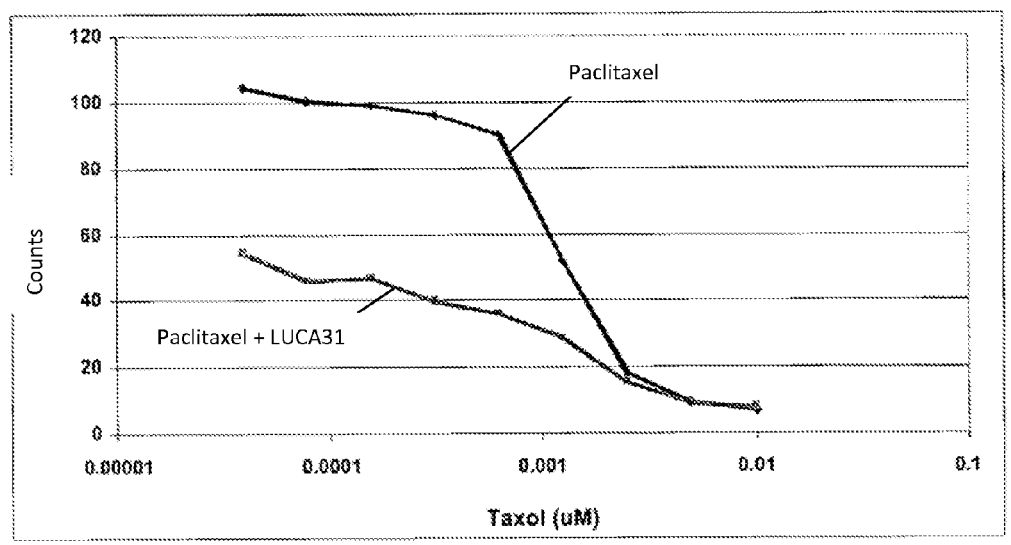
FIG. 7 shows the results of chemotherapy combination studies using paclitaxel alone (top line) or a combination of paclitaxel and 5 ug/ml LUCA31 antibody (bottom line). Cell proliferation was measured by tritiated thymidine incorporation.

The LUCA31 antibody was also tested in the xenograft cell panel in combination with the chemotherapy agents camptothecin, carboplatin, doxorubicin, gemcitabine and paclitaxel. For each agent, the addition of LUCA31 resulted in an additive effect, indicating the antibody is not likely to antagonize the action of oncolytic agents. Representative data for the combination of LUCA31 with chemotherapeutics in HCT116 cells is shown in FIG. 7. The results from the LUCA31 chemotherapy combination studies are comparable to the results we obtained when we examined chemotherapy pairings with the Her2 targeting antibody Trastuzumab.

The activity of LUCA31 is maximal in low serum conditions, suggesting that components available in fetal bovine serum (FBS) attenuate the ability of this antibody to block cell proliferation. The capacity of the 42/6 antibody to block proliferation of solid tumor cell lines has also been shown to be maximal in low serum conditions and that this is due to the competition between the antibody and transferrin (Taetle, R., and Honeysett, J. M. (1987). Effects of monoclonal anti-transferrin receptor antibodies on in vitro growth of human solid tumor cells. Cancer Res 47, 2040-2044). Although LUCA31 does not appear to compete with transferrin for binding to the transferrin receptor, we performed experiments to determine whether the reduced activity of LUCA31 in 10% FBS is a result of increased transferrin in the cell culture medium.

Figure 8:
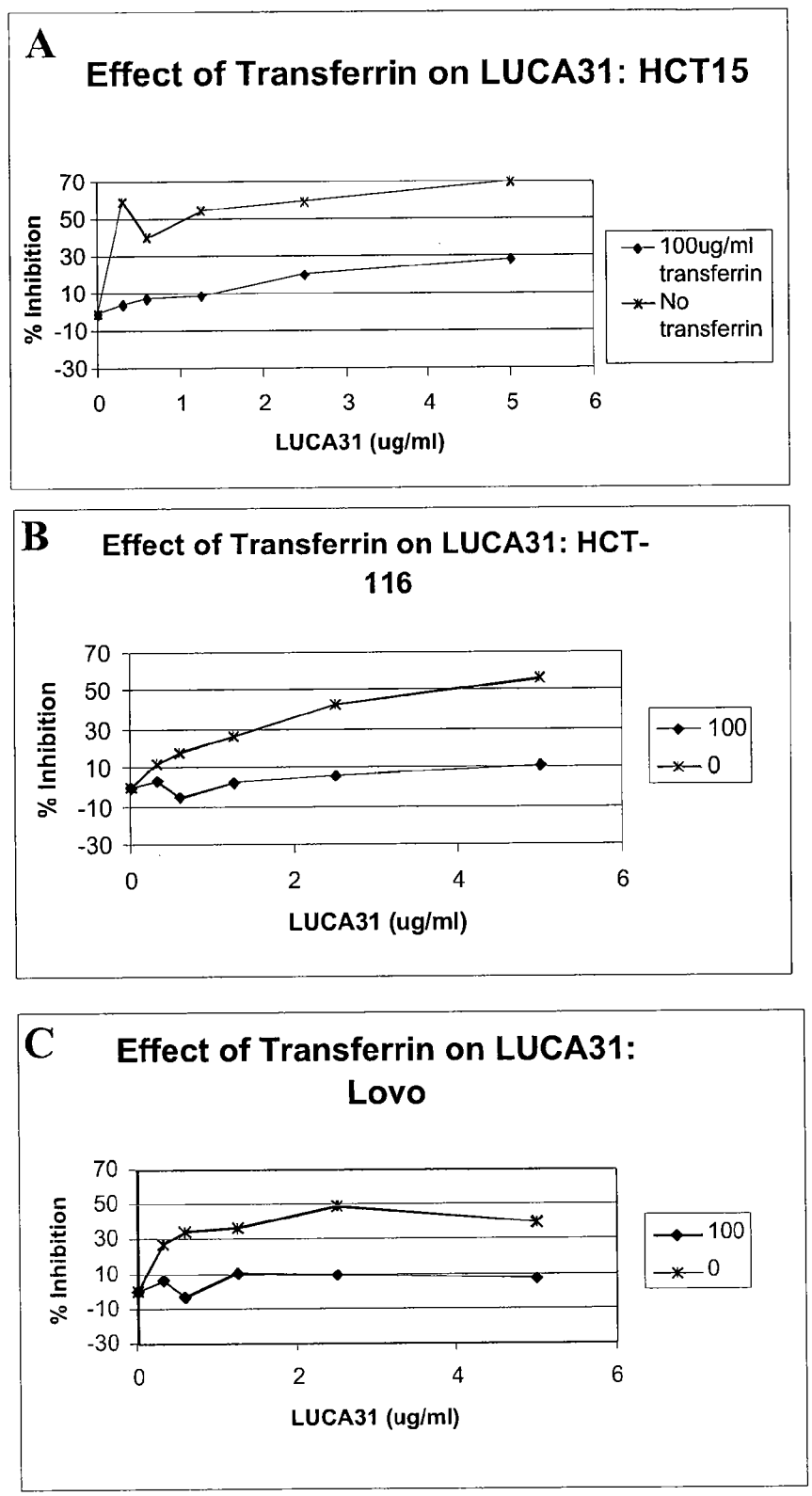
FIG. 8 shows the effect of 100 ug/ml transferrin on the activity of LUCA31 and 42/6 in HCT15 (A), HCT116 (B) and LOVO (C) cells.

To address this question we added iron charged transferrin to low serum media and examined the activity of both LUCA31 and 42/6 using the xenograft tumor cell line panel. We found the activity of both LUCA31 and 42/6 is reduced when holo-transferrin is added to cell culture medium. FIG. 8 shows data for the three cell lines most sensitive to LUCA31; HCT15, HCT116 and LOVO at 0 and 100 ug/ml transferrin. In HCT15 cells, LUCA31 retains good activity in the presence of added transferrin.

This is consistent with the capacity of this antibody to maintain activity in 10% serum as well. Taken together, these data suggest that the capacity of LUCA31 to block cell proliferation can be attenuated by transferrin and support the idea that the restricted activity of this antibody in 10% serum containing cell culture conditions is due to the increased concentration of transferrin. Despite evidence for reduced activity of the antibody 42/6 in high serum, this and other transferrin receptor antibodies have been shown to be active in animal cancer models, suggesting that the capacity of the molecules to work in vivo is not negated by serum transferrin levels.

Example 16

Cell Cycle Analysis

Figure 9:
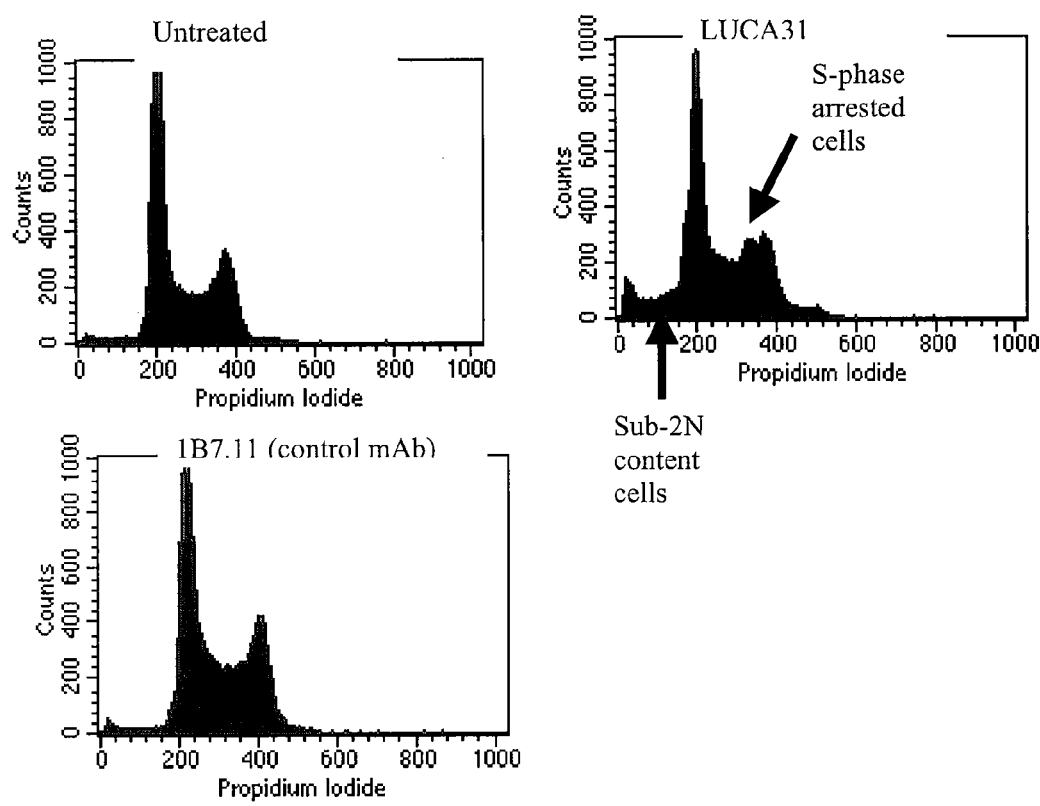
FIG. 9 shows the effect of 5 ug/ml LUCA31 on HCT15 cell cycle progression. DNA content of treated and control cells was determined by propidium. Arrows indicate areas of histogram indicative of S-phase arrest and cell death.

To further define the mechanism of action of LUCA31, we examined how the antibody affected the progression of HCT15 cells through the cell cycle. As shown in FIG. 9, treatment of HCT15 cells with LUCA31 for 24 hrs resulted in a reduction in the proportion of 2N content (G1) cells and increased the population of cells with DNA content consistent with S-phase arrest. Additionally, the HCT15 cells treated with LUCA31 also showed an increased proportion of cells with a DNA content <2N, consistent with cell death. This effect was not apparent in the control antibody treated or the untreated cells. These data suggest that LUCA31 may induce cell death rather than cytostasis in a subpopulation of the HCT15 cells and may provide rationale for why these cells are most sensitive to LUCA31 exposure.

Example 17

Effect of LUCA31 on Tumor Cell Lines

Figure 10:
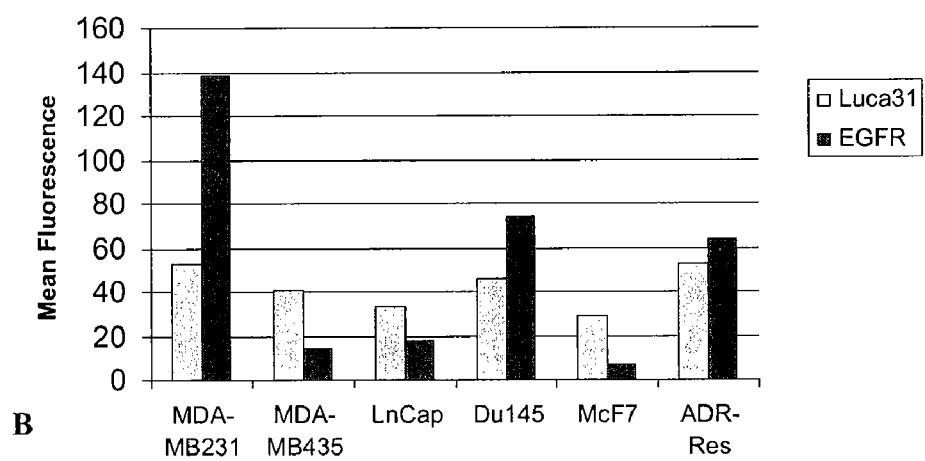
FIG. 10 shows the activity of LUCA31 in a human tumor cell line panel.
Figure 10:
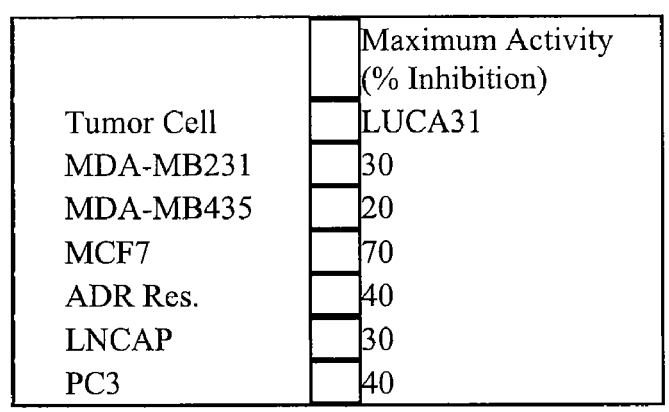

To explore the potential activity of this molecule in additional tumor types, LUCA31 was tested in solid tumor cell lines derived from prostate (DU145, LNCap) and breast (MCF7, MDA-MB-231, MDA-MB-435, ADR-Res) (FIG. 10). Expression of the LUCA31 epitope was similar in each of the cell lines, but LUCA31 appeared to be most active in the MCF7 cells. These results are comparable to the data produced using the colon, lung and pancreatic cancers.

Figure 11:
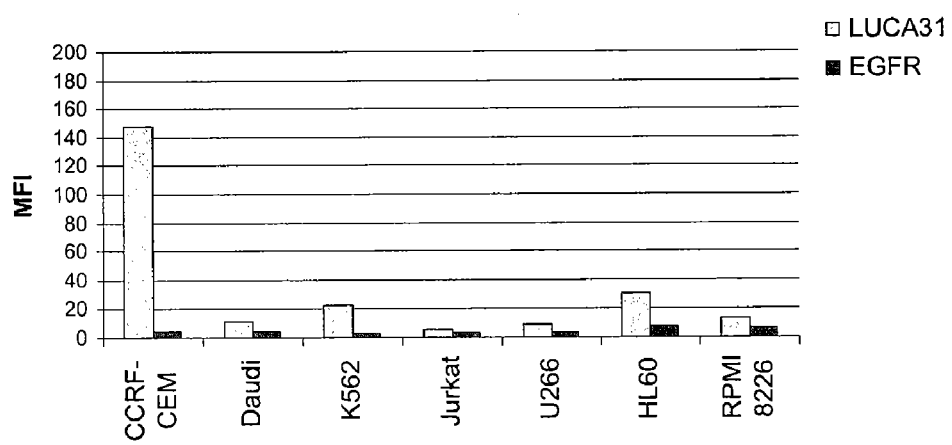
FIG. 11 shows the activity of LUCA31 in a human hematological tumor cell line panel.

In addition to the solid tumor cell lines, we also surveyed for LUCA31 activity using cell derived from lymphomas, leukemias and multiple myelomas. We felt this was important because most of the studies published using the benchmark transferrin receptor antibody (42-6) were performed with hematological cancer cell lines (see e.g., Savage, 1987; Trowbridge & Lopez, *Monoclonal antibody to transferrin receptor blocks transferrin binding and inhibits human tumor cell growth in vitro*, Proc Natl Acad Sci USA 79, 1175-1179 (1982); White, 1990). The results from these experiments, shown in FIG. 11, demonstrate the LUCA31 epitope was most highly expressed in the CCRF-CEM cell line, but was also found in the other cell lines studied (FIG. 11A). LUCA31 was active in each of these cell lines, in some cases reducing cell proliferation to 10% of the control value (FIG. 11B). This activity was superior to the benchmark antibody 42-6 (data not shown) and was maximal with reduced serum.

Example 18

Effect of LUCA31 on Cancer Cell Lines 786-O, SKMES-1. MDA-MB-175VII and Colo205

The ability of the antibodies to reduce cell number in vitro when grown as a monolayer can be assessed using cell monolayers grown in the presence or absence of varying amounts of test or control purified antibody and the change in cell number assessed using MTT. MTT is a dye that measures the activity of mitochondrial enzymes and correlates with relative viable cell number. Cells of interest were plated and grown in F12/DMEM (1:1) growth medium supplemented with 10% fetal bovine serum in 96 well plates. The following cell lines were plated at the following densities in triplicate wells of a 96 well dish: 786-O, Colo205, MDA-MB-175VII, and SKMES-1 at 1800, 1500, 2500 and 1500 cells/well, respectively. Immediately after plating, LUCA31 was added. The cells were incubated at 37° C. in a humidified incubator at 5% CO2/air for 5 days. At the end of the assay, MTT was dissolved in PBS (5 mg/ml) and added directly to wells at 1:10 dilution. Plates were placed back in incubator for 4 hours. After the incubation, medium was removed and 100 µl DMSO was added to solubilize the MTT precipitate. Plates were read at O.D. 540 nm At 20 µg/ml LUCA31 inhibited the growth of renal cell adenocarcinoma 786-O 54% (average of 3 experiments), colorectal adenocarcinoma Colo205 37% (average of 4 experiments), breast ductal carcinoma MDA-MB-175VII 35% (average of 2 experiments) and lung squamous carcinoma SKMES-1 45% (average of 3 experiments).

Figure 12:
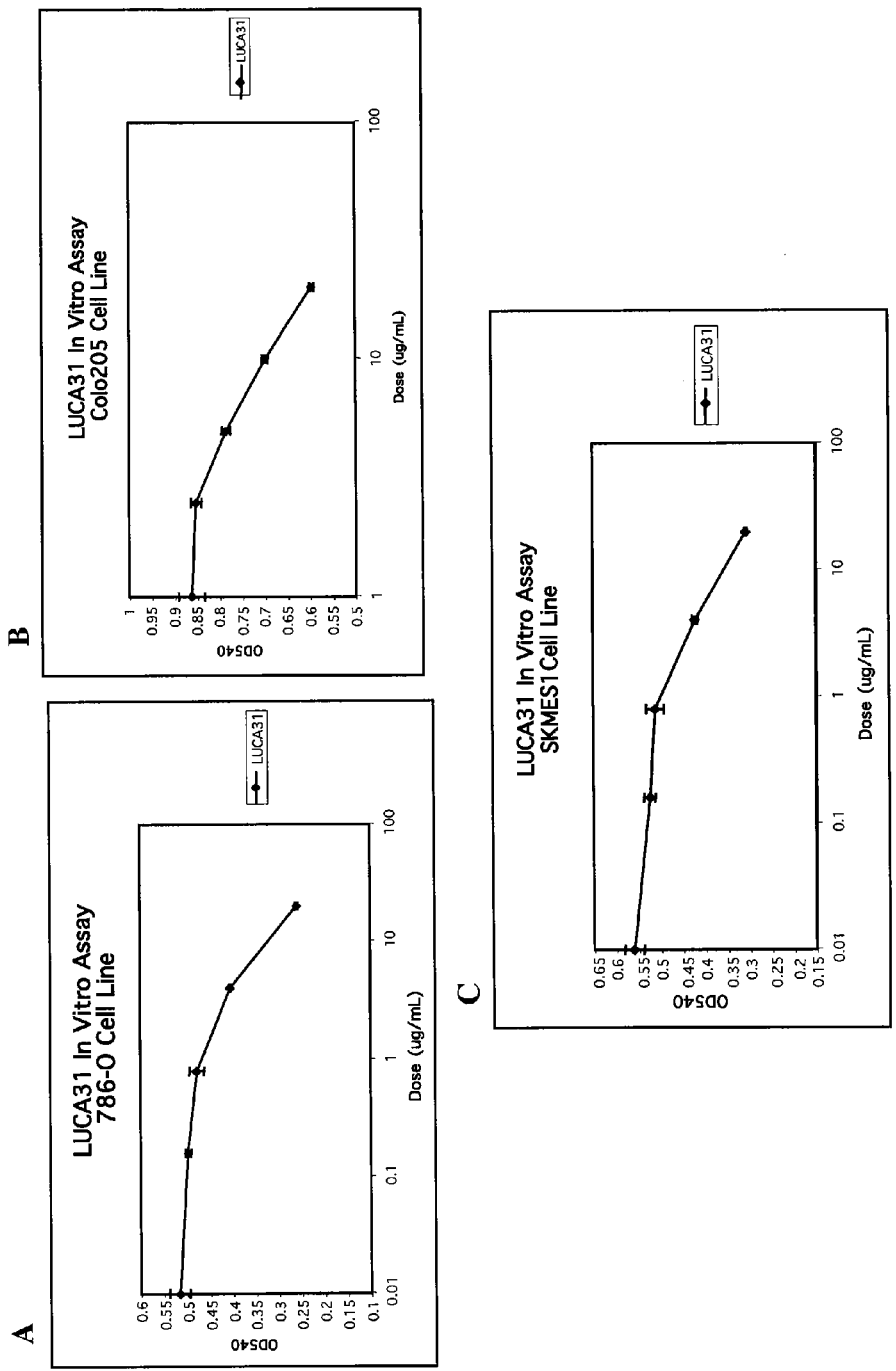
FIG. 12A is a graph showing the in vitro activity of LUCA31 on the growth of 786-O cell line.
FIG. 12B is a graph showing the in vitro activity of LUCA31 on SKMES-1 cell line.
FIG. 12C is a graph showing the in vitro activity of LUCA31 on SKBR3 cell line.

Representative graphed results of the effects of LUCA31 are shown in FIG. 12. FIG. 12A shows representative graphed results of the effects of LUCA31 on 786-O cells. FIG. 12B shows representative graphed results of the effects of LUCA31 on Colo205 cells. FIG. 12C shows representative graphed results of the effects of LUCA31 on SKMES-1 cells.

Example 19

Internalization of LUCA31 and Toxin-Conjugated Anti-Mouse IgG

Mab-ZAP (Advanced Targeting Systems, San Diego, Calif.) is an anti-mouse IgG conjugated to saporin, a toxin that inhibits protein synthesis. This toxin is impermeable to the cell membrane. If a monoclonal antibody is bound to a cell-surface antigen that is internalizable, the toxin-conjugate can bind to the bound monoclonal and, thereby, be internalized and eventually kill the cell. Being dependent upon internalization for demonstration of toxic activity, the Mab-ZAP can serve to evaluate whether or not a given surface antigen will serve as a suitable target for any toxin that is dependent upon internalization to express cell toxic effects. As such, the Mab-ZAP serves as a model for such internalization-dependent toxins such as maytansinoids and calicheamicin.

For testing the internalization of LUCA31 and saporin conjugated anti-mouse IgG by tumor cells and effect of killing the tumor cells after internalization of saporin, human colon tumor cells, Colo205 were removed from stock flasks with 10 mM EDTA and centrifuged. Cells were resuspended at 50,000/ml in appropriate medium and 100 µl plated per well in 96 well plates. Antibody LUCA31 was added immediately to appropriate wells as a 10× concentrate, to make a final concentration of 10 ug/ml. After 15 minutes at room temperature Mab-ZAP (Cat. # IT-04, Advanced Targeting Systems, San Diego Calif.) was added to appropriate wells as 10× concentrate, to make final concentrations from 0.001 nM to 10 nM. After 4 days growth, MTT was added (stock 5 mg/ml PBS, 1:10 dilution in well) for 4 hrs at 37 C. The medium was then removed from all wells and 100 µl/well DMSO was added. The plates were gently swirled to solubilize the blue MTT precipitate and the plates were read at O.D. 540 nm.

There was a decrease in MTT staining in Colo205 cells in the presence of LUCA31 as compared to staining in the absence of LUCA31. This indicates that the growth of Colo205 cells was inhibited in the presence of LUCA31 and Mab-ZAP and these results are indicative of LUCA31 and toxin-conjugated anti-mouse IgG were internalized in Colo205 cells.

Figure 13:
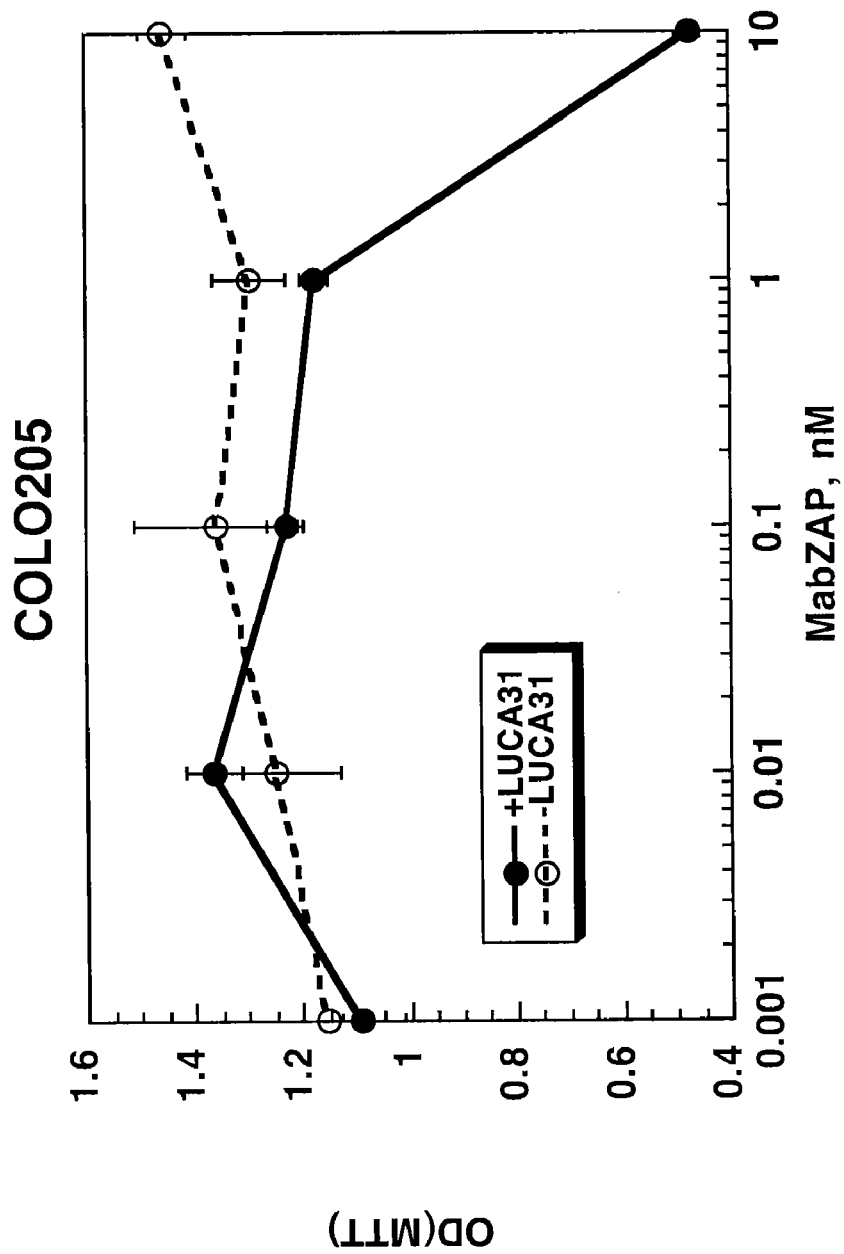
FIG. 13 is a graph showing the effect of LUCA31 and Mab-ZAP (an anti-IgG conjugate to saporin) on the growth of human colon carcinoma cell line Colo205.

Results of an internalization experiment according to the methods of this Example are shown in FIG. 13.

Example 20

Activity with Lymphocyte and Bone Marrow Cells

Figure 14:
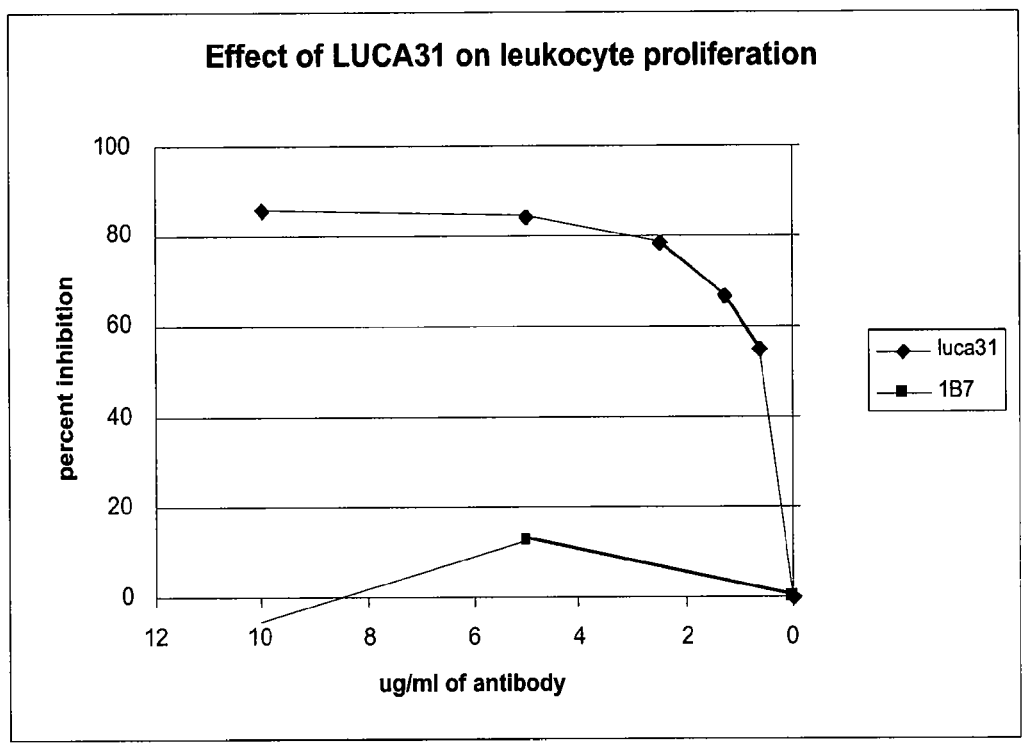
FIG. 14 shows the effect of LUCA31 on leukocyte proliferation. LUCA31 and the control IgG1 antibody 1B7.11 were compared in a normal human leukocyte proliferation assay. Cells were stimulated using PHA and effects on cell proliferation determined by tritiated thymidine incorporation. Data is plotted as a function of percent inhibition (relative to no-antibody control) relative to antibody concentration.

To determine whether the staining of lymphocytes and bone marrow progenitor cells by LUCA31 is predictive of antiproliferative activity in these cells, we developed tritiated thymidine-based cell proliferation assays using human peripheral blood leukocytes and CD34 selected bone marrow progenitor cells. For both of these cell populations we used the same cytokine cocktail that was employed to determine LUCA31 epitope staining. To test the effect of LUCA31 on human leukocytes, we stimulated isolated PBMCs with PHA/IL-2 alone, or in the presence of varying amounts of either a control IgG 1 antibody or LUCA31. The results of this experiment (FIG. 14) show that LUCA31 potently inhibited the incorporation of tritiated thymidine in the proliferating leukocyte population, resulting in nearly 90% inhibition of cell proliferation.

Figure 15:
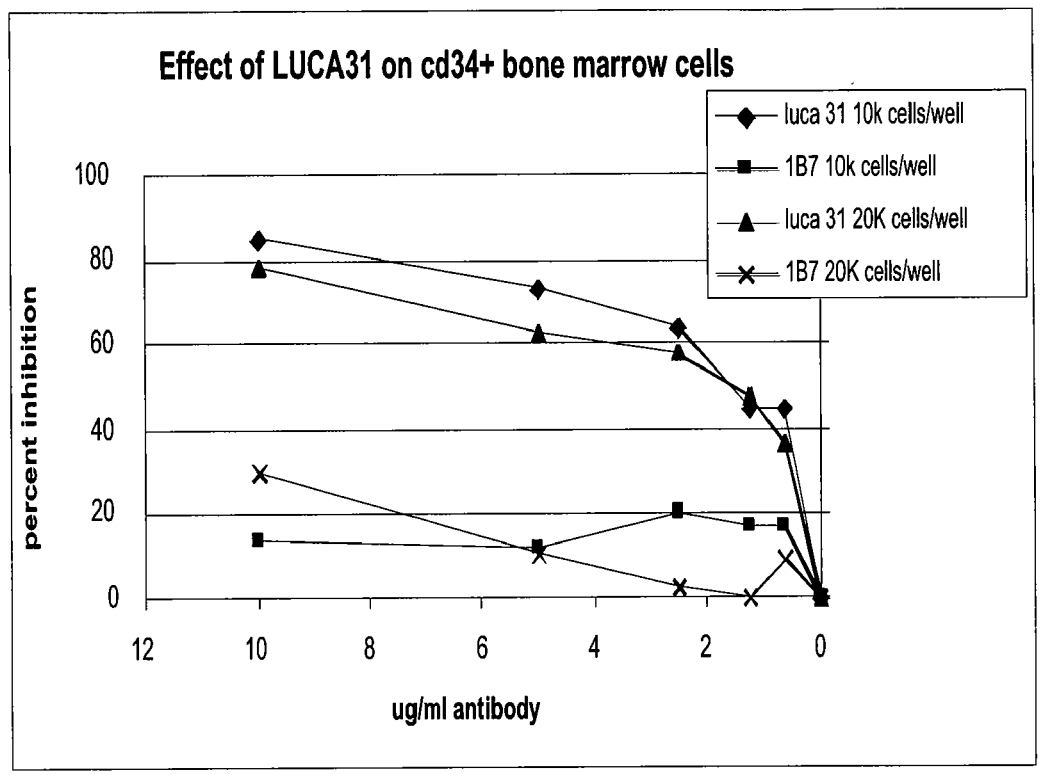
FIG. 15 shows the effect of LUCA31 on CD34+ bone marrow progenitor cells. LUCA31 and the control IgG1 antibody 1B7.11 were compared in a cell proliferation assay using two seeding densities of bone marrow progenitor cells.

To evaluate the effect of LUCA31 on bone marrow progenitor cells we performed a similar assay, this time using CD34 selected human bone marrow derived cells stimulated with a cytokine/growth factor cocktail that included EPO, IL-3, SCF and GM-CSF. For this experiment we compared LUCA31 to the control IgG1 antibody 1B7.11 using two different cell seeding densities. The results of this experiment (FIG. 15) show that LUCA31 reduced cell proliferation to 20% of control levels. In comparison, the control antibody had a modest effect. Taken together, these experiments indicate that LUCA31 can potently inhibit the proliferation of both tumor cells, as well as normal cells derived from both the peripheral blood and bone marrow compartments.

The effect of LUCA31 on the bone marrow derived cells is particularly important to note, considering the potential toxicity liability. As discussed above, there was some evidence of bone marrow suppression in a human phase I trial of the transferrin receptor antibody 42-6 (Brooks et al., 1995). Our data is consistent with the idea that LUCA31, like other transferrin receptor antibodies, can inhibit tumor cell proliferation, but may also impact the proliferation of bone marrow progenitor cell populations. However, it is believed that LUCA31 has significantly reduce toxicity, relative to previously known transferrin receptor antibodies.

Example 21

In Vivo Biology

Figure 16:
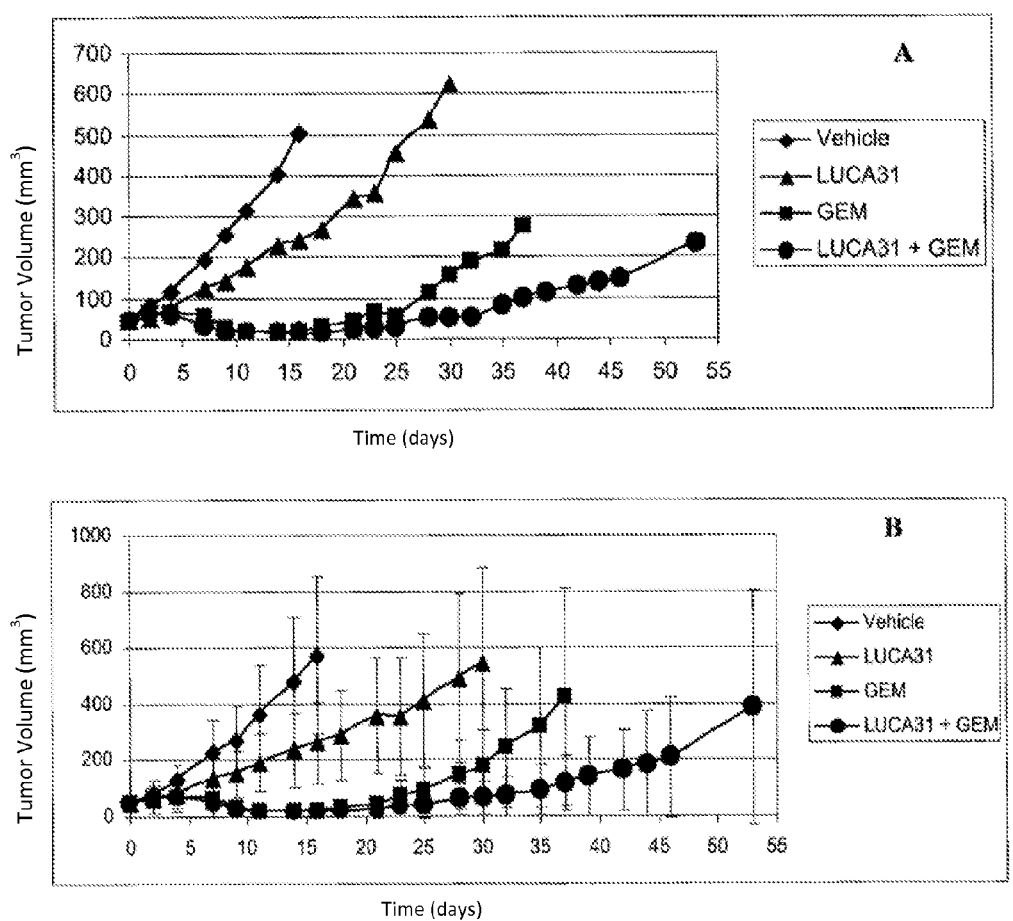
FIG. 16 shows the effect of LUCA31 on HCT15 tumor growth.

The results of our in vitro studies with tumor derived cell lines showed LUCA31 has broad activity within the panel of cell lines that we have translated into xenograft models. LUCA31 was particularly active in blocking the proliferation of the colon carcinoma cell line HCT15. Based on these results we chose to test the effect of LUCA31 in an established HCT15 tumor xenograft model alone, and in combination with gemcitabine. In this study, groups of 15 mice were treated twice weekly with 500 ug of antibody for four weeks. Gemcitabine was dosed on a q3d ×2 schedule at 120 mg/kg, which is near the MID. Treatment was initiated when tumor volumes averaged 70 mm$^3$. The results of this study are shown in FIG. 16. In FIG. 16A, the median tumor volumes are shown and in FIG. 16B, the mean tumor volumes with error bars are presented. In this experiment, the LUCA31 antibody produced a tumor growth delay of greater than 14 days, relative to the saline control. Gemcitabine produced a 20-day tumor growth delay and the combination of LUCA31 and gemcitabine produced a tumor growth delay of 18 days relative to gemcitabine alone.

The results of this experiment indicate the LUCA31 antibody is active in this tumor model and the data compares favorably with cetuximab in colorectal tumor models. Based on what we understand about LUCA31, and without being limited to a particular mechanism, it is presently believed that the effect of this antibody on tumor cells is driven primarily through intrinsic activities mediated through its interaction with the transferrin receptor. Because LUCA31 is a mouse IgG1 molecule and the Fc domain of this isotype has low affinity for Fc receptors, ADCC mediated destruction of tumor cells is unlikely to contribute substantially to the tumor growth delay.

An antibody with increased affinity to mouse Fc receptors may be more effective at controlling tumor growth, via receptor cross linking as well as via enhanced immune effector function. To address this concept, a human chimeric LUCA31 molecule that contains the human IgG1 Fc domain has been made.

Materials and Methods Referenced in the Examples:
Luca31 V Region Cloning and Expression Vector Construction Introduction: Luca31 RNA was extracted from hybridoma cell lines expressing the mouse antibody and the variable regions of heavy and light chains were pulled out by RT-PCR from cDNA. The V-regions were inserted into CHEF1 mammalian expression vectors.

Materials and Methods
RNA Extraction:
The QIAGEN RNeasy Mini Kit (Cat No 74106) was used to extract RNA from frozen hybridoma cell pellets.
cDNA:
Roche's "1$^{st}$ Strand cDNA Synthesis Kit for RT-PCR (AMV)" (Cat No 1 483 188) was used to generate cDNA. The reaction was run with and without RT to generate a negative control for the PCR reaction.
RT-PCR:
PCR was carried out on the cDNA template, using Padma's "ShortPCR" program, and reagents from Clontech's Advantage PCR kit.
2 µl cDNA reaction
5 µl 10× buffer
2 µl each primer
1 µl dNTP mix
1 µl Advantage polymerase
dH2O to 50 µl Negative controls (no RT cDNA) were run for each primer combination. The degenerate primers used contain sequence for the signal sequences rather than simply the CH1 domain of the V regions. MVH.1 (SEQ ID NO:11), MVH.2 (SEQ ID NO:12), MVH.3 (SEQ ID NO:13), MVH.4 (SEQ ID NO:14), MVH.5 (SEQ ID NO:15), MVH.6 (SEQ ID NO:16), MVH.7 (SEQ ID NO:17), MVH.8 (SEQ ID NO:18), MVH.9 (SEQ ID NO:19), MVH.10 (SEQ ID NO:20), MVH.11 (SEQ ID NO:21), MVH.12 (SEQ ID NO:22), MVL.1 (SEQ ID NO:23), MVL.2 (SEQ ID NO:24), MVL.3 (SEQ ID NO:25), MVL.4 (SEQ ID NO:26), MVL.5 (SEQ ID NO:27), MVL.6 (SEQ ID NO:28), MVL.7 (SEQ ID NO:29), MVL.8 (SEQ ID NO:30), MVL.9 (SEQ ID NO:31), MVL.10 (SEQ ID NO:32), MVL.11 (SEQ ID NO:33), MVL.rev (SEQ ID NO:34), MVH.rev1 (SEQ ID NO:35), and MVH.rev2 (SEQ ID NO:36) are shown below:

```
Degenerate Primers for mouse antibody V regions
MVH.1      ACTAGTCGACATGAAATGCAGCTGGGTCATSTTCTTC

MVH.2      ACTAGTCGACATGGGATGGAGCTRTATCATSYTCTT

MVH.3      ACTACTCGACATGAAGWTGTGGTTAAACTGGGTTTTT

MVH.4      ACTAGTCGACATGRACTTTGGGYTCAGCTTGRTTT

MVH.5      ACTAGTCGACATGGACTCCAGGCTCAATTTAGTTTTCCTT

MVH.6      ACTAGTCGACATGGCTGTCYTRGSGCTRCTCTTCTGC

MVH.7      ACTAGTCGACATGGRATGGAGCKGGRTCTTTMTCTT

MVH.8      ACTAGTCGACATGAGAGTGCTGATTCTTTTGTG

MVH.9      ACTAGTCGACATGGMTTGGGTGTGGAMCTTGCTATTCCTG

MVH.10     ACTAGTCGACATGGGCAGACTTACATTCTCATTCCTG

MVH.11     ACTAGTCGACATGGATTTTGGGCTGATTTTTTTATTG

MVH.12     ACTAGTCGACATGATGGTGTTAAGTCTTCTGTACCTG

MVL.1      ACTAGTCGACATGAAGTTGCCTGTTAGGCTGTTGGTGCTG

MVL.2      ACTAGTCGACATGGAGWCAGACACACTCCTGYTATGGGT

MVL.3      ACTAGTCGACATGAGTGTGCTCACTCAGGTCCTGGSGTTG

MVL.4      ACTAGTCGACATGAGGRCCCCTGCTCAGWTTYTTGGMWTCTTG

MVL.5      ACTAGTCGACATGGATTTWCAGGTGCAGATTWTCAGCTTC

MVL.6      ACTAGTCGACATGAGGTKCYYTGYTSAGYTYCTGRGG

MVL.7      ACTAGTCGACATGGGCWTCAAGATGGAGTCACAKWYYCWGG

MVL.8      ACTAGTCGACATGTGGGGAYCTKTTTYCMMTTTTTCAATTG

MVL.9      ACTAGTCGACATGGTRTCCWCASCTCAGTTCCTTG

MVL.10     ACTAGTCGACATGTATATATGTTTGTTGTCTATTTCT
```

```
MVL.11      ACTAGTCGACATGGAAGCCCCAGCTCAGCTTCTCTTCC

MVL.rev     TACGACCCGGGACTGGATGGTGGGAAGATGGA

MVH.rev1    TACGACCCGGGGGAGTTAGTTTGGGCAGCAGATCC

MVH.rev2    TACGACCCGGGAGCAGATCCAGGGGCCAGTGGATA
```

Vector Construction:

Restriction enzymes and ligase used were purchased from Roche, NEB or Promega. Ligations were transformed into chemically competent XL10-Gold cells from Stratagene and plated on LBM/Carb agarose plates. Colonies were picked into LBM with either 100 or 50 µg/ml carbenicillin for mini preps.

Mini-preps and maxi-preps were done with QIAGEN kits. For maxi preps of large vectors (pDEF14 and pNEF5), 200 ml overnight cultures were grown up and the cells were pelleted. QIAGEN's protocol was followed, doubling all volumes of P1, P2 and P3 as if preparing 2×100 ml cultures. Following the first spin, all supernatants were applied to one column, effectively concentrating DNA yields. The expression vectors were sequenced through the coding regions prior to transfection in CHO cells and were analyzed by restriction digest.

Tissue Analysis of LUCA31 Staining

LUCA31 and commercial transferrin receptor antibodies were assessed using frozen tissue sections. Tissue sections were fixed for 10 minutes in 100% acetone at −20 C, then placed in wash buffer prior to the first blocking solution step. Wash buffer=1×TBS with 0.05% Tween 20/Diluent=20% human serum, 2% BSA in wash buffer.

Staining Protocol:
1) H2O2 Block: DAKO Peroxidase Blocking Reagent, cat# 003715, 15 minutes
2) Protein Block: 20% human serum, 2% BSA in wash buffer
3) Avidin/Biotin Block: Vector cat# sp-2001, 15 minutes with Avidin (A) Rinse ×2 wash/15 minutes with
4) Biotin (B) blot off and add primary antibody.
5) 1° Antibody: (see table) 1 hour
6) Wash ×3 after 1°
7) 3° (see table) 30 minutes/Wash ×3
8) DAB: DAKO DAB+, Cat# K3468, 1 drop DAB per ml of supplied buffer. (package instruction) Stop reaction with H2O when developed.
9) Counterstain: Gills Hematoxylin, 1 quick dip followed by several rinses. Blue 5 minutes in tap H2O.
10) Dehydrate to xylene and coverslip with mounting medium.

| Slide Id | 1° and 2° |
|---|---|
| #1 H1696.02.02 Liver | Zymed H68.4 mouse IgG1 anti-human TR (Cat# 13-6800, used at 10 µg/ml 2&3°: Mouse envision cat# K4001 |
| #2 H1696.02.02 Liver | Santa Cruz BER-T9 mouse IgG1 anti-human TR (Cat# sc-19675), used at 10 µg/ml 2&3°: Mouse envision cat# K4001 |
| #3 H1696.02.02 Liver | Abcam DF1513 mouse IgG1 anti-human TR antibody (cat# ab223), used at 10 µg/ml 2&3°: Mouse envision cat# K4001 |
| #4 H1696.02.02 Liver | Luca 31 mouse IgG1 used at 0.10 µg/ml 2&3°: Mouse envision cat# K4001 |
| #5 H1696.02.01 Liver | Zymed H68.4 mouse IgG1 anti-human TR (Cat# 13-6800, used at 10 µg/ml 2&3°: Mouse envision cat# K4001 |
| #6 H1696.02.01 Liver | Santa Cruz BER-T9 mouse IgG1 anti-human TR (Cat# sc-19675), used at 10 µg/ml 2&3°: Mouse envision cat# K4001 |
| #7 H1696.02.01 Liver | Abcam DF1513 mouse IgG1 anti-human TR antibody (cat# ab223), used at 10 µg/ml 2&3°: Mouse envision cat# K4001 |
| #8 H1696.02.01 Liver | Luca 31, used at .10 µg/ml 2&3°: Mouse envision cat# K4001 |
| #9 H1696.02.01 Liver | Luca 31, used at 10 µg/ml 2&3°: Mouse envision cat# K4001 |
| #10 H1689.01.01 Liver | Zymed H68.4 mouse IgG1 anti-human TR (Cat# 13-6800, used at 10 µg/ml 2&3°: Mouse envision cat# K4001 |
| #11 H1689.01.01 Liver | Santa Cruz BER-T9 mouse IgG1 anti-human TR (Cat# sc-19675), used at 10 µg/ml 2&3°: Mouse envision cat# K4001 |
| #12 H1689.01.01 Liver | Abcam DF1513 mouse IgG1 anti-human TR antibody (cat# ab223), used at 10 µg/ml 2&3°: Mouse envision cat# K4001 |
| #13 H1689.01.01 Liver | Luca 31, used at 0.10 µg/ml 2&3°: Mouse envision cat# K4001 |
| #14 H1689.01.01 Liver | Luca 31, used at 10 µg/ml 2&3°: Mouse envision cat# K4001 |
| #15 H3112.01.02 Colon | Zymed H68.4 mouse IgG1 anti-human TR (Cat# 13-6800, used at 10 µg/ml 2&3°: Mouse envision cat# K4001 |
| #16 H3112.01.02 Colon | Santa Cruz BER-T9 mouse IgG1 anti-human TR (Cat# sc-19675), used at 10 µg/ml 2&3°: Mouse envision cat# K4001 |
| #17 H3112.01.02 Colon | Abcam DF1513 mouse IgG1 anti-human TR antibody (cat# ab223), used at 10 µg/ml 2&3°: Mouse envision cat# K4001 |
| #18 H3112.01.02 Colon | Luca 31, used at .10 µg/ml 2&3°: Mouse envision cat# K4001 |
| #19 H2208.01.01 Pancreas | Zymed H68.4 mouse IgG1 anti-human TR (Cat# 13-6800, used at 10 µg/ml 2&3°: Mouse envision cat# K4001 |
| #20 H2208.01.01 Pancreas | Santa Cruz BER-T9 mouse IgG1 anti-human TR (Cat# sc-19675), used at 10 µg/ml 2&3°: Mouse envision cat# K4001 |
| #21 H2208.01.01 Pancreas | Abcam DF1513 mouse IgG1 anti-human TR antibody (cat# ab223), used at 10 µg/ml 2&3°: Mouse envision cat# K4001 |
| #22 H2208.01.01 Pancreas | Luca 31, used at 0.10 µg/ml 2&3°: Mouse envision cat# K4001 |
| #23 H2208.01.01 Pancreas | Luca 31, used at 10 µg/ml 2&3°: Mouse envision cat# K4001 |
| #24 H1138.10.03 Pancreas | Zymed H68.4 mouse IgG1 anti-human TR (Cat# 13-6800, used at 10 µg/ml 2&3°: Mouse envision cat# K4001 |
| #25 H1138.10.03 Pancreas | Santa Cruz BER-T9 mouse IgG1 anti-human TR (Cat# sc-19675), used at 10 µg/ml 2&3°: Mouse envision cat# K4001 |
| #26 H1138.10.03 Pancreas | Abcam DF1513 mouse IgG1 anti-human TR antibody (cat# ab223), used at 10 µg/ml 2&3°: Mouse envision cat# K4001 |
| #27 H1138.10.03 Pancreas | Luca 31, used at 0.10 µg/ml 2&3°: Mouse envision cat# K4001 |
| #28 H1138.10.03 Pancreas | Luca 31, used at 10 µg/ml 2&3°: Mouse envision cat# K4001 |
| #29 H1194.04.01 Pancreas | Zymed H68.4 mouse IgG1 anti-human TR (Cat# 13-6800, used at 10 µg/ml 2&3°: Mouse envision cat# K4001 |
| #30 H1194.04.01 Pancreas | Santa Cruz BER-T9 mouse IgG1 anti-human TR (Cat# sc-19675), used at 10 µg/ml 2&3°: Mouse envision cat# K4001 |

| Slide Id | 1° and 2° |
|---|---|
| #31 H1194.04.01 Pancreas | Abcam DF1513 mouse IgG1 anti-human TR antibody (cat# ab223),, used at 10 µg/ml<br>2&3°: Mouse envision cat# K4001 |
| #32 H1194.04.01 Pancreas | Luca 31, used at 0.10 µg/ml<br>2&3°: Mouse envision cat# K4001 |
| #33 H1289.03.03 Brain | Zymed H68.4 mouse IgG1 anti-human TR (Cat# 13-6800, used at 10 µg/ml<br>2&3°: Mouse envision cat# K4001 |
| #34 H1289.03.03 Brain | Santa Cruz BER-T9 mouse IgG1 anti-human TR (Cat# sc-19675), used at 10 µg/ml<br>2&3°: Mouse envision cat# K4001 |
| #35 H1289.03.03 Brain | Abcam DF1513 mouse IgG1 anti-human TR antibody (cat# ab223),, used at 10 µg/ml<br>2&3°: Mouse envision cat# K4001 |
| #36 H1289.03.03 Brain | Luca 31, used at 0.10 µg/ml<br>2&3°: Mouse envision cat# K4001 |
| #37 H1289.03.03 Brain | Luca 31, used at 10 µg/ml<br>2&3°: Mouse envision cat# K4001 |
| #38 H1138.04.05 Brain | Zymed H68.4 mouse IgG1 anti-human TR (Cat# 13-6800, used at 10 µg/ml<br>2&3°: Mouse envision cat# K4001 |
| #39 H1138.04.05 Brain | Santa Cruz BER-T9 mouse IgG1 anti-human TR (Cat# sc-19675), used at 10 µg/ml<br>2&3°: Mouse envision cat# K4001 |
| #40 H1138.04.05 Brain | Abcam DF1513 mouse IgG1 anti-human TR antibody (cat# ab223),, used at 10 µg/ml<br>2&3°: Mouse envision cat# K4001 |
| #41 H1138.04.05 Brain | Luca 31, used at 0.10 µg/ml<br>2&3°: Mouse envision cat# K4001 |

Antibody Bioassay

Assay performed in 96 well flat bottom tissue culture plates.

Day 1:

Prepare cells to use: # cells plated depends on the cell line (1000-6000/well);

Add cells to the wells in a volume of 200 ul RPMI1640+ 10% fetal bovine serum (FBS).

Incubate overnight @37° C.

Day 2

Aspirate media from wells and add back 150 ul complete media, then 50 ul of 4× antibody dilutions (10 ug/ml, 5 ug/ml, 2.5 ug/ml, 1.25 ug/ml. 0.6 ug/ml) or negative control. Perform antibody dilutions in triplicate.

Incubate overnight @37° C.

Day 3 continue incubation at 37° C. for 48 hrs

Day 5

Note—before pulsing, spin the plates with semi-adherent cells (e.g. Colo205)

Pulse with 1 uCi of $^3$H-thymidine (in 20 ul complete growth medium)

Incubate from 6 hours to overnight

Day 6

Add 20 ul of 0.5% SDS (made in D-PBS) to wells—final conc. of SDS is 0.05%

Freeze the cells in the freezer −80° C. for about 60 minutes

Harvest and count tritiated thymidine incorporation in cellular DNA

Expression of Human Transferrin Receptor in CHO Cells and Staining with LUCA 31

Human transferrin receptor was PCR amplified from human cDNA using the following primers:

```
                                        (SEQ ID NO: 37)
5'-GAA TTC TGC AGG GGA TCC GCC ACC ATG ATG GAT
CAA GCT AGA TCA GCA TTC TC-3'

(SEQ ID NO: 38)
5'-CTC GAG CGG CCG CCA CTG TTA AAA CTC ATT GTC
AAT GTC CC-3'
``` and the full length transferrin receptor gene was cloned into a modified pDEF2 vector to create the expression vector TFRC-pDEF99TORA. The TFRC-pDEF99TORA expression construct was transfected in to CHO cells using Minis TransIT transfection reagents and by electroporation using Pvu I digested linear plasmid. Cells were selected by limited dilution. Applicable methods disclosed in U.S. Pat. No. 5,888,809 are hereby incorporated by reference.

To evaluate LUCA31 staining, cell lines were subjected to FACS and florescent microscopy. An aliquot of cells were incubated on ice for 30 min with LUCA31 antibody diluted to 100 ng/ml, washed and then incubated with a 1:200 dilution of a FITC conjugate anti-mouse antibody. The washed cells were then evaluated by FACS or directly viewed using the fluorescent microscope. No detection of florescent staining was seen in the untransfected CHO cells or in CHO cells transfected with vector alone. A 50 fold signal over background was detected using the FL 1 channel by FACS in the cells transfected with the TFRC-pDEF99TORA vector relative to the expression vector alone.

FACS Analysis:

FACS buffer (D-PBS+0.1% BSA)

BSA (endotoxin free)

mouse IgG FITC conjugate (Sigma #F-2883—1:200 dilution in FACS buffer)

1% Formaldehyde (in D-PBS)

FACS tubes (Falcon #2052)

96 well, polystyrene, round bottom, cell culture plate (Corning/Costar #3799)

Protocol

Resuspend cells in 200_l D-PBS

Vortex gently.

Add 50_l appropriate reagent (antibody, isotype control, media . . . ) to each well and vortex gently.

Incubate on ice/30 minutes.

Centrifuge (1100 RPM/5 minutes) and remove (flick) media.

Vortex gently.

Wash once in 200_l D-PBS (centrifuge, flick, vortex gently).

Resuspend in 200_l_-mouse IgG FITC conjugate (1:200 dilution in FACS buffer) and vortex gently.

Incubate in the dark (foil), on ice/30 minutes.

Centrifuge (1100 RPM/5 minutes) and remove (flick) media.

Vortex gently.

Wash once in 200_l D-PBS (centrifuge, flick, vortex gently).

Resuspend in 200_l 1% formaldehyde (in D-PBS) and transfer to FACS tubes.

Read FL1 fluorescence intensity on FACS.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application was specifically and individually indicated to be so incorporated by reference.

We claim:

1. A method for delivering a chemotherapeutic agent to a cancer cell comprising administering a composition comprising an antibody or antigen-binding fragment thereof, wherein said antibody or fragment comprises three complementarity determining regions from the light chain and three complementarity determining regions from the heavy chain, said antibody or fragment thereof is capable of binding to LUCA31 epitope which does not overlap with transferrin binding, and said LUCA31 epitope is the epitope bound by antibody expressed by hybridoma cell line having ATCC No. PTA-6055, associated with the chemotherapeutic agent, wherein the cancer cell is selected from the group consisting of cancer cells from adrenal gland tumors, AIDS-associated cancers, alveolar soft part sarcoma, astrocytic tumors, bladder cancer, bone cancer, brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's sarcoma, kidney cancer, leukemias, lipoma/benign lipomatous tumors, liposarcoma/malignant lipomatous tumors, liver cancer, lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, uveal or intraocular melanoma, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers.

2. The method of claim 1, wherein the chemotherapeutic agent is administered to an individual.

3. The method of claim 1, wherein the antibody is an antibody expressed by hybridoma ATCC No. PTA-6055 or progeny thereof.

4. A method of inhibiting growth of cancer cells in an individual comprising administering to the individual an effective amount of a composition comprising an antibody or antigen-binding fragment thereof, wherein said antibody or fragment comprises three complementarity determining regions from the light chain and three complementarity determining regions from the heavy chain, said antibody or fragment thereof is capable of binding to LUCA31 epitope which does not overlap with transferrin binding, and said LUCA31 epitope is the epitope bound by antibody expressed by hybridoma cell line having ATCC No. PTA-6055, associated with a chemotherapeutic agent to the individual, wherein the cancer cells are selected from the group consisting of cancer cells from adrenal gland tumors, AIDS-associated cancers, alveolar soft part sarcoma, astrocytic tumors, bladder cancer, bone cancer, brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's sarcoma, kidney cancer, leukemias, lipoma/benign lipomatous tumors, liposarcoma/malignant lipomatous tumors, liver cancer, lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, uveal or intraocular melanoma, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers.

5. The method of claim 4, wherein the chemotherapeutic agent is delivered into the cancer cells.

6. The method of claim 4, wherein the antibody is expressed by hybridoma ATCC No. PTA-6055 or progeny thereof.

7. The method of claim 1, wherein the antibody comprises an antigen-binding fragment of the antibody expressed by the hybridoma ATCC No. PTA-6055 or progeny thereof.

8. The method of claim 1, wherein the antibody comprises the three complementarity determining regions from the light chain and the three complementarity determining regions from the heavy chain of antibody LUCA31 expressed by the hybridoma having ATCC No. PTA-6055 or progeny thereof.

9. The method of claim 8, wherein the antibody is a chimeric antibody.

10. The method of claim 8, wherein the antibody is a humanized antibody.

11. The method of claim 8, wherein the antibody is a chimeric antibody comprising the heavy chain and the light chain variable region sequences from antibody LUCA31 produced by the cell line having ATCC No. PTA-6055 or progeny thereof.

12. The method of claim 11, wherein the antibody comprises the heavy chain constant region sequence and the light chain constant region sequence from a human antibody.

13. The method of claim 1, wherein the antibody comprises the heavy chain variable region sequence from antibody LUCA31 produced by the cell line having ATCC No. PTA-6055 or progeny thereof.

14. The method of claim 1, wherein the antibody comprises the light chain variable region sequence from antibody LUCA31 produced by the cell line having ATCC No. PTA-6055 or progeny thereof.

15. The method of claim 8, wherein the antibody comprises an antigen-binding fragment; wherein the antigen-binding fragment is selected from the group consisting of a Fab, a Fab', a F(ab')2 and a Fv; and wherein the antigen-binding fragment retains the binding specificity of antibody LUCA31 produced by the cell line having ATCC No. PTA-6055 or progeny thereof.

16. The method of claim 4, wherein the antibody comprises an antigen-binding fragment of the antibody expressed by the hybridoma ATCC No. PTA-6055 or progeny thereof.

17. The method of claim 4, wherein the antibody comprises the three complementarity determining regions from the light chain and the three complementarity determining regions from the heavy chain of antibody LUCA31 expressed by the hybridoma having ATCC No. PTA-6055 or progeny thereof.

18. The method of claim 17, wherein the antibody is a chimeric antibody.

19. The method of claim 17, wherein the antibody is a humanized antibody.

20. The method of claim 17, wherein the antibody is a chimeric antibody comprising the heavy chain and the light chain variable region sequences from antibody LUCA31 produced by the cell line having ATCC No. PTA-6055 or progeny thereof.

21. The method of claim 20, wherein the antibody comprises the heavy chain constant region sequence and the light chain constant region sequence from a human antibody.

22. The method of claim 4, wherein the antibody comprises the heavy chain variable region sequence from antibody LUCA31 produced by the cell line having ATCC No. PTA-6055 or progeny thereof.

23. The method of claim 4, wherein the antibody comprises the light chain variable region sequence from antibody LUCA31 produced by the cell line having ATCC No. PTA-6055 or progeny thereof.

24. The method of claim 17, wherein the antibody comprises an antigen-binding fragment; wherein the antigen-binding fragment is selected from the group consisting of a Fab, a Fab', a F(ab')2 and a Fv; and wherein the antigen-binding fragment retains the binding specificity of antibody LUCA31 produced by the cell line having ATCC No. PTA-6055 or progeny thereof.

* * * * *

SEQUENCE LISTING

<160> NUMBER OF SEQ ID NOS: 38

<210> SEQ ID NO 1
<211> LENGTH: 40
<212> TYPE: DNA
<213> ORGANISM: Artificial Sequence
<220> FEATURE:
<223> OTHER INFORMATION: Synthetic construct

<400> SEQUENCE: 1
gaaaaccaag cttaccgcca ccatggattt tcaggtgcag                40

<210> SEQ ID NO 2
<211> LENGTH: 36
<212> TYPE: DNA
<213> ORGANISM: Artificial Sequence
<220> FEATURE:
<223> OTHER INFORMATION: Synthetic construct

<400> SEQUENCE: 2
cgggaagatg aagacagatg gtgcagcatc agcccg                   36

<210> SEQ ID NO 3
<211> LENGTH: 40
<212> TYPE: DNA
<213> ORGANISM: Artificial Sequence
<220> FEATURE:
<223> OTHER INFORMATION: Synthetic construct

<400> SEQUENCE: 3
gaaaaccaag cttgccgcca ccatggattg ggtgtggaac                40

<210> SEQ ID NO 4
<211> LENGTH: 36
<212> TYPE: DNA
<213> ORGANISM: Artificial Sequence
<220> FEATURE:
<223> OTHER INFORMATION: Synthetic construct

<400> SEQUENCE: 4
gcccttggtg ctagctgcag agacagtgac cagagt                   36

<210> SEQ ID NO 5
<211> LENGTH: 446
<212> TYPE: DNA
<213> ORGANISM: Mus musculus

<400> SEQUENCE: 5
gggacgtcga catggatttt caggtgcaga ttttcagctt cctgctaatc agtatctcag        60
ttgtaatgtc cagaggagaa aatgtgctca cccagtctcc agcaatcatg tctgcatctc       120
taggggagaa ggtcaccatg agctgcaggg ccagctcaag tgtaaattac atatactggt       180
accagcagaa gtcagatgcc tcccccaaac tgtggattta tcacacatcc aacctggctc       240
tggagtccc agctcgcttc agtggcagtg ggtctgggaa ctcttattct ctcacaatca       300
gcagcatgga gggtgaagat gctgccactt attactgcca gcagtttact agttccccgt       360
ggacgttcgg tggaggcacc aagctggaaa tcaaacgggc tgatgctgca ccaactgtat       420
ccatcttccc accatccagt cccggg                                           446

<210> SEQ ID NO 6
<211> LENGTH: 435
<212> TYPE: DNA

<213> ORGANISM: Mus musculus

<400> SEQUENCE: 6

```
atggattttc aggtgcagat tttcagcttc ctgctaatca gtatctcagt tgtaatgtcc      60
agaggagaaa atgtgctcac ccagtctcca gcaatcatgt ctgcatctct aggggagaag     120
gtcaccatga gctgcagggc cagctcaagt gtaaattaca tatactggta ccagcagaag     180
tcagatgcct cccccaaact gtggatttat cacacatcca acctggctcc tggagtccca     240
gctcgcttca gtggcagtgg gtctgggaac tcttattctc tcacaatcag cagcatggag     300
ggtgaagatg ctgccactta ttactgccag cagtttacta gttccccgtg gacgttcggt     360
ggaggcacca agctggaaat caaacgggct gatgctgcac caactgtatc catcttccca     420
ccatccagtc ccggg                                                     435
```

<210> SEQ ID NO 7
<211> LENGTH: 433
<212> TYPE: DNA
<213> ORGANISM: Mus musculus

<400> SEQUENCE: 7

```
gaattcgccc ttactagtcg acatggattg ggtgtggaac ttgctattcc tgatggcagc      60
tgcccaaagt gcccaagcac agatccagtt ggtgcagtct ggacctgagc tgaagaagcc     120
tggagagaca gtcaagatct cctgcaaggc ttctgggtat accttcacaa actatggaat     180
gaactgggtg aagcaggctc aggaaaaggg tttacagtgg atgggctgga taaacaccta     240
cactggagaa ccaacatatg ctggtgactt caagggacgg tttgccttct ctttggaaac     300
ctctgccagc actgcctatt tgcagatcaa catcctcaaa aatgaggaca cggctacata     360
tttctgttca agagacgggg gtaactaccc ttttgcttac tggggccagg ggactctggt     420
cactgtctct gca                                                       433
```

<210> SEQ ID NO 8
<211> LENGTH: 417
<212> TYPE: DNA
<213> ORGANISM: Mus musculus

<400> SEQUENCE: 8

```
gtcgacatgg attgggtgtg gaacttgcta ttcctgatgg cagctgccca agtgcccaa       60
gcacagatcc agttggtgca gtctggacct gagctgaaga agcctggaga gacagtcaag     120
atctcctgca aggcttctgg gtataccttc acaaactatg aatgaactgg ggtgaagcag     180
gctccaggaa agggtttaca gtggatgggc tggataaaca cctacactgg agaaccaaca     240
tatgctggtg acttcaaggg acggtttgcc ttctctttgg aaacctctgc cagcactgcc     300
tatttgcaga tcaacatcct caaaaatgag gacacggcta catatttctg ttcaagagac     360
ggggtaact accctttgc ttactggggc caggggactc tggtcactgt ctctgca         417
```

<210> SEQ ID NO 9
<211> LENGTH: 423
<212> TYPE: DNA
<213> ORGANISM: Mus musculus

<400> SEQUENCE: 9

```
tgggacgtcg acatggattg ggtgtggaac ttgctattcc tgatggcagc tgcccaaagt      60
gcccaagcac agatccagtt ggtgcagtct ggacctgagc tgaagaagcc tggagagaca     120
gtcaagatct cctgcaaggc ttctgggtat accttcacaa actatggaat gaactgggtg     180
```

-continued

```
aagcaggctc caggaaaggg tttacagtgg atgggctgga taaacaccta cactggagaa    240
ccaacatatg ctggtgactt caagggacgg tttgccttct ctttggaaac ctctgccagc    300
actgcctatt tgcagatcaa catcctcaaa aatgaggaca cggctacata tttctgttca    360
agagacgggg gtaactaccc ttttgcttac tggggccagg ggactctggt cactgtctct    420
gca                                                                  423
```

<210> SEQ ID NO 10
<211> LENGTH: 433
<212> TYPE: DNA
<213> ORGANISM: Mus musculus

<400> SEQUENCE: 10

```
gaattcgccc tkrswmgtcg acatggattg ggtgtggaac ttgctattcc tgatggcagc     60
tgcccaaagt gcccaagcac agatccagtt ggtgcagtct ggacctgagc tgaagaagcc    120
tggagagaca gtcaagatct cctgcaaggc ttctgggtat accttcacaa actatgGaat    180
gaactgggtg aagcaggctc aggaaaggg tttacagtgg atgggctgga taaacaccta    240
cactggagaa ccaacatatg ctggtgactt caagggacgg tttgccttct ctttggaaac    300
ctctgccagc actgcctatt tgcagatcaa catcctcaaa aatgaggaca cggctacata    360
tttctgttca agagacgggg gtaactaccc ttttgcttac tggggccagg ggactctggt    420
cactgtctct gca                                                       433
```

<210> SEQ ID NO 11
<211> LENGTH: 37
<212> TYPE: DNA
<213> ORGANISM: Artificial Sequence
<220> FEATURE:
<223> OTHER INFORMATION: Synthetic construct
<220> FEATURE:
<223> OTHER INFORMATION: s = g or c

<400> SEQUENCE: 11

```
actagtcgac atgaaatgca gctgggtcat sttcttc                              37
```

<210> SEQ ID NO 12
<211> LENGTH: 36
<212> TYPE: DNA
<213> ORGANISM: Artificial Sequence
<220> FEATURE:
<223> OTHER INFORMATION: Synthetic construct
<220> FEATURE:
<223> OTHER INFORMATION: r = g or a
<220> FEATURE:
<223> OTHER INFORMATION: s = g or c
<220> FEATURE:
<223> OTHER INFORMATION: y = t or c

<400> SEQUENCE: 12

```
actagtcgac atgggatgga gctrtatcat sytctt                               36
```

<210> SEQ ID NO 13
<211> LENGTH: 37
<212> TYPE: DNA
<213> ORGANISM: Artificial Sequence
<220> FEATURE:
<223> OTHER INFORMATION: Synthetic construct
<220> FEATURE:
<223> OTHER INFORMATION: w = a or t

<400> SEQUENCE: 13

```
actagtcgac atgaagwtgt ggttaaactg ggttttt                              37
```

```
<210> SEQ ID NO 14
<211> LENGTH: 35
<212> TYPE: DNA
<213> ORGANISM: Artificial Sequence
<220> FEATURE:
<223> OTHER INFORMATION: Synthetic construct
<220> FEATURE:
<223> OTHER INFORMATION: r = g or a
<220> FEATURE:
<223> OTHER INFORMATION: y = t or c

<400> SEQUENCE: 14
actagtcgac atgractttg ggytcagctt grttt                              35

<210> SEQ ID NO 15
<211> LENGTH: 40
<212> TYPE: DNA
<213> ORGANISM: Artificial Sequence
<220> FEATURE:
<223> OTHER INFORMATION: Synthetic construct

<400> SEQUENCE: 15
actagtcgac atggactcca ggctcaattt agttttcctt                         40

<210> SEQ ID NO 16
<211> LENGTH: 37
<212> TYPE: DNA
<213> ORGANISM: Artificial Sequence
<220> FEATURE:
<223> OTHER INFORMATION: Synthetic construct
<220> FEATURE:
<223> OTHER INFORMATION: y = t or c
<220> FEATURE:
<223> OTHER INFORMATION: r = g or a
<220> FEATURE:
<223> OTHER INFORMATION: s = g or c

<400> SEQUENCE: 16
actagtcgac atggctgtcy trgsgctrct cttctgc                            37

<210> SEQ ID NO 17
<211> LENGTH: 36
<212> TYPE: DNA
<213> ORGANISM: Artificial Sequence
<220> FEATURE:
<223> OTHER INFORMATION: Synthetic construct
<220> FEATURE:
<223> OTHER INFORMATION: r = g or a
<220> FEATURE:
<223> OTHER INFORMATION: k = g or t
<220> FEATURE:
<223> OTHER INFORMATION: m = a or c

<400> SEQUENCE: 17
actagtcgac atggratgga gckggrtctt tmtctt                             36

<210> SEQ ID NO 18
<211> LENGTH: 33
<212> TYPE: DNA
<213> ORGANISM: Artificial Sequence
<220> FEATURE:
<223> OTHER INFORMATION: Synthetic construct

<400> SEQUENCE: 18
actagtcgac atgagagtgc tgattctttt gtg                                33

<210> SEQ ID NO 19
<211> LENGTH: 40
<212> TYPE: DNA
```

<213> ORGANISM: Artificial Sequence
<220> FEATURE:
<223> OTHER INFORMATION: Synthetic construct
<220> FEATURE:
<223> OTHER INFORMATION: m = a or c

<400> SEQUENCE: 19
actagtcgac atggmttggg tgtggamctt gctattcctg        40

<210> SEQ ID NO 20
<211> LENGTH: 37
<212> TYPE: DNA
<213> ORGANISM: Artificial Sequence
<220> FEATURE:
<223> OTHER INFORMATION: Synthetic construct

<400> SEQUENCE: 20
actagtcgac atgggcagac ttacattctc attcctg        37

<210> SEQ ID NO 21
<211> LENGTH: 38
<212> TYPE: DNA
<213> ORGANISM: Artificial Sequence
<220> FEATURE:
<223> OTHER INFORMATION: Synthetic construct

<400> SEQUENCE: 21
actagtcgac atggattttg ggctgatttt ttttattg        38

<210> SEQ ID NO 22
<211> LENGTH: 37
<212> TYPE: DNA
<213> ORGANISM: Artificial Sequence
<220> FEATURE:
<223> OTHER INFORMATION: Synthetic construct

<400> SEQUENCE: 22
actagtcgac atgatggtgt taagtcttct gtacctg        37

<210> SEQ ID NO 23
<211> LENGTH: 40
<212> TYPE: DNA
<213> ORGANISM: Artificial Sequence
<220> FEATURE:
<223> OTHER INFORMATION: Synthetic construct

<400> SEQUENCE: 23
actagtcgac atgaagttgc ctgttaggct gttggtgctg        40

<210> SEQ ID NO 24
<211> LENGTH: 39
<212> TYPE: DNA
<213> ORGANISM: Artificial Sequence
<220> FEATURE:
<223> OTHER INFORMATION: Synthetic construct
<220> FEATURE:
<223> OTHER INFORMATION: w = a or t
<220> FEATURE:
<223> OTHER INFORMATION: y = t or c

<400> SEQUENCE: 24
actagtcgac atggagwcag acacactcct gytatgggt        39

<210> SEQ ID NO 25
<211> LENGTH: 40
<212> TYPE: DNA
<213> ORGANISM: Artificial Sequence
<220> FEATURE:

```
<223> OTHER INFORMATION: Synthetic construct
<220> FEATURE:
<223> OTHER INFORMATION: s = g or c

<400> SEQUENCE: 25
actagtcgac atgagtgtgc tcactcaggt cctggsgttg                           40

<210> SEQ ID NO 26
<211> LENGTH: 43
<212> TYPE: DNA
<213> ORGANISM: Artificial Sequence
<220> FEATURE:
<223> OTHER INFORMATION: Synthetic construct
<220> FEATURE:
<223> OTHER INFORMATION: r = g or a
<220> FEATURE:
<223> OTHER INFORMATION: w = a or t
<220> FEATURE:
<223> OTHER INFORMATION: y = t or c
<220> FEATURE:
<223> OTHER INFORMATION: m = a or c

<400> SEQUENCE: 26
actagtcgac atgaggrccc ctgctcagwt tyttggmwtc ttg                       43

<210> SEQ ID NO 27
<211> LENGTH: 40
<212> TYPE: DNA
<213> ORGANISM: Artificial Sequence
<220> FEATURE:
<223> OTHER INFORMATION: Synthetic construct
<220> FEATURE:
<223> OTHER INFORMATION: w = a or t

<400> SEQUENCE: 27
actagtcgac atggatttwc aggtgcagat twtcagcttc                           40

<210> SEQ ID NO 28
<211> LENGTH: 37
<212> TYPE: DNA
<213> ORGANISM: Artificial Sequence
<220> FEATURE:
<223> OTHER INFORMATION: Synthetic construct
<220> FEATURE:
<223> OTHER INFORMATION: k = g or t
<220> FEATURE:
<223> OTHER INFORMATION: y = t or c
<220> FEATURE:
<223> OTHER INFORMATION: s = g or c
<220> FEATURE:
<223> OTHER INFORMATION: r = g or a

<400> SEQUENCE: 28
actagtcgac atgaggtkcy ytgytsagyt yctgrgg                              37

<210> SEQ ID NO 29
<211> LENGTH: 41
<212> TYPE: DNA
<213> ORGANISM: Artificial Sequence
<220> FEATURE:
<223> OTHER INFORMATION: Synthetic construct
<220> FEATURE:
<223> OTHER INFORMATION: w = a or t
<220> FEATURE:
<223> OTHER INFORMATION: k = g or t
<220> FEATURE:
<223> OTHER INFORMATION: y = t or c

<400> SEQUENCE: 29
actagtcgac atgggcwtca agatggagtc acakwyycwg g                         41
```

<210> SEQ ID NO 30
<211> LENGTH: 41
<212> TYPE: DNA
<213> ORGANISM: Artificial Sequence
<220> FEATURE:
<223> OTHER INFORMATION: Synthetic construct
<220> FEATURE:
<223> OTHER INFORMATION: y = t or c
<220> FEATURE:
<223> OTHER INFORMATION: k = g or t
<220> FEATURE:
<223> OTHER INFORMATION: m = a or c

<400> SEQUENCE: 30
actagtcgac atgtggggay ctktttycmm tttttcaatt g                41

<210> SEQ ID NO 31
<211> LENGTH: 35
<212> TYPE: DNA
<213> ORGANISM: Artificial Sequence
<220> FEATURE:
<223> OTHER INFORMATION: Synthetic construct
<220> FEATURE:
<223> OTHER INFORMATION: r = g or a
<220> FEATURE:
<223> OTHER INFORMATION: w = a or t
<220> FEATURE:
<223> OTHER INFORMATION: s = g or c

<400> SEQUENCE: 31
actagtcgac atggtrtccw casctcagtt ccttg                       35

<210> SEQ ID NO 32
<211> LENGTH: 37
<212> TYPE: DNA
<213> ORGANISM: Artificial Sequence
<220> FEATURE:
<223> OTHER INFORMATION: Synthetic construct

<400> SEQUENCE: 32
actagtcgac atgtatatat gtttgttgtc tatttct                     37

<210> SEQ ID NO 33
<211> LENGTH: 38
<212> TYPE: DNA
<213> ORGANISM: Artificial Sequence
<220> FEATURE:
<223> OTHER INFORMATION: Synthetic construct

<400> SEQUENCE: 33
actagtcgac atggaagccc cagctcagct tctcttcc                    38

<210> SEQ ID NO 34
<211> LENGTH: 32
<212> TYPE: DNA
<213> ORGANISM: Artificial Sequence
<220> FEATURE:
<223> OTHER INFORMATION: Synthetic construct

<400> SEQUENCE: 34
tacgacccgg gactggatgg tgggaagatg ga                          32

<210> SEQ ID NO 35
<211> LENGTH: 35
<212> TYPE: DNA
<213> ORGANISM: Artificial Sequence
<220> FEATURE:
<223> OTHER INFORMATION: Synthetic construct

```
<400> SEQUENCE: 35
tacgacccgg gggagttagt ttgggcagca gatcc                              35

<210> SEQ ID NO 36
<211> LENGTH: 35
<212> TYPE: DNA
<213> ORGANISM: Artificial Sequence
<220> FEATURE:
<223> OTHER INFORMATION: Synthetic construct

<400> SEQUENCE: 36
tacgacccgg gagcagatcc aggggccagt ggata                              35

<210> SEQ ID NO 37
<211> LENGTH: 53
<212> TYPE: DNA
<213> ORGANISM: Homo sapiens

<400> SEQUENCE: 37
gaattctgca ggggatccgc caccatgatg gatcaagcta gatcagcatt ctc          53

<210> SEQ ID NO 38
<211> LENGTH: 41
<212> TYPE: DNA
<213> ORGANISM: Homo sapiens

<400> SEQUENCE: 38
ctcgagcggc cgccactgtt aaaactcatt gtcaatgtcc c                       41
```